(12) United States Patent
Tsai et al.

(10) Patent No.: US 10,258,502 B2
(45) Date of Patent: Apr. 16, 2019

(54) THERAPEUTIC AGENT DELIVERY DEVICE

(71) Applicant: ORBIT BIOMEDICAL LIMITED, London (GB)

(72) Inventors: Mark C. Tsai, Chalfont, PA (US); Brian M. Gatton, Jr., Franklinville, NJ (US); Michael F. Keane, Downingtown, PA (US); Isaac J. Khan, Bridgewater, NJ (US); Brendan J. Oberkircher, Cincinnati, OH (US); Daniel W. Price, Loveland, OH (US)

(73) Assignee: ORBIT BIOMEDICAL LIMITED, London (GB)

(*) Notice: Subject to any disclaimer, the term of this patent is extended or adjusted under 35 U.S.C. 154(b) by 445 days.

(21) Appl. No.: 14/843,350

(22) Filed: Sep. 2, 2015

(65) Prior Publication Data
US 2016/0081849 A1 Mar. 24, 2016

Related U.S. Application Data

(60) Provisional application No. 62/052,038, filed on Sep. 18, 2014, provisional application No. 62/052,043, (Continued)

(51) Int. Cl.
*A61J 1/06* (2006.01)
*A61M 5/20* (2006.01)
(Continued)

(52) U.S. Cl.
CPC ......... *A61F 9/0008* (2013.01); *A61M 5/2053* (2013.01); *A61M 5/3137* (2013.01);
(Continued)

(58) Field of Classification Search
CPC . A61F 9/0008; A61F 9/00727; A61M 5/2053; A61M 5/31595; A61M 5/31501;
(Continued)

(56) References Cited

U.S. PATENT DOCUMENTS 2,875,761 A 3/1959 Helmer et al.
4,231,494 A * 11/1980 Greenwood .......... B05C 17/002
222/179

(Continued)

FOREIGN PATENT DOCUMENTS

CN 1264005 A 8/2000
CN 1298313 A 6/2001
(Continued)

OTHER PUBLICATIONS

International Search Report and Written Opinion dated Apr. 25, 2016 for Application No. PCT/US2015/050394, 17 pgs.
(Continued)

*Primary Examiner* — Adam Marcetich
(74) *Attorney, Agent, or Firm* — Frost Brown Todd LLC

(57) ABSTRACT

A system for storing and delivering a predetermined amount of fluid includes a syringe including a barrel, a flange disposed at the proximal end of the barrel, and a plunger assembly configured to be received in the lumen of the barrel. The plunger assembly includes a piston and a plunger rod. The plunger rod is removably couplable to the piston at the distal end of the plunger rod and includes a thumb press flange at the proximal end of the plunger rod. The system further includes a stop feature that is removably couplable to the syringe or the plunger assembly. The stop feature is configured to arrest distal advancement of the plunger assembly relative to the syringe when the plunger assembly reaches a predetermined position relative to the syringe. The stop thus ensures that a predetermined amount of fluid remains in the barrel.

20 Claims, 69 Drawing Sheets

Related U.S. Application Data filed on Sep. 18, 2014, provisional application No. 62/052,059, filed on Sep. 18, 2014, provisional application No. 62/052,074, filed on Sep. 18, 2014.

(51) Int. Cl.
| | | |
|---|---|---|
| *A61M 5/315* | (2006.01) | |
| *A61F 9/00* | (2006.01) | |
| *A61M 5/31* | (2006.01) | |
| *A61M 39/10* | (2006.01) | |

(52) U.S. Cl.
CPC .... *A61M 5/31501* (2013.01); *A61M 5/31505* (2013.01); *A61M 5/31595* (2013.01); *A61M 5/3158* (2013.01); *A61M 2005/2086* (2013.01); *A61M 2005/3154* (2013.01); *A61M 2005/31508* (2013.01); *A61M 2039/1077* (2013.01)

(58) Field of Classification Search
CPC ............ A61M 5/3137; A61M 5/31505; A61M 2005/2086; A61M 2005/31508; A61M 5/3158; A61M 2039/1077; A61M 2005/3154; A61M 5/46; A61M 2205/583; A61M 5/31526; A61M 5/31536; A61M 5/31553; A61M 5/31555; A61M 5/31591
See application file for complete search history.

(56) References Cited

U.S. PATENT DOCUMENTS

| | | | | |
|---|---|---|---|---|
| 4,874,385 A * | 10/1989 | Moran | ............... | A61M 5/31555 604/208 |
| 5,019,037 A * | 5/1991 | Wang | ................. | A61F 9/00727 604/121 |
| 5,252,064 A * | 10/1993 | Baum | ................ | A61C 17/0202 433/80 |
| 5,496,285 A * | 3/1996 | Schumacher | ...... | A61M 5/31511 604/218 |
| 5,601,077 A * | 2/1997 | Imbert | ................... | A61M 11/00 128/200.14 |
| 5,782,815 A * | 7/1998 | Yanai | ...................... | A61J 1/062 222/386 |
| 5,803,918 A * | 9/1998 | Vetter | ................... | A61M 5/315 604/110 |
| 5,887,764 A * | 3/1999 | Ennis, III | ............. | B05C 17/015 222/153.01 |
| 5,975,355 A * | 11/1999 | Cecala | ............. | A61M 5/31591 222/283 |
| 7,329,241 B2 | 2/2008 | Horvath et al. | | |
| 7,413,734 B2 | 8/2008 | Mistry et al. | | |
| 2004/0122367 A1 * | 6/2004 | Sculati | .................. | A61F 9/0017 604/140 |
| 2004/0162528 A1 | 8/2004 | Horvath et al. | | |
| 2004/0254539 A1 * | 12/2004 | Wolbring | ............ | A61M 5/3135 604/187 |
| 2005/0137532 A1 * | 6/2005 | Rolla | .................. | A61M 5/3156 604/218 |
| 2005/0180806 A1 * | 8/2005 | Green | ................ | A61B 17/8822 401/119 |
| 2005/0288625 A1 * | 12/2005 | Rossback | ............ | A61M 5/2053 604/93.01 |
| 2006/0173415 A1 | 8/2006 | Cummins | | |
| 2007/0083164 A1 * | 4/2007 | Barrelle | ................ | A61J 7/0053 604/187 |
| 2007/0287965 A1 * | 12/2007 | Strong | ..................... | F16J 1/003 604/218 |
| 2009/0124996 A1 * | 5/2009 | Heneveld | .............. | A61F 2/0059 604/506 |
| 2009/0326479 A1 * | 12/2009 | Janish | ................ | A61M 5/31511 604/218 |
| 2011/0087173 A1 * | 4/2011 | Sibbitt, Jr. | ......... | A61B 10/0233 604/207 |
| 2011/0190704 A1 * | 8/2011 | Lynch | ................... | A61M 5/145 604/152 |
| 2012/0325367 A1 * | 12/2012 | Mathys | .............. | A61B 17/8833 141/18 |
| 2013/0043282 A1 * | 2/2013 | Niklasson | ........... | A61M 5/3137 222/390 |
| 2013/0178737 A1 * | 7/2013 | Anelli | ................. | A61M 5/3137 600/432 |
| 2014/0180245 A1 * | 6/2014 | Wong | .................... | A61M 5/315 604/506 |
| 2014/0303565 A1 * | 10/2014 | Kubo | .................... | A61M 15/08 604/208 |
| 2015/0223977 A1 | 8/2015 | Oberkircher et al. | | |
| 2016/0022920 A1 * | 1/2016 | Reeves | ............ | A61M 5/31536 604/506 |

FOREIGN PATENT DOCUMENTS

| | | |
|---|---|---|
| CN | 1617751 A | 5/2005 |
| CN | 1715725 A | 1/2006 |
| CN | 103816588 A | 5/2014 |
| EP | 1 092 447 A2 | 4/2001 |
| EP | 1 911 480 A1 | 4/2008 |
| EP | 2 708 254 A1 | 3/2014 |
| WO | WO 2012/148717 A1 | 11/2012 |

OTHER PUBLICATIONS

International Preliminary Report on Patentability dated Mar. 21, 2017 for Application No. PCT/US2015/050394, 10 pgs.
U.S. Appl. No. 62/052,038, filed Sep. 18, 2014.
U.S. Appl. No. 62/052,043, filed Sep. 18, 2014.
U.S. Appl. No. 62/052,059, filed Sep. 18, 2014.
U.S. Appl. No. 62/052,074, filed Sep. 18, 2014.
Chinese Office Action dated Nov. 27, 2018 for Application No. 201580062516.1, 9 pages.

* cited by examiner

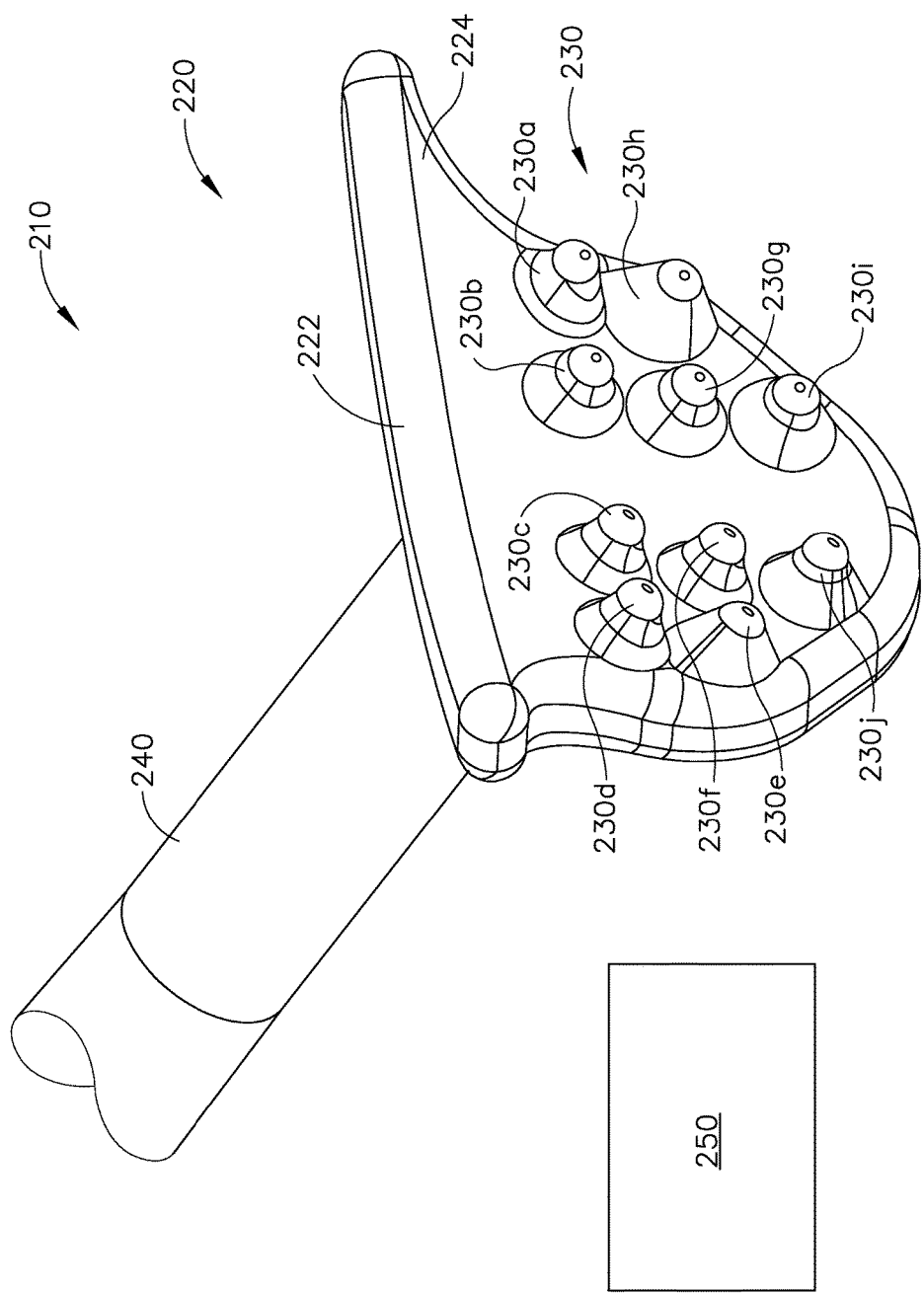

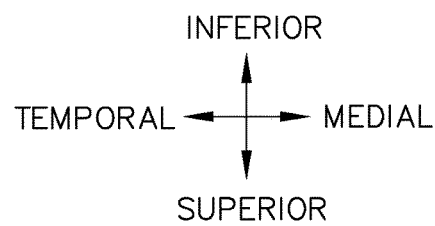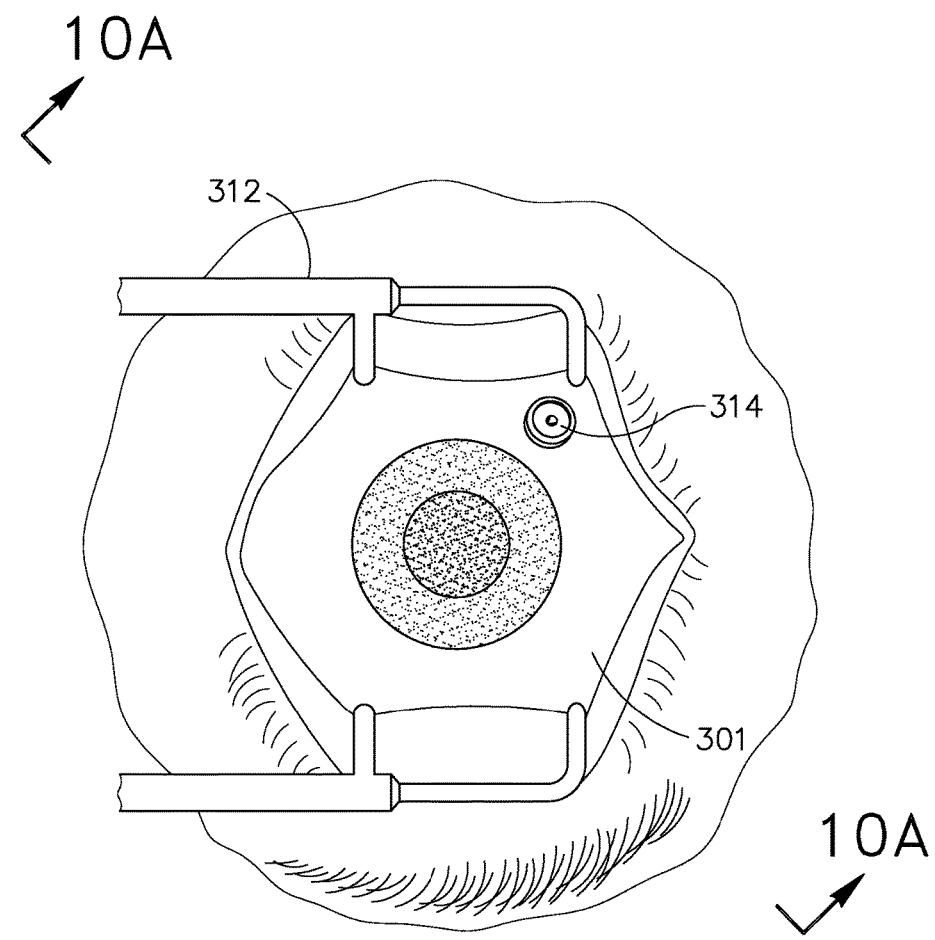
Fig.9A

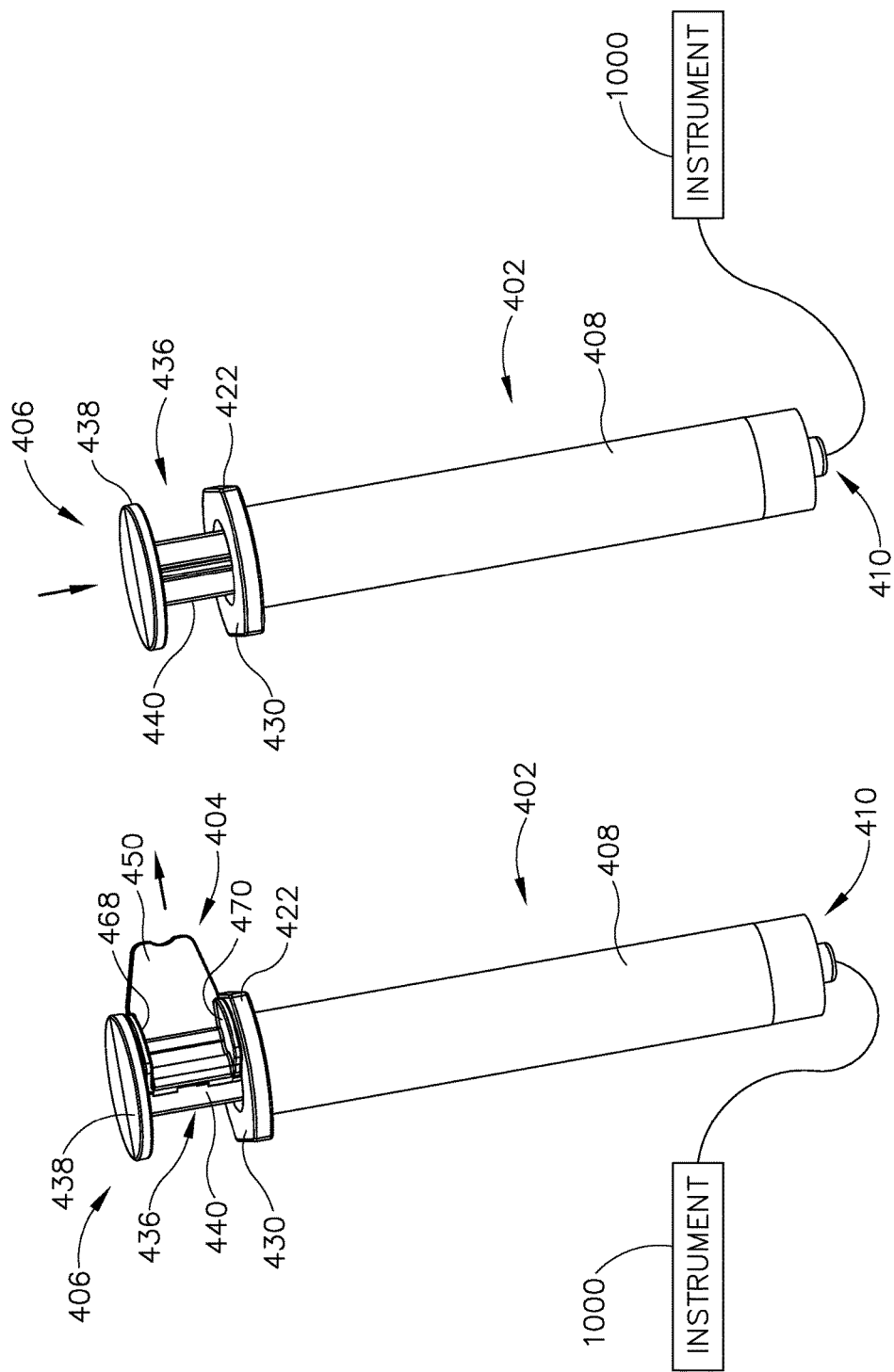

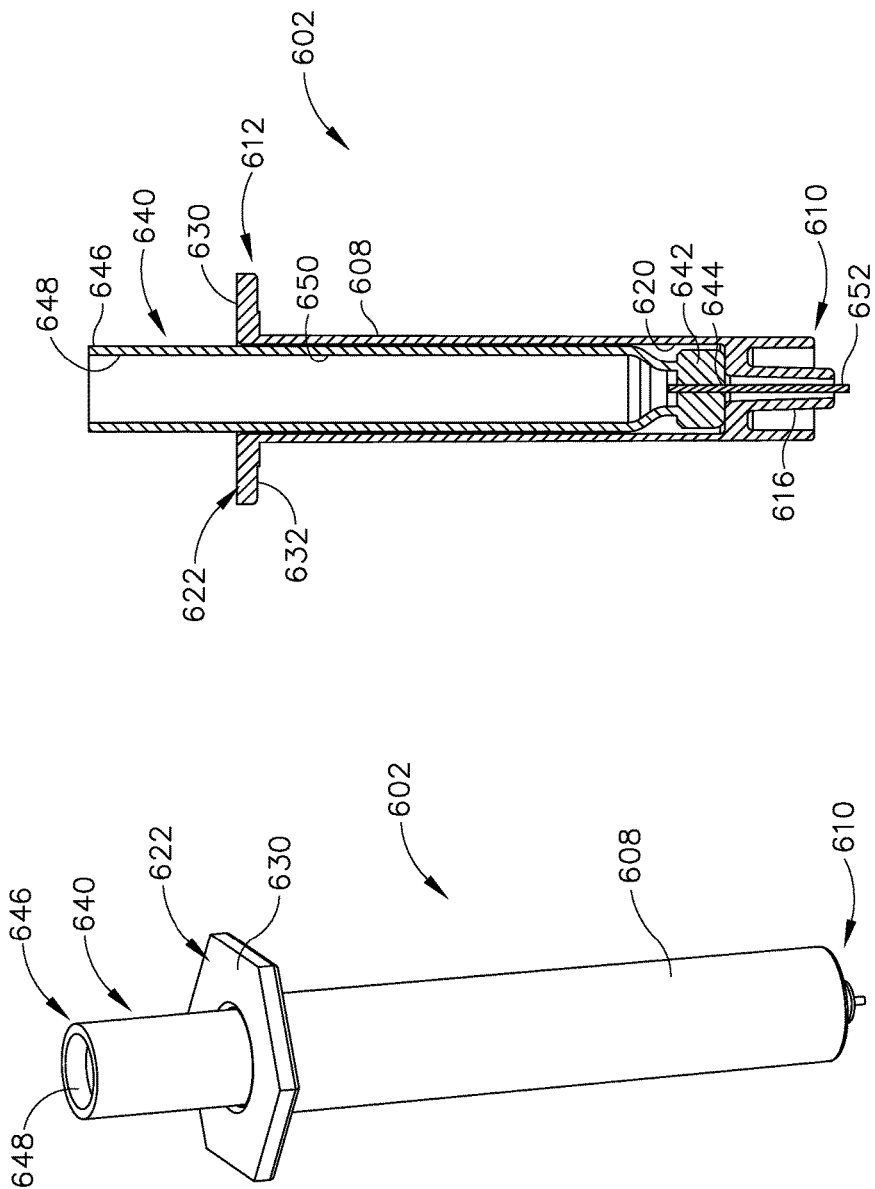

THERAPEUTIC AGENT DELIVERY DEVICE

PRIORITY

This application claims priority to U.S. Provisional Patent Application No. 62/052,038, entitled "Measurement Tab for Micro Volumetric Cell Solution Delivery," filed Sep. 18, 2014, the disclosure of which is incorporated by reference herein.

This application claims priority to U.S. Provisional Patent Application No. 62/052,043, entitled "Pneumatic Pressure Control Delivery System," filed Sep. 18, 2014, the disclosure of which is incorporated by reference herein.

This application claims priority to U.S. Provisional Patent Application No. 62/052,059, entitled "Snap Collar Syringe Adaptor," filed Sep. 18, 2014, the disclosure of which is incorporated by reference herein.

This application claims priority to U.S. Provisional Patent Application No. 62/052,074, entitled "Syringe Vessel with Detachable Plunger Rod," filed Sep. 18, 2014, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of an exemplary suture measurement template for use in an exemplary method for the subretinal administration of a therapeutic agent from a suprachoroidal approach;

FIG. 9A depicts a top plan view of an eye of a patient, with surrounding structures of the eye immobilized and a chandelier installed;

FIG. 12C depicts a perspective view of the syringe assembly of FIG. 12A, with the plunger advanced to a position governed by the measurement tab, and with the syringe in communication with an instrument for subretinal administration of a therapeutic agent from a suprachoroidal approach;

FIG. 12D depicts a perspective view of the syringe of FIG. 12A, with the measurement tab removed from the plunger, and with the syringe in communication with the instrument;

FIG. 22 depicts a perspective view of an exemplary alternative syringe that may be used with the instruments of FIGS. 1 and 7;

FIG. 23 depicts a side cross-sectional view of the syringe of FIG. 22;

Figure 1:
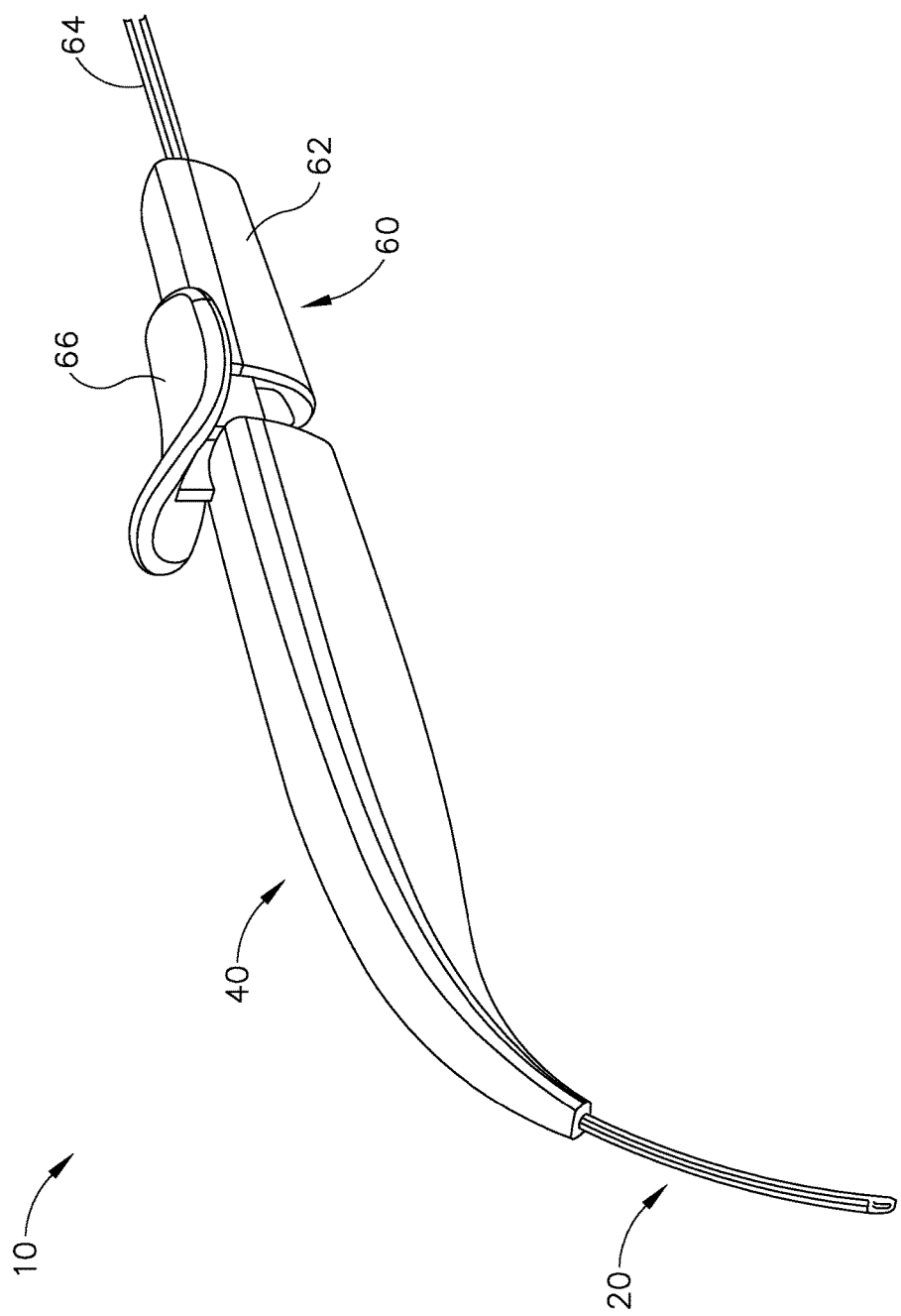
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument with Slider Articulation Feature

FIGS. 1-4 show an exemplary instrument (10) that is configured for use in a procedure for the subretinal administration of a therapeutic agent to an eye of a patient from a suprachoroidal approach. Instrument (10) comprises a flexible cannula (20), a body (40), and a sliding actuation assembly (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27D, approximately 33D, approximately 42D, approximately 46D, or any other suitable shore hardness. It should be understood that the shore hardness may fall within the range of approximately 27D to approximately 46D; or more particularly within the range of approximately 33D to approximately 46D; or more particularly within the range of approximately 40D to approximately 45D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a flexural stiffness for cannula (20). Flexural stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m$^2$, and an area moment of inertia ($I_x$) of $5.52 \times 10^{-14}$ m$^4$, providing a calculated flexural stiffness about the x-axis at $0.7 \times 10^{-6}$ Nm$^2$. Another exemplary material that may be used to form cannula (20) may have a shore hardness of D33, an elastic modulus (E) of $2.1 \times 10^7$ N/m$^2$, and an area moment of inertia ($I_x$) of $5.52 \times 10^{-14}$ m$^4$, providing a calculated flexural stiffness about the x-axis at $1.2 \times 10^{-6}$ Nm$^2$. Another exemplary material that may be used to form cannula (20) may have a shore hardness of D42, an elastic modulus (E) of $7.7 \times 10^{-7}$ N/m$^2$, and an area moment of inertia ($I_x$) of $5.52 \times 10^{-14}$ m$^4$, providing a calculated flexural stiffness about the x-axis at $4.3 \times 10^{-6}$ Nm$^2$. Another exemplary material that may be used to form cannula (20) may have a shore hardness of D46, an elastic modulus (E) of $17.0 \times 10^{-7}$ N/m$^2$, and an area moment of inertia ($I_x$) of $5.52 \times 10^{-14}$ m$^4$, providing a calculated flexural stiffness about the x-axis at $9.4 \times 10^{-6}$ Nm$^2$. Thus, by way of example only, the flexural stiffness of cannula (20) may fall within the range of approximately $0.7 \times 10^{-6}$ Nm$^2$ to approximately $9.4 \times 10^{-6}$ Nm$^2$; or more particularly within the range of approximately $1.2 \times 10^{-6}$ Nm$^2$ to approximately $9.4 \times 10^{-6}$ Nm$^2$; or more particularly within the range of approximately $2.0 \times 10^{-6}$ Nm$^2$ to approximately $7.5 \times 10^{-6}$ Nm$^2$; or more particularly within the range of approximately $2.0 \times 10^{-6}$ Nm$^2$ to approximately $6.0 \times 10^{-6}$ Nm$^2$; or more particularly within the range of approximately $3.0 \times 10^{-6}$ Nm$^2$ to approximately $5.0 \times 10^{-6}$ Nm$^2$; or more particularly within the range of approximately $4.0 \times 10^{-6}$ Nm$^2$ to approximately $5.0 \times 10^{-6}$ Nm$^2$.

In the present example, the flexibility of cannula (20) may also be quantified by the following formula:

$$\delta = \frac{FL^3}{48 EI} \quad (1)$$

In the above equation, flexural stiffness (EI) is calculated experimentally by deflecting cannula (20) having a fixed span (L) a set distance to yield a predetermined amount of deflection (δ). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated flexural stiffness about the x-axis of $5.5 \times 10^{-6}$ Nm$^2$. In another exemplary material that may be used to form cannula (20) may require a force of 0.0205 N to achieve a deflection of 0.0135 m, providing a calculated flexural stiffness about the x-axis of $6.8 \times 10^{-6}$ Nm$^2$. In still another exemplary material that may be used to form cannula (20) may require a force of 0.0199 N to achieve a deflection of 0.0099 m, providing a calculated flexural stiffness about the x-axis of $9.1 \times 10^{-6}$ Nm$^2$. In yet another exemplary material that may be used to form cannula (20) may require a force of 0.0241 N to achieve a deflection of 0.0061 m, providing a calculated flexural stiffness about the x-axis of $1.8 \times 10^{-6}$ Nm$^2$. In yet another exemplary material that may be used to form cannula (20) may require a force of 0.0190 N to achieve a deflection 0.0081 m, providing a calculated flexural stiffness about the x-axis of $1.0 \times 10^{-6}$ Nm$^2$. In yet another exemplary material that may be used to form cannula (20) may require a force of 0.0215 N to achieve a deflection of 0.0114 m, providing a calculated flexural stiffness about the x-axis of $8.4 \times 10^{-6}$ Nm$^2$. In yet another exemplary material that may be used to form cannula (20) may require a force of 0.0193 N to achieve a deflection of 0.0170 m, providing a calculated flexural stiffness about the x-axis of $5.1 \times 10^{-6}$ Nm$^2$. In yet another exemplary material that may be used to form cannula (20) may require a force of 0.0224 N to achieve a deflection of 0.0152 m, providing a calculated flexural stiffness about the x-axis of $6.6 \times 10^{-6}$ Nm$^2$. In yet another exemplary material that may be used to form cannula (20) may require a force of 0.0183 N to achieve a deflection of 0.0119 m, providing a calculated flexural stiffness about the x-axis of $6.9 \times 10^{-6}$ Nm$^2$. In yet another exemplary material that may be used to form cannula (20) may require a force of 0.0233 N to achieve a deflection of 0.0147 m, providing a calculated flexural stiffness about the x-axis of $7.1 \times 10^{-6}$ Nm$^2$. In yet another exemplary material that may be used to form cannula (20) may require a force of 0.0192 N to achieve a deflection of 0.0122, providing a calculated flexural stiffness about the x-axis of $7.1 \times 10^{-6}$ Nm$^2$. In yet another exemplary material that may be used to form cannula (20) may require a force of 0.0201 N to achieve a deflection of 0.0201, providing a calculated flexural stiffness about the x-axis of $4.5 \times 10^{-6}$ Nm$^2$. Thus, by way of example only, the flexural stiffness of cannula (20) may fall within the range of approximately $1.0 \times 10^{-6}$ Nm$^2$ to approximately $9.1 \times 10^{-6}$ Nm$^2$. It should be understood that in other examples, the flexural stiffness of cannula may fall within the range of approximately $0.7 \times 10^{-6}$ Nm$^2$ to approximately $11.1 \times 10^{-6}$ Nm$^2$; or more particularly within the range of approximately $2.0 \times 10^{-6}$ Nm$^2$ to approximately $6.0 \times 10^{-6}$ Nm$^2$.

Needle (30) may have a flexural stiffness that differs from the flexural stiffness of cannula (20). By way of example only, needle (30) may be formed of a nitinol material that has an elastic modulus (E) of $7.9 \times 10^{10}$ N/m$^2$, and an area moment of inertia ($I_x$) of $2.12 \times 10^{-17}$ m$^4$, providing a calculated flexural stiffness about the x-axis at $1.7 \times 10^{-6}$ Nm$^2$. By way of further example only, the flexural stiffness of needle (30) may fall within the range of approximately $0.5 \times 10^{-6}$ Nm$^2$ to approximately $2.5 \times 10^{-6}$ Nm$^2$; or more particularly within the range of approximately $0.75 \times 10^{-6}$ Nm$^2$ to approximately $2.0 \times 10^{-6}$ Nm$^2$; or more particularly within the range of approximately $1.25 \times 10^{-6}$ Nm$^2$ to approximately $1.75 \times 10^{-6}$ Nm$^2$.

Figure 5:
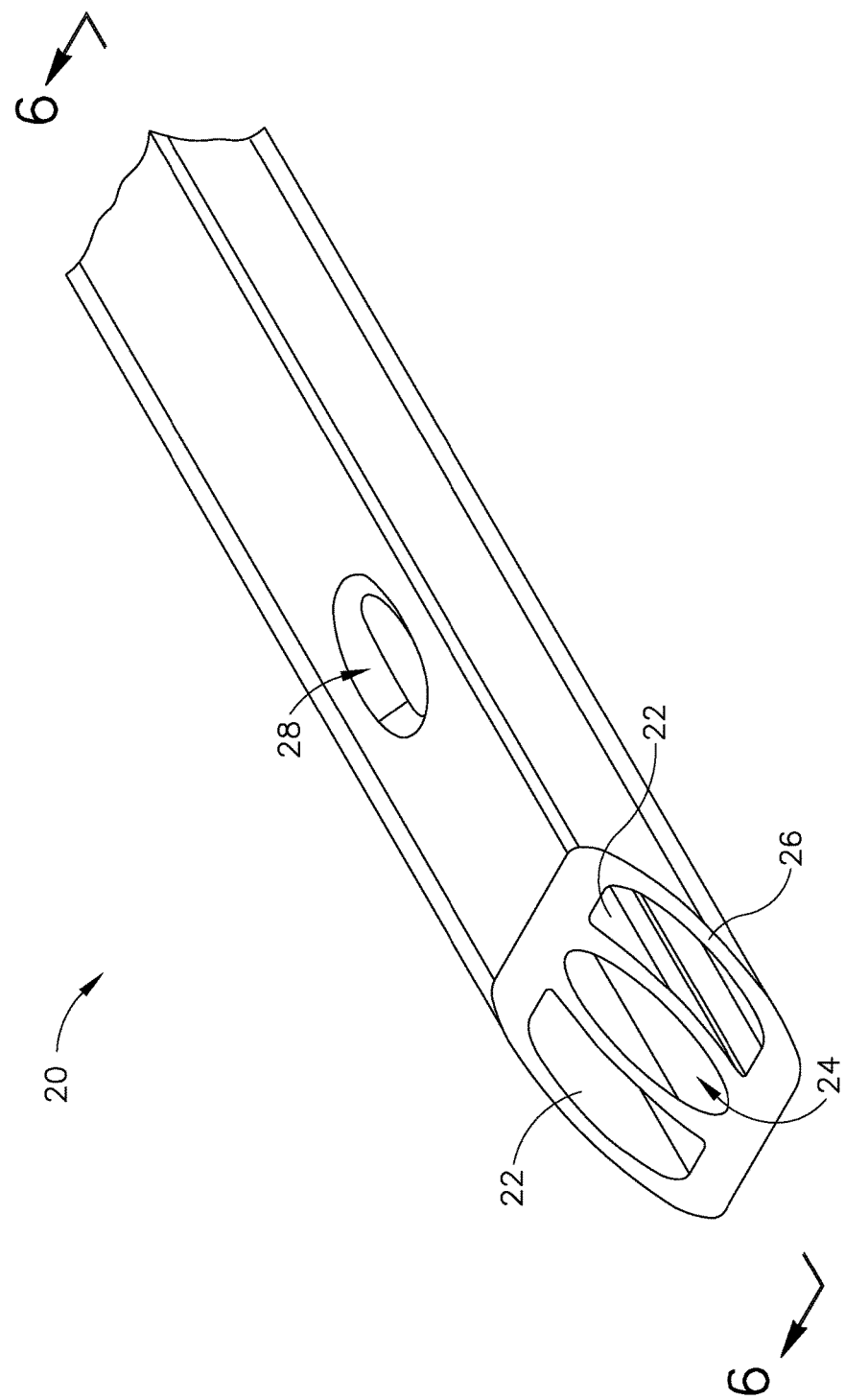
FIG. 5 depicts a perspective view of the distal end of an exemplary cannula that may be incorporated into the instrument of FIG. 1.
Figure 6:
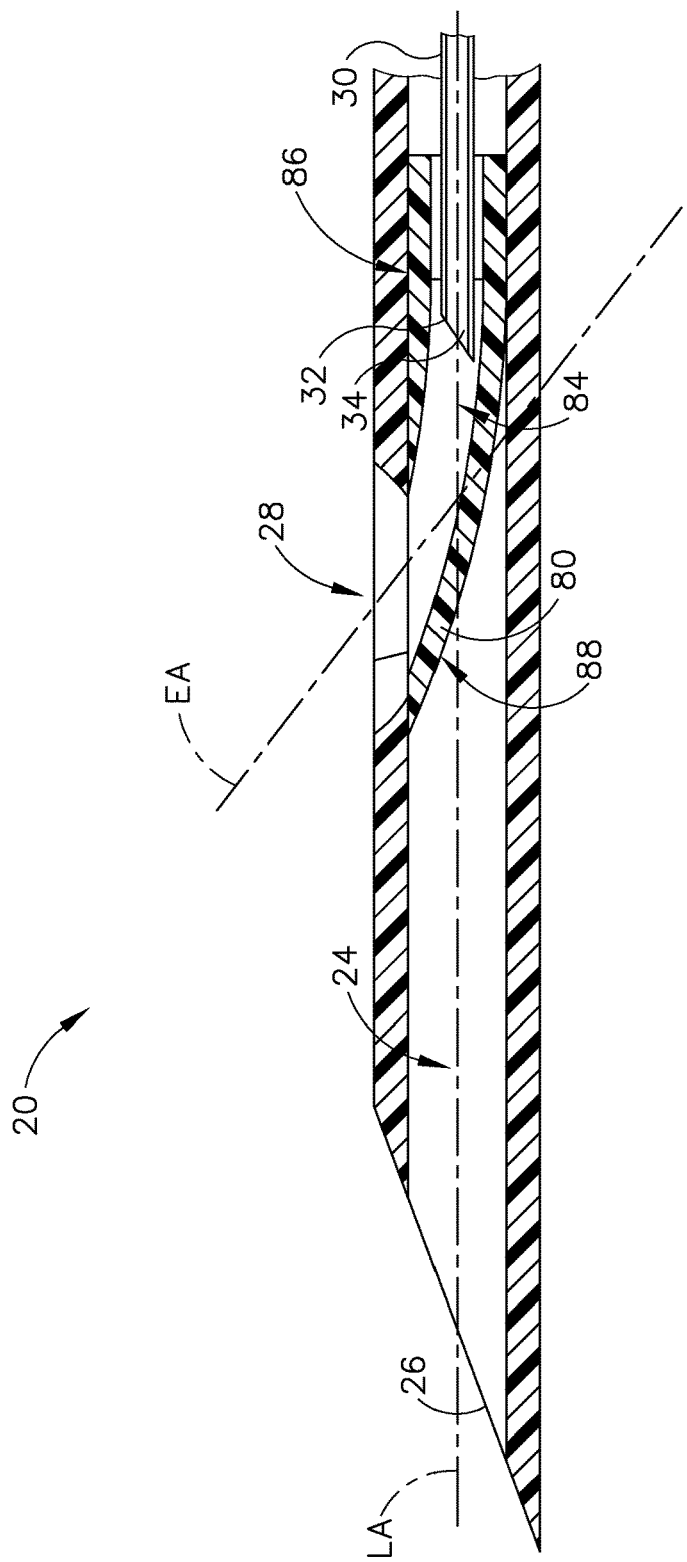
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) is in the form of an inner cannula has a sharp distal end (32) and defines an internal lumen (34). Distal end (32) of the present example has a lancet configuration. In some other versions, distal end (32) has a tri-bevel configuration or any other configuration as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Still other suitable forms that distal end (32) may take will be apparent to those of ordinary skill in the art in view of the teachings herein. Needle (30) of the present example comprises a metallic (e.g., nitinol, stainless steel, etc.) hypodermic needle that is sized to deliver the therapeutic agent while being small enough to create self-sealing wounds as needle (30) penetrates tissue structures of the patient's eye, as will be described in greater detail below. By way of example only, needle (30) may be 35 gauge with a 100 µm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 µm to approximately 200 µm; or more particularly within the range of approximately 50 µm to approximately 150 µm; or more particularly within the range of approximately 75 µm to approximately 125 µm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
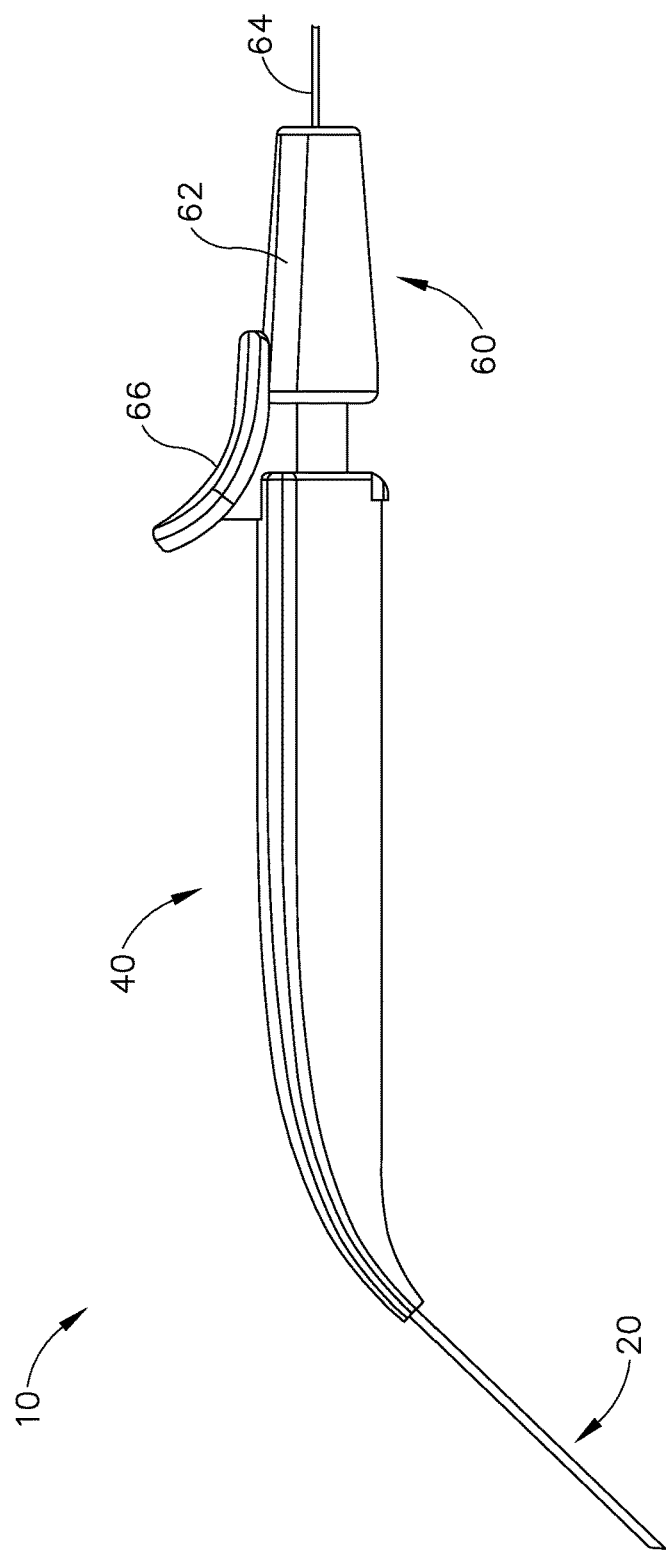
FIG. 2 depicts a side elevational view of the instrument of FIG. 1.
Figure 3:
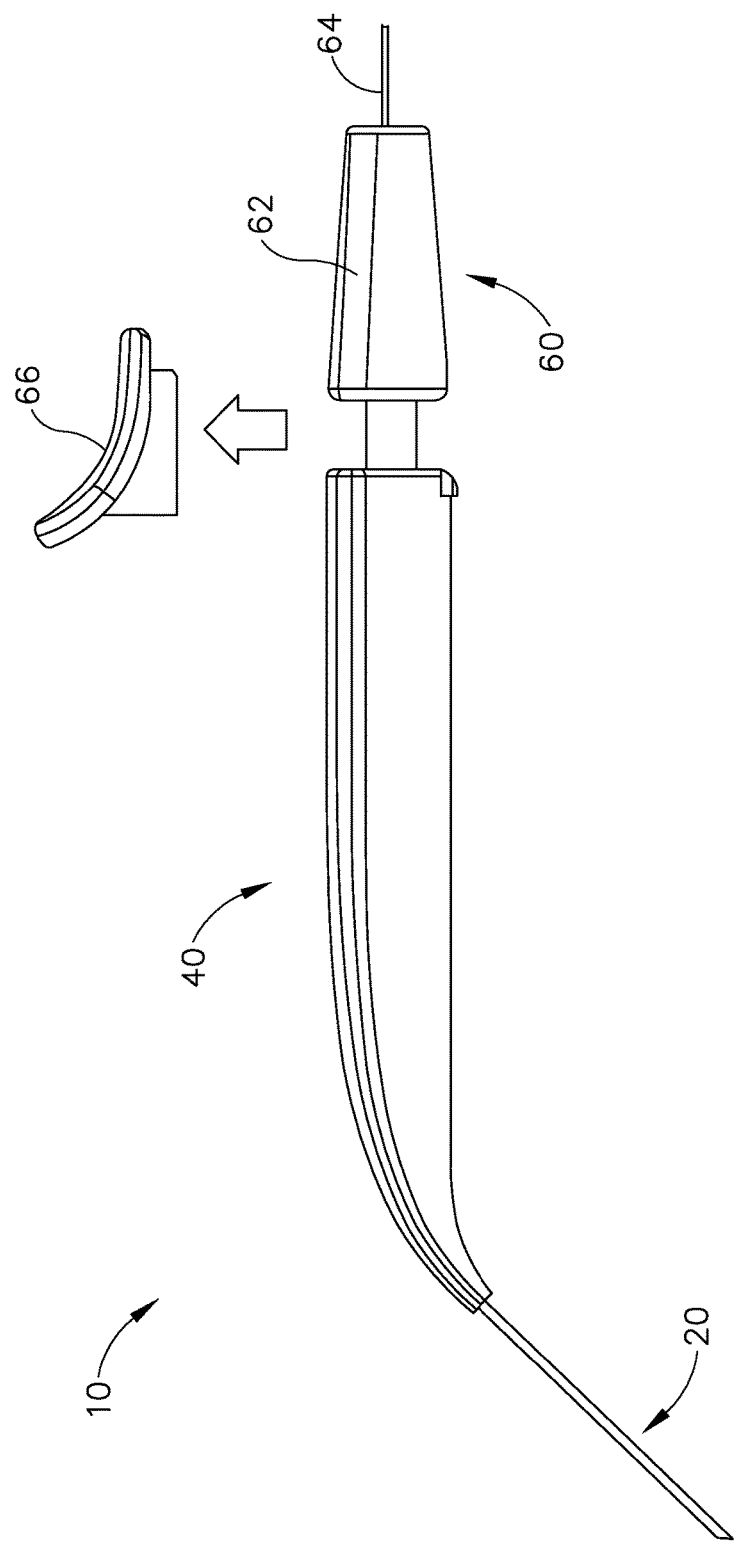
FIG. 3 depicts another side elevational view of the instrument of FIG. 1, with a locking member removed.
Figure 4:
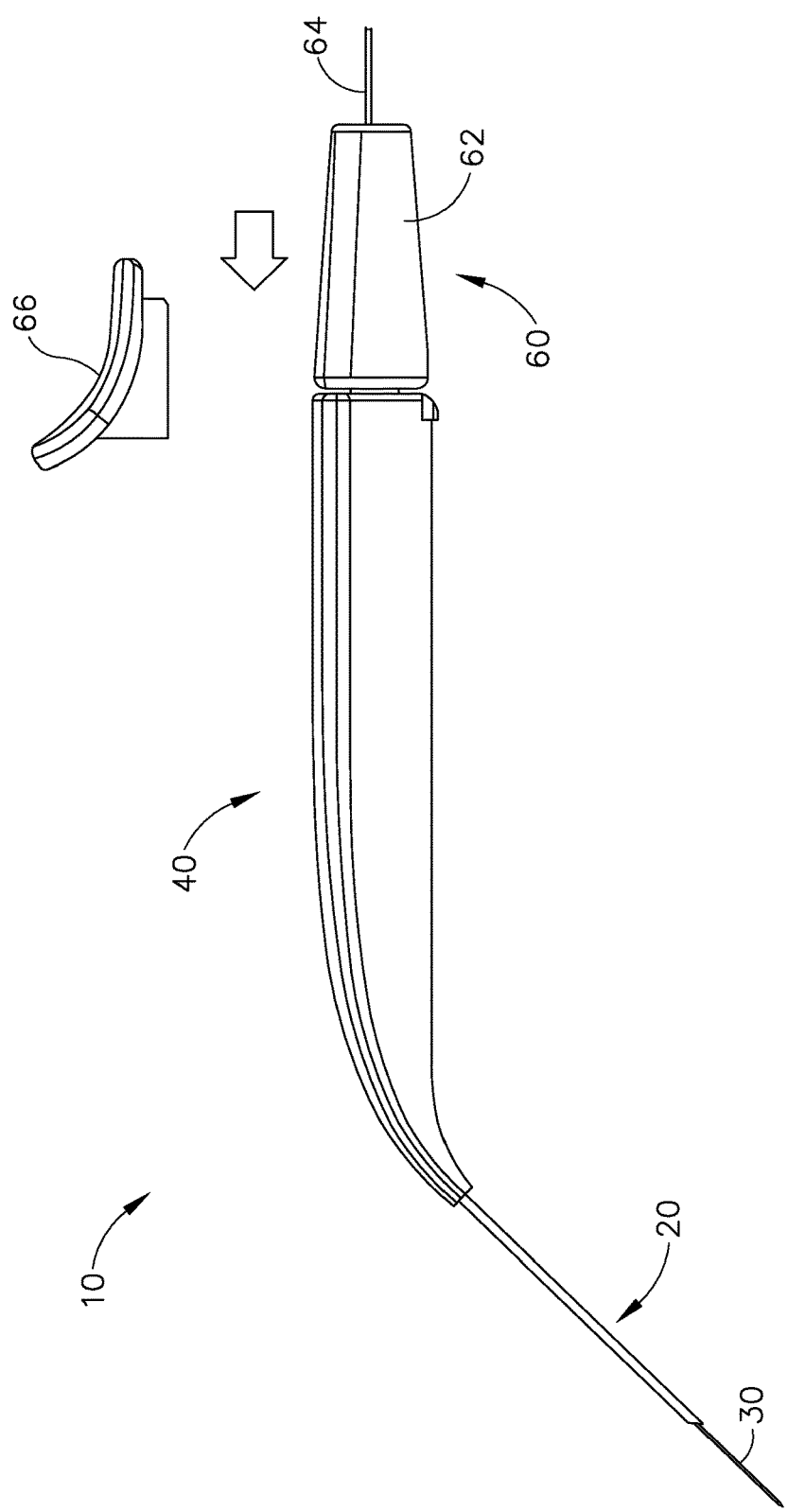
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

Actuation member (62) includes a lumen (not shown) extending longitudinally though actuation member (62). The lumen of actuation member (62) is configured to receive supply tube (64). In particular, supply tube (64) connects to the fluid coupling member of body engagement portion (not shown), extends proximally through body engagement portion, proximally through actuation member (62), and proximally out through the proximal end of actuation member (62). Thus, supply tube (64) defines a conduit through actuation member (62) to needle (30) such that fluid may be injected via supply tube (64) through needle (30) to an injection site. In the present example, the proximal end of supply tube (64) connects to a fluid source such as a syringe, an automated or semi-automated injector, or any other suitable fluid source. It should be understood that the proximal end of supply tube (64) may include a luer fitting and/or any other suitable kind of fitting to enable supply tube (64) to be releasably coupled with a fluid source.

II. Exemplary Alternative Instruments and Features

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

Figure 7:
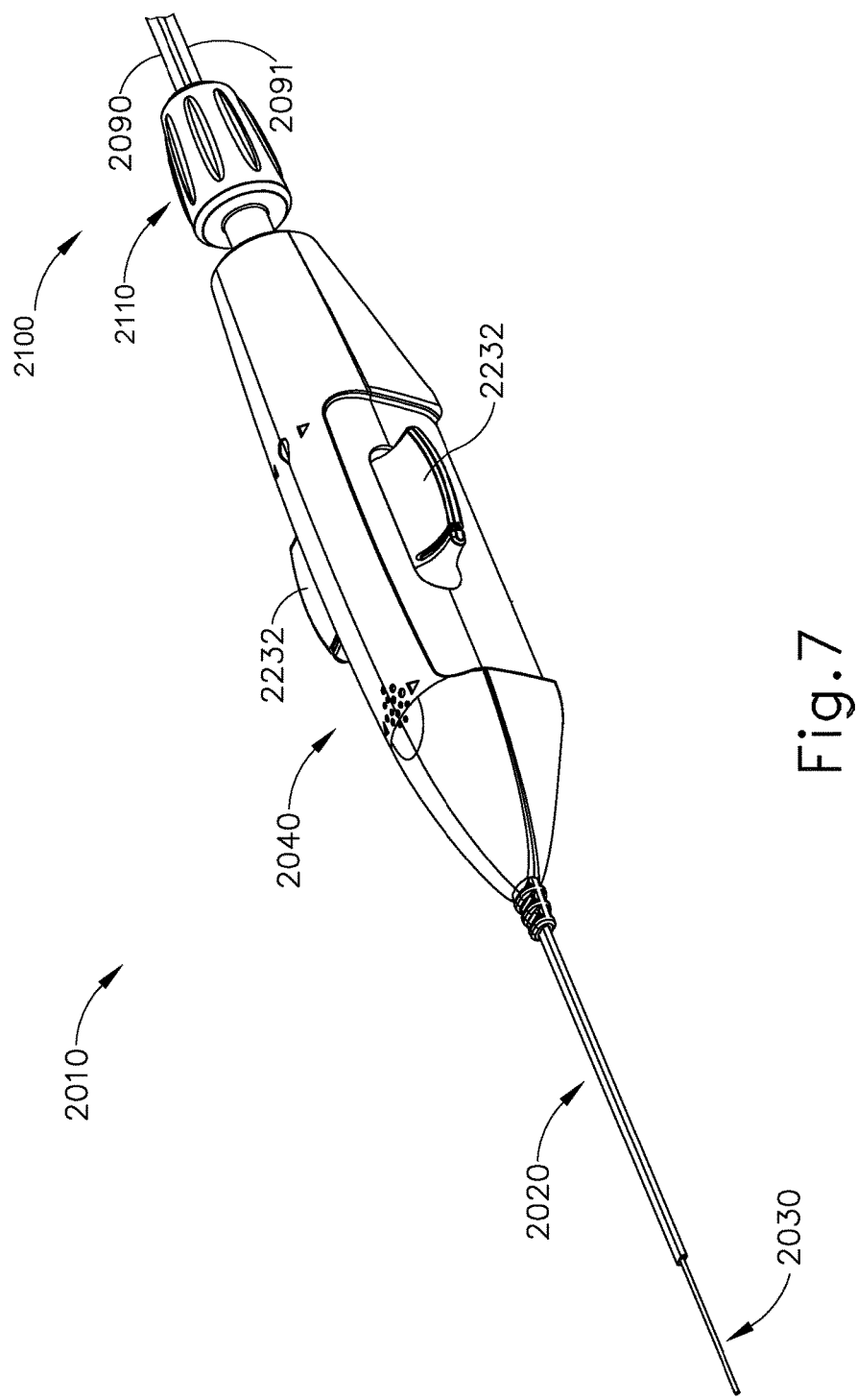
FIG. 7 depicts a perspective view of another exemplary alternative instrument for subretinal administration of a therapeutic agent from a suprachoroidal approach.

FIG. 7 shows an exemplary alternative instrument (2010) that is similar to instrument (10) described above. While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. Like with instrument (10), instrument (2010) of the present example is generally usable in the procedure described herein to deliver a therapeutic fluid subretinally to an eye of a patient from a suprachoroidal approach. It should therefore be understood that instrument (2010) may be readily used in place of instrument (10) to perform the medical procedures described herein. Like instrument (10), instrument (2010) of this example comprises a cannula (2020), a body (2040), and an actuation assembly (2100). Cannula (2020) includes a nitinol needle (2030) extending therethrough and is substantially the same as cannula (20) described above. In the present example, cannula (2020) and needle (2030) are substantially identical to cannula (20) and needle (30) described above.

The primary difference between instrument (10) and instrument (2010) is that actuation assembly (2100) of instrument (2010) is rotatable instead of being slidable. Additionally, instrument (2010) includes a valve assembly (not shown) that is operable to change the fluid state of needle (2030) according to the configuration or position of arms (2232). Particularly, arms (2232) are actuatable among three positions whereby needle (2030) is in three different fluid states. In the first position of arms (2232) shown in FIG. 7, valve assembly allows fluid to pass through both first supply tube (2090) and second supply tube (2091) to needle (2030). In a second position of arms (2232), valve assembly allows fluid to pass through first supply tube (2090) to needle (2030), but prevents fluid from passing through second supply tube (2091) to needle (2030). In a third position of arms (2232) valve assembly allows fluid to pass through second supply tube (2091) to needle (2030) but prevents fluid from passing through first supply tube (2090) to needle (2030). In the present example, first supply tube (2090) is configured to couple with a source of bleb fluid (340) (e.g., BSS); while second supply tube (2091) is configured to couple with a source of therapeutic agent (e.g., therapeutic agent (341)). It should be understood that each fluid supply tube (2090, 2091) may include a conventional luer feature and/or other structures permitting fluid supply tubes (2090, 2091) to be coupled with respective fluid sources. Actuation assembly (2100) is generally operable to translate the valve assembly longitudinally to thereby translate needle (2030) longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), the valve assembly, and needle (2030), an operator may rotate knob member (2110) in the clockwise direction. Clockwise rotation of knob member (2110) will act to translate knob member (2110) distally and will also act to translate the valve assembly and needle (2030) distally. An operator may continue clockwise rotation of knob member (2110) to drive needle (2030) out of the distal end of cannula (2020). Once needle (2030) has been advanced to its furthest distal position relative to the distal end of cannula (2020), further clockwise rotation of knob member (2110) will merely result in free rotation of knob member (2110) due to slipping of clutch features that are integrated into actuation assembly (2100). With needle (2030) in the distal position, the operator may actuate valve assembly to enable the delivery of therapeutic agent via needle (2030) as described in greater detail below.

After the therapeutic agent is delivered, the operator may then wish to retract needle (2030). Counter clockwise rotation of knob member (2110) will cause proximal translation of actuation assembly (2100), the valve assembly, and needle (2030) relative to body (2040). It should be understood that as actuation assembly (2100) is rotated to actuate the valve assembly, and needle (2030), the valve assembly and needle (2030) remain substantially rotationally stationary relative to body (2040). It should also be understood that although rotation member (2110) of the present example is described as being manually rotated, rotation member (2110) may be rotated via a motor and/or some other motive source. Thus, it should be understood that translation of needle (2030) may be mechanically/electrically driven via a servomotor. The actuation of a servomotor may be controlled by a servo controller as will be described in more detail below. Such a servo control may be manually operated. Additionally or alternatively, such a servo controller may be operated via a computer acting on feedback from instrument (2010) or any other component described herein.

III. Exemplary Suture Measurement Template

FIG. 8 shows an exemplary suture measurement template (210) that may be used in a procedure providing subretinal delivery of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. Exemplary Method for Subretinal Delivery of Therapeutic Agent from a Suprachoroidal Approach FIGS. 9A-11C show an exemplary procedure for subretinal delivery of therapeutic agent from a suprachoroidal approach using instrument (10) described above. It should be understood however, that instrument (2010) may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 9B:
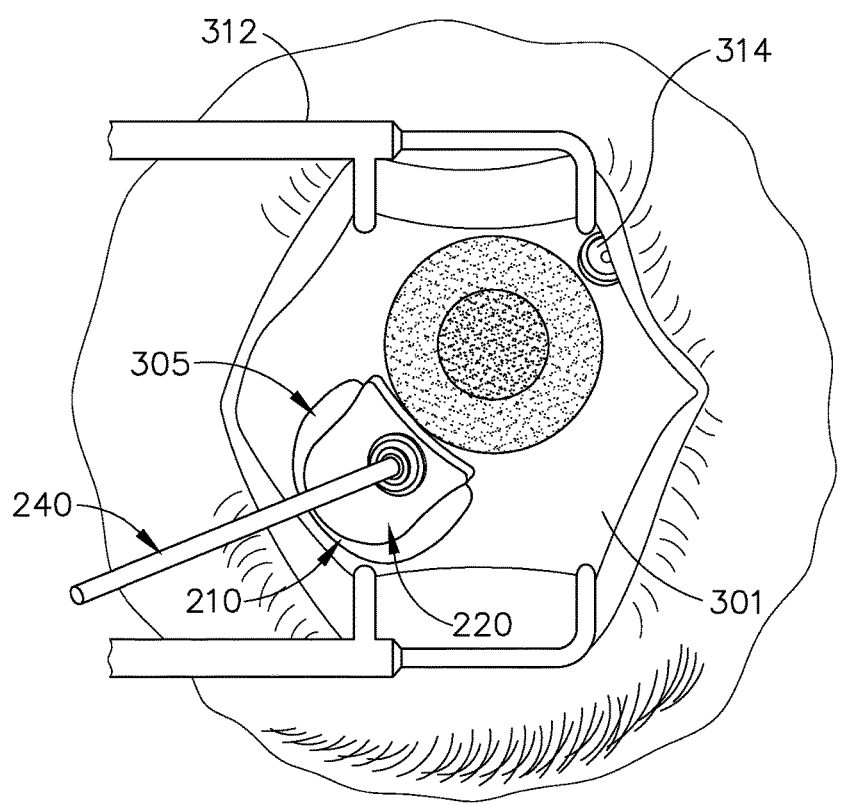
FIG. 9B depicts a top plan view of the eye of FIG. 9A, with the template of FIG. 8 disposed on the eye.
Figure 10A:
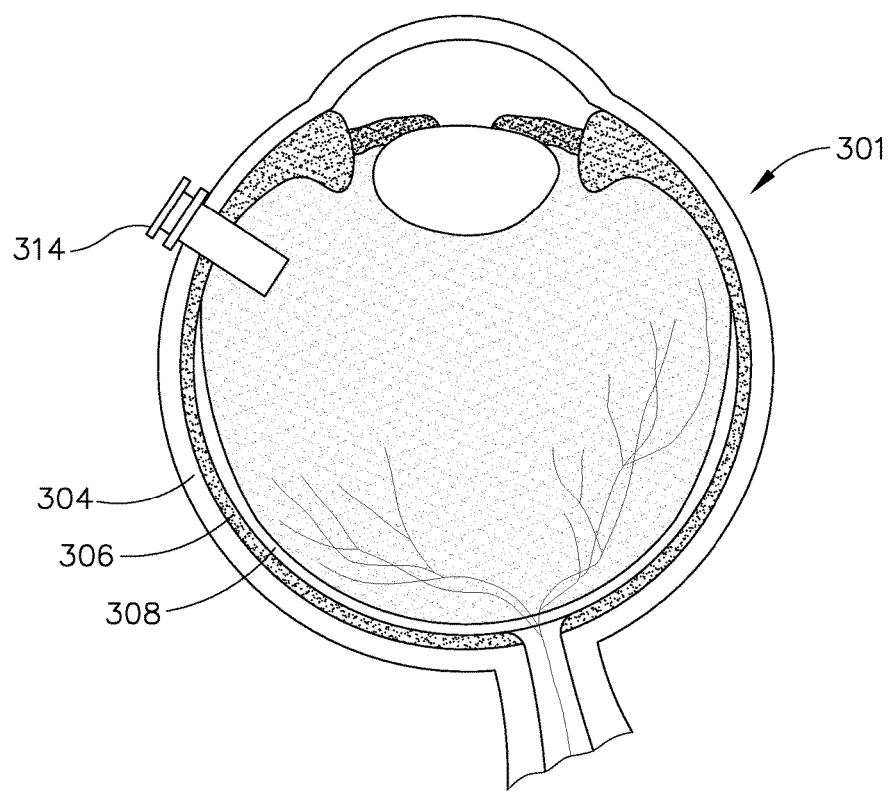
FIG. 10A depicts a cross-sectional view of the eye of FIG. 9A, with the cross-section taken about line 10A-10A of FIG. 9A.
Figure 10B:
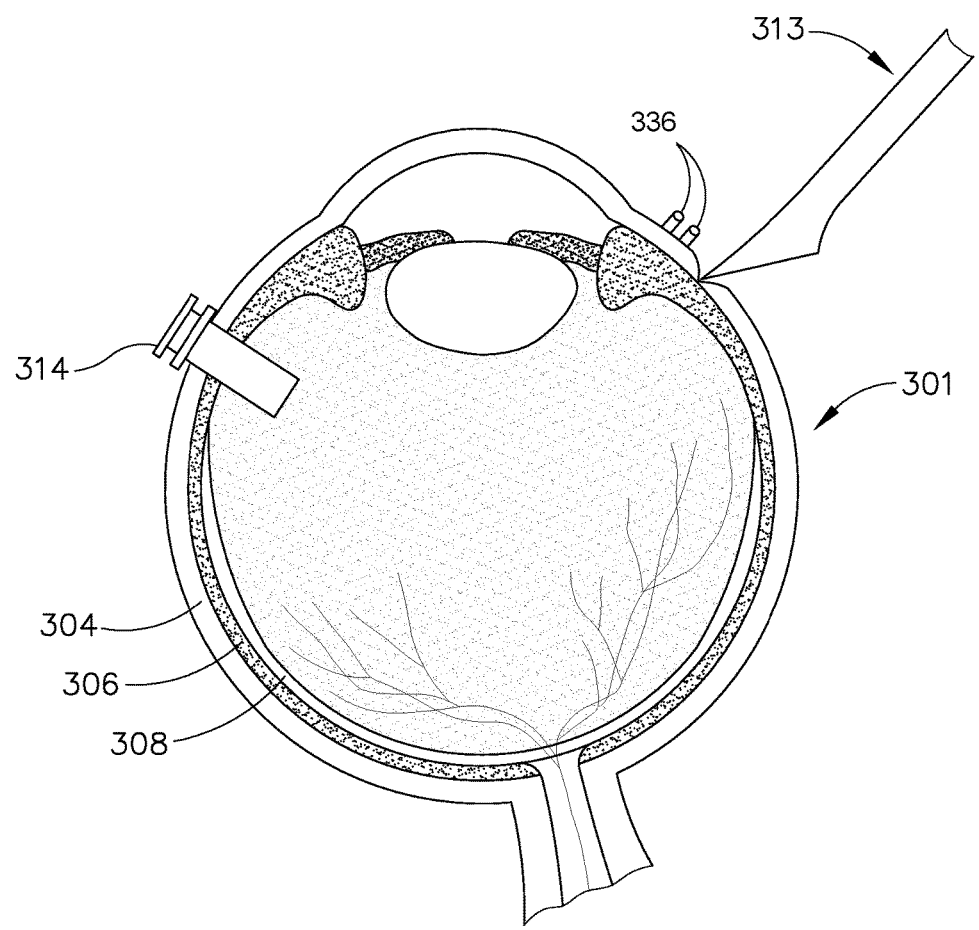
FIG. 10B depicts a cross-sectional view of the eye of FIG. 9A, with the cross-section taken about line 10B-10B of FIG. 9E.

As can be seen in FIG. 9A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 9A shows a particular positioning of eye chandelier port (314), it should be understood that eye chandelier port (314) may have any other positioning as will be apparent to those of ordinary skill in the art in view of the teachings herein.

Figure 9C:
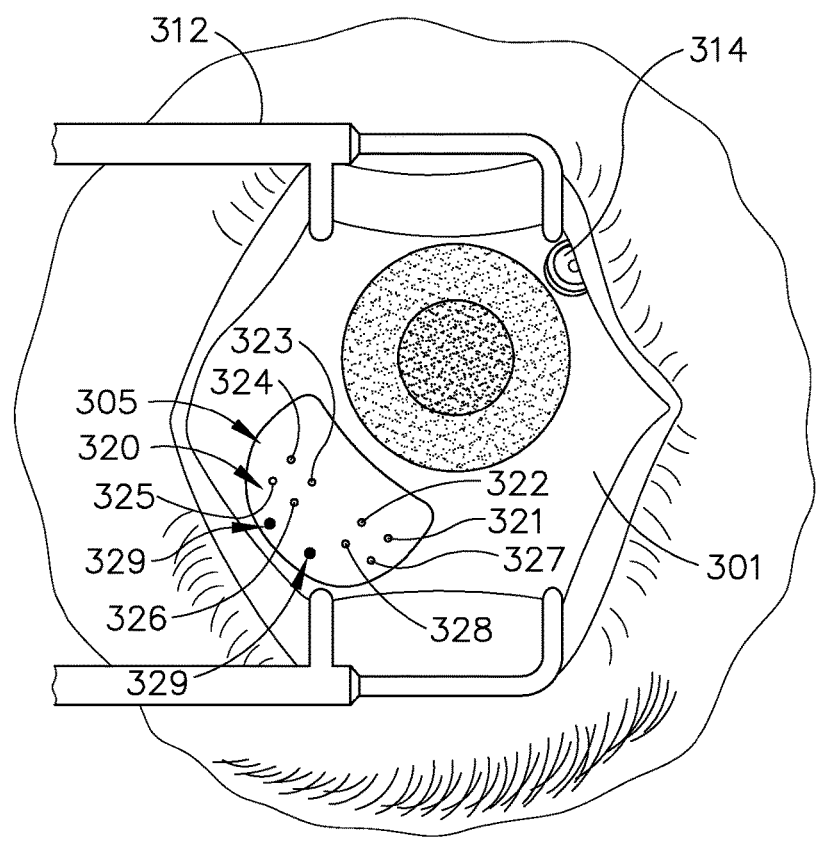
FIG. 9C depicts a top plan view of the eye of FIG. 9A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 9B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 9C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 9D:
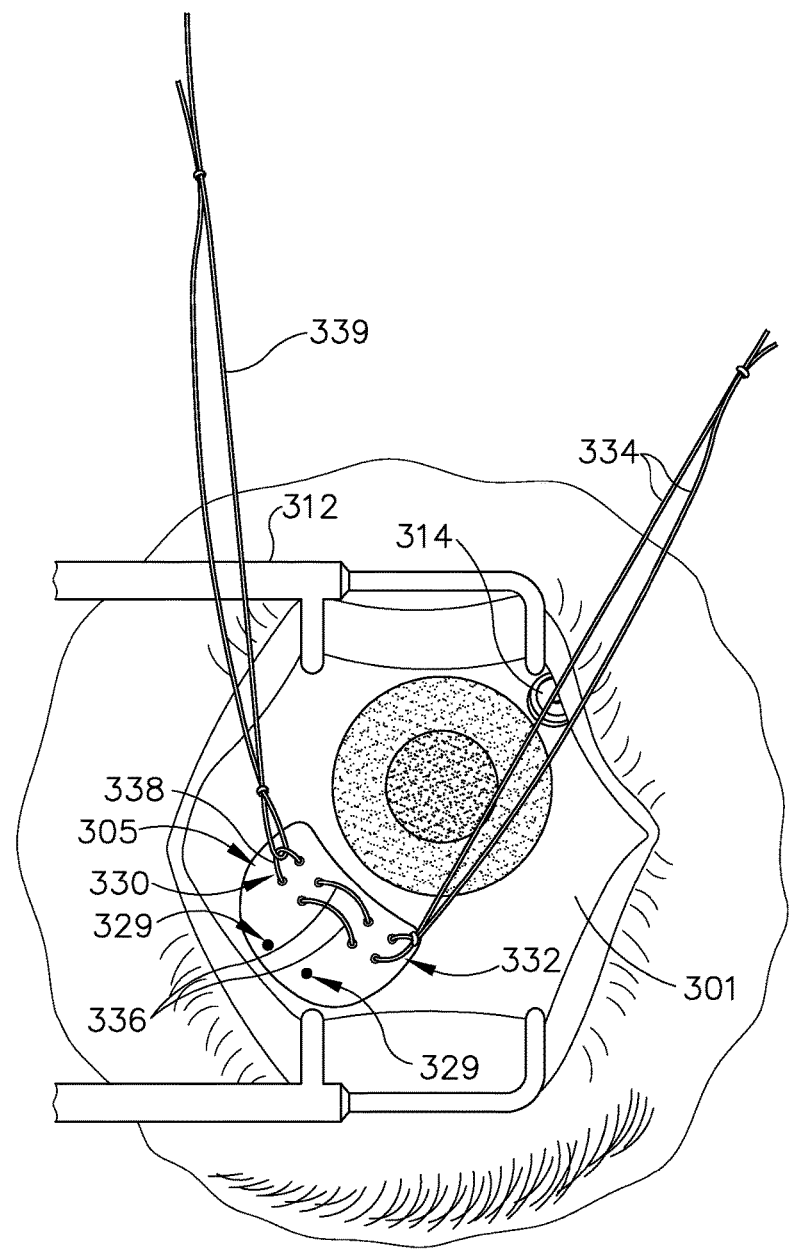
FIG. 9D depicts a top plan view of the eye of FIG. 9A, with a suture loop attached to the eye.
Figure 9E:
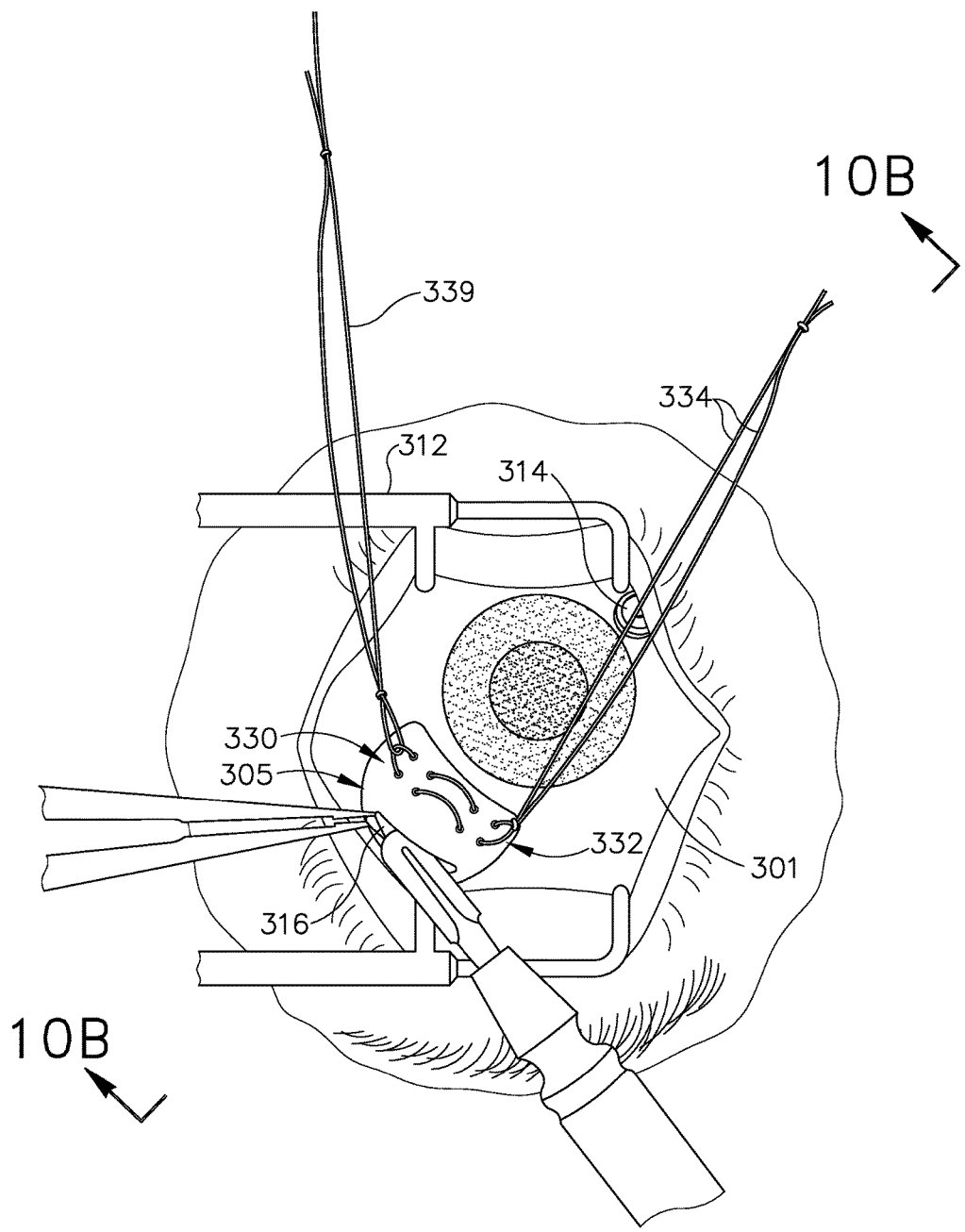
FIG. 9E depicts a top plan view of the eye of FIG. 9A, with a sclerotomy being performed.

FIG. 9D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 9D is described in U.S. patent application Ser. No. 14/619,256, entitled "Method and Apparatus for Suprachoroidal Administration of Therapeutic Agent," filed Feb. 11, 2015, the disclosure of which is incorporated by reference herein. Once suture loop assembly (330) has been attached to eye (301), a sclerotomy may be performed on eye (301). As seen in FIG. 9E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 10B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 9F:
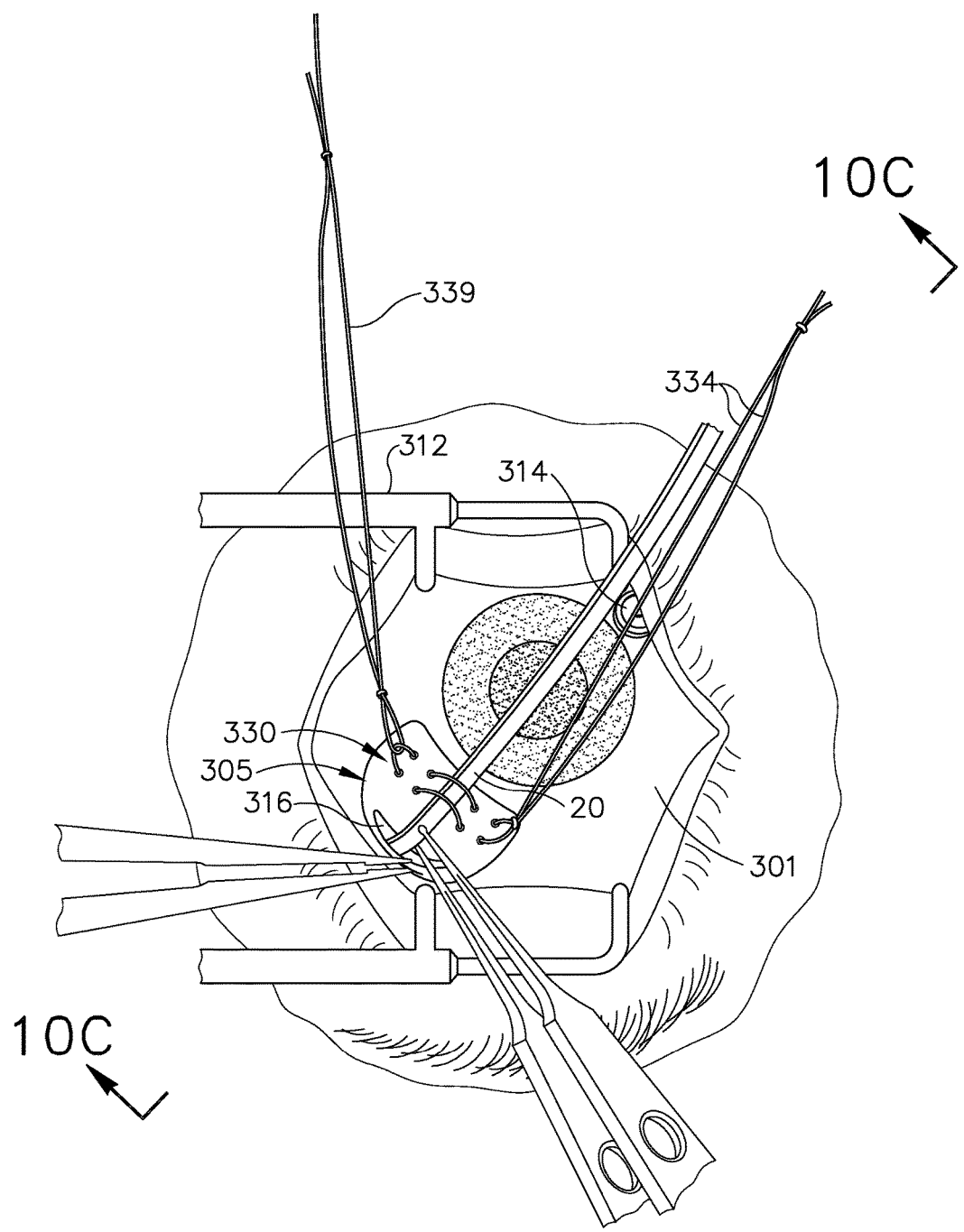
FIG. 9F depicts a top plan view of the eye of FIG. 9A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 9F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 9G:
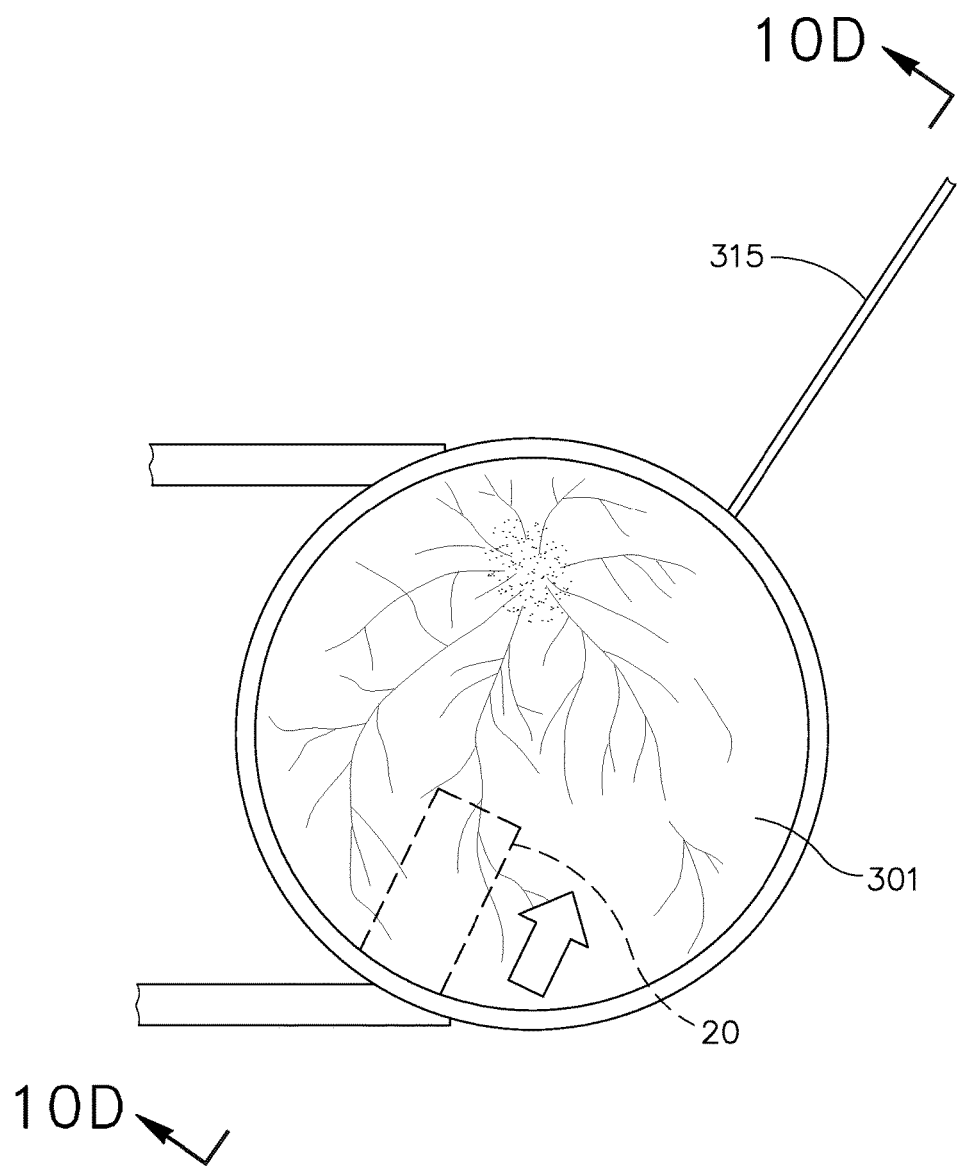
FIG. 9G depicts a top plan view of the eye of FIG. 9A, with the instrument of FIG. 1 under direct visualization at the back of the eye, between the sclera and choroid.
Figure 10C:
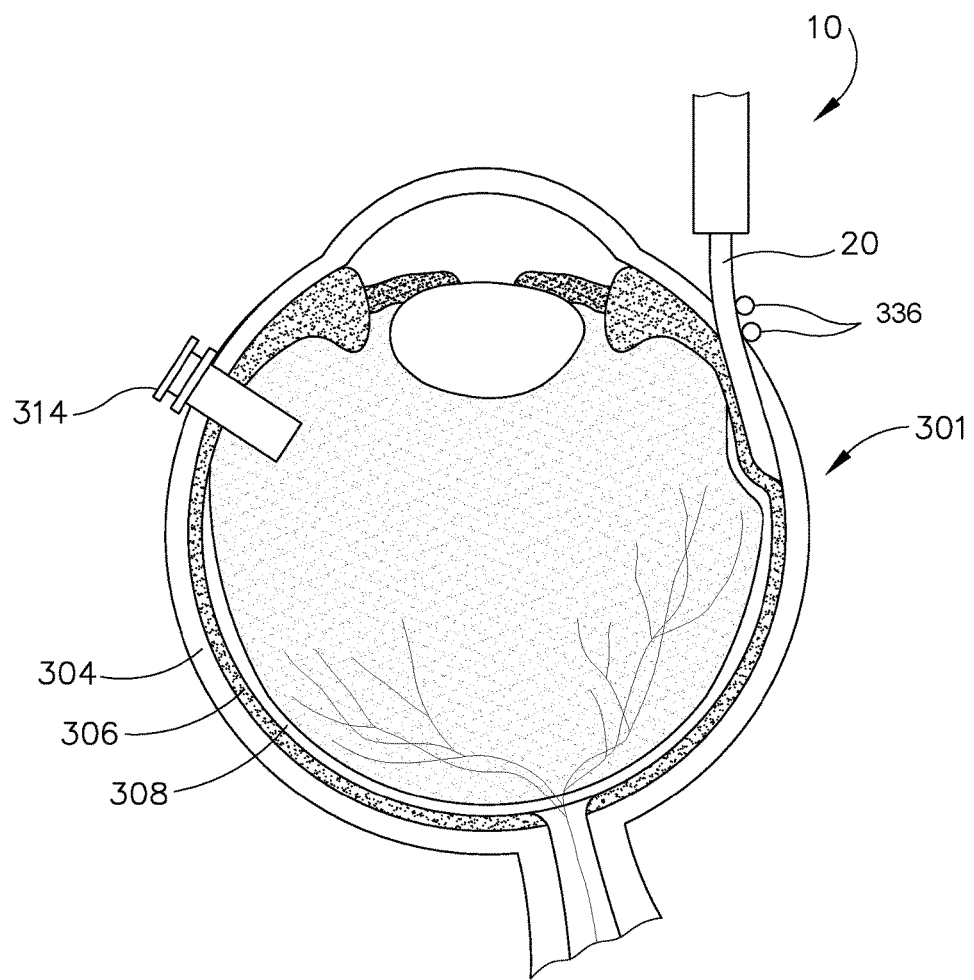
FIG. 10C depicts a cross-sectional view of the eye of FIG. 9A, with the cross-section taken about line 10C-10C of FIG. 9F.
Figure 10D:
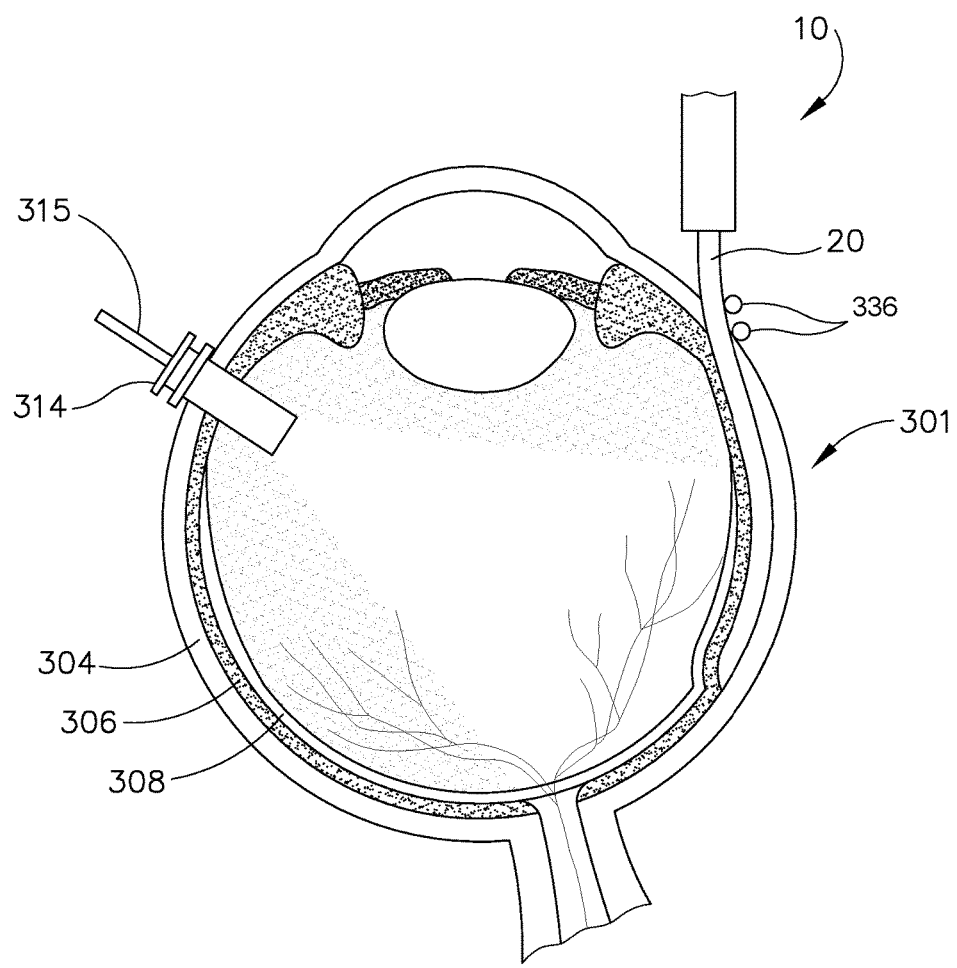
FIG. 10D depicts a cross-sectional view of the eye of FIG. 9A, with the cross-section taken about line 10D-10D of FIG. 9G.
Figure 10E:
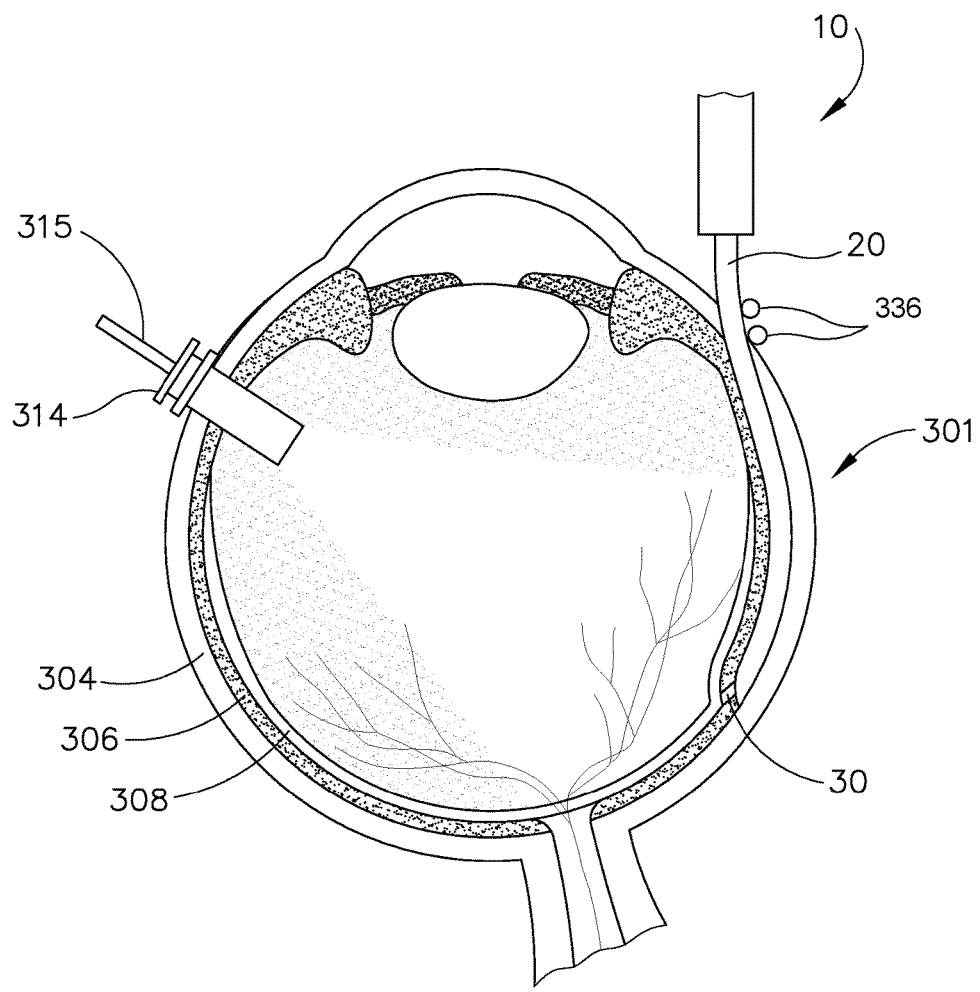
FIG. 10E depicts a cross-sectional view of the eye of FIG. 9A, with the cross-section taken about line 10E-10E of FIG. 9H.

FIGS. 9G and 10C-10D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 9G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 10C to the position shown in 10D. Such tracking may be enhanced in versions where an optical fiber (315) is used to emit visible light through the distal end of cannula (20).

Figure 9H:
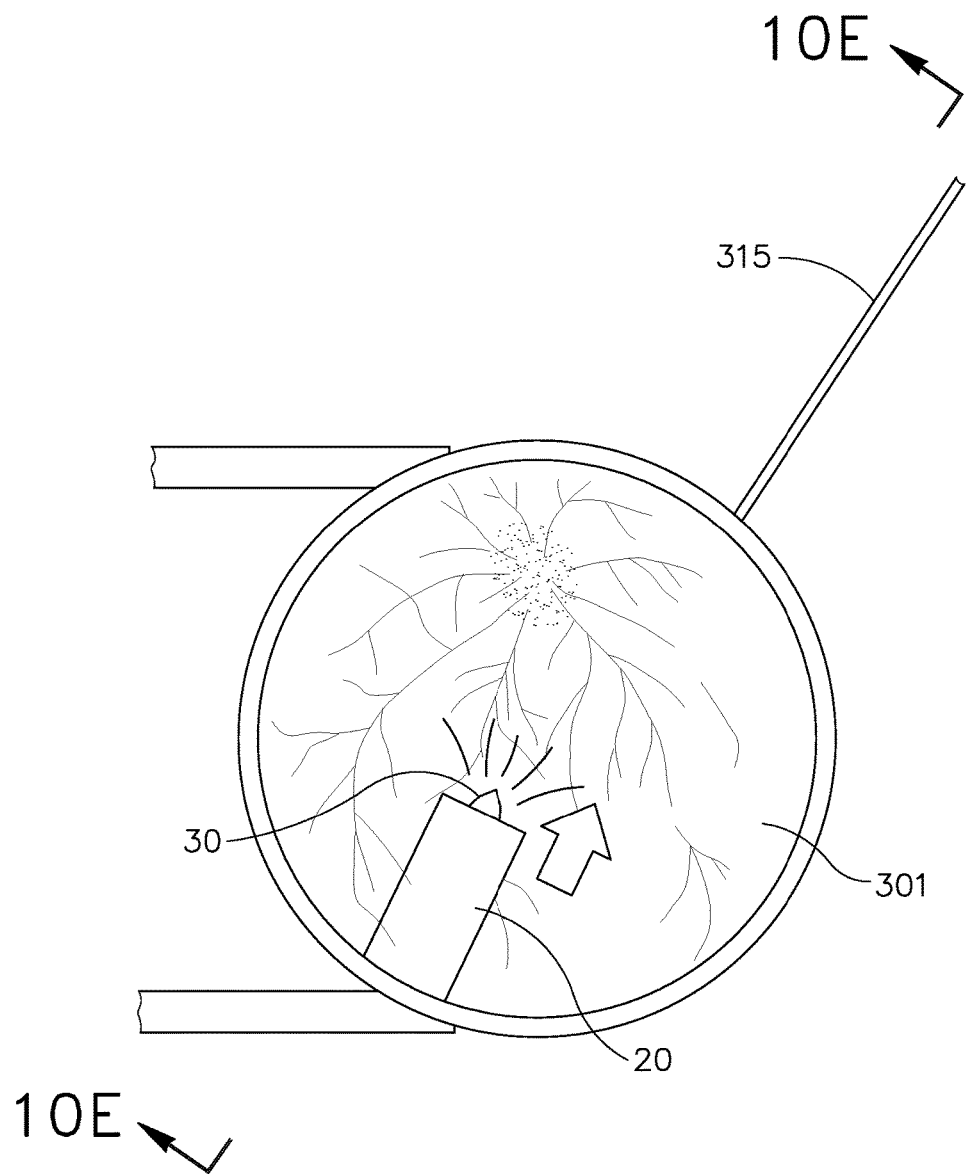
FIG. 9H depicts a top plan view of the eye of FIG. 9A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 10D, an operator may advance needle (30) of instrument (10) as described above with respect to FIGS. 3-4. As can be seen in FIGS. 9H-9I, 10E, and 11A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 9H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 9I:
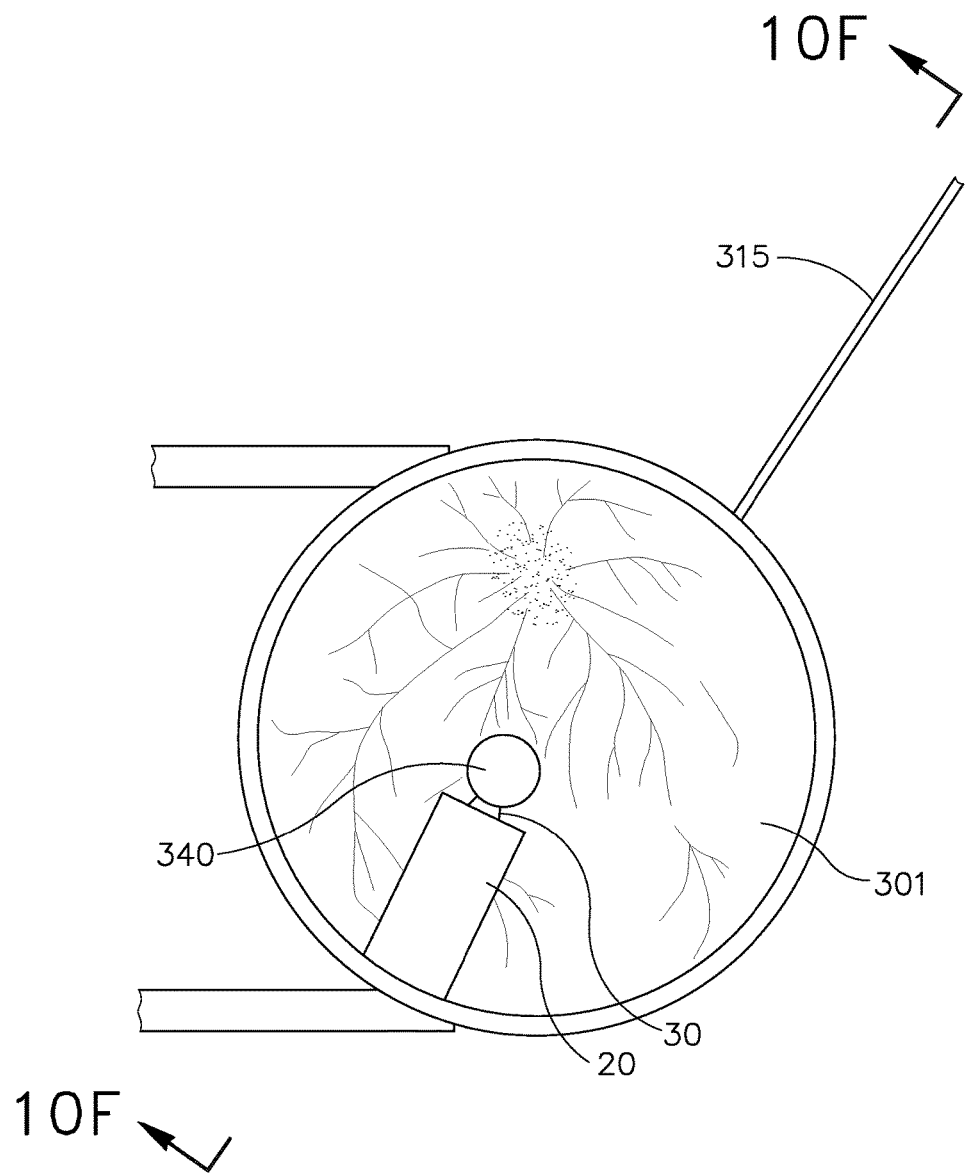
FIG. 9I depicts a top plan view of the eye of FIG. 9A, with the needle dispensing a leading bleb under direct visualization at the back of the eye, the needle between the sclera and choroid, and the leading bleb in the sub retinal space between the choroid and a retina.
Figure 10F:
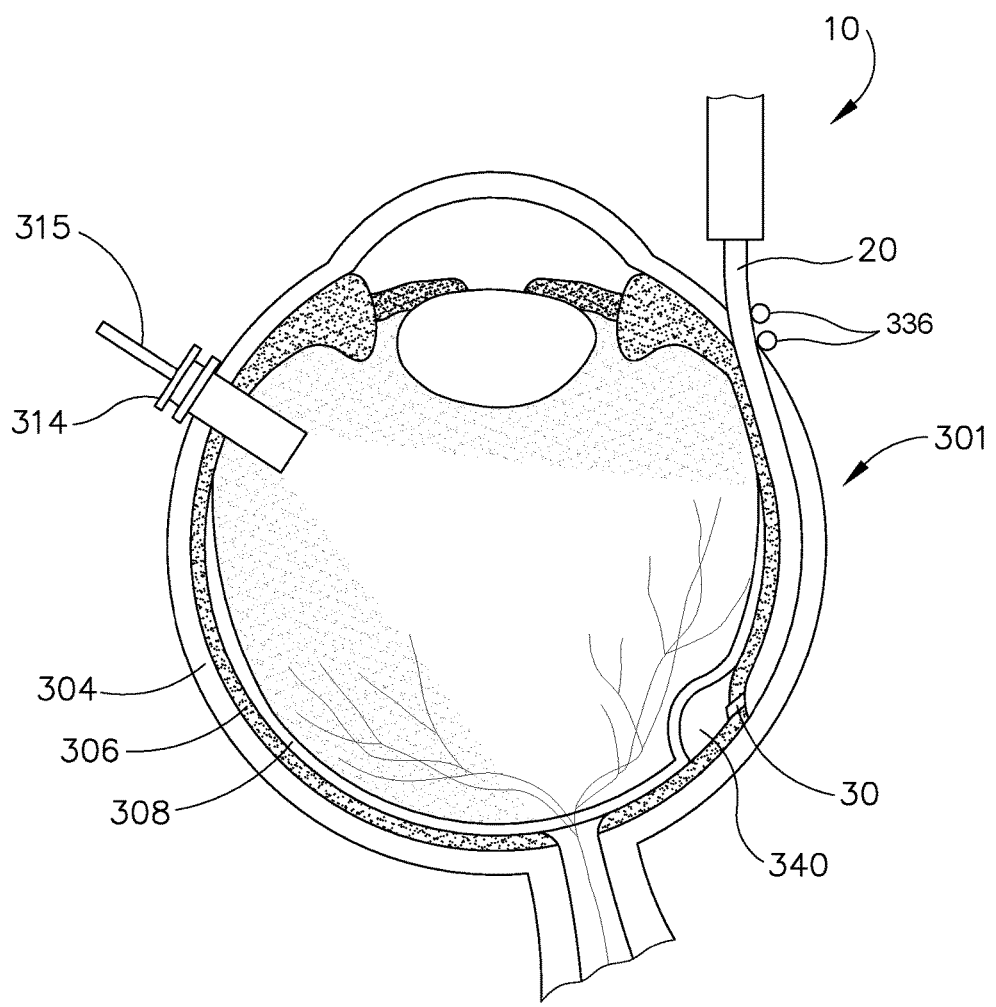
FIG. 10F depicts a cross-sectional view of the eye of FIG. 9A, with the cross-section taken about line 10E-10F of FIG. 9I.
Figure 11A:
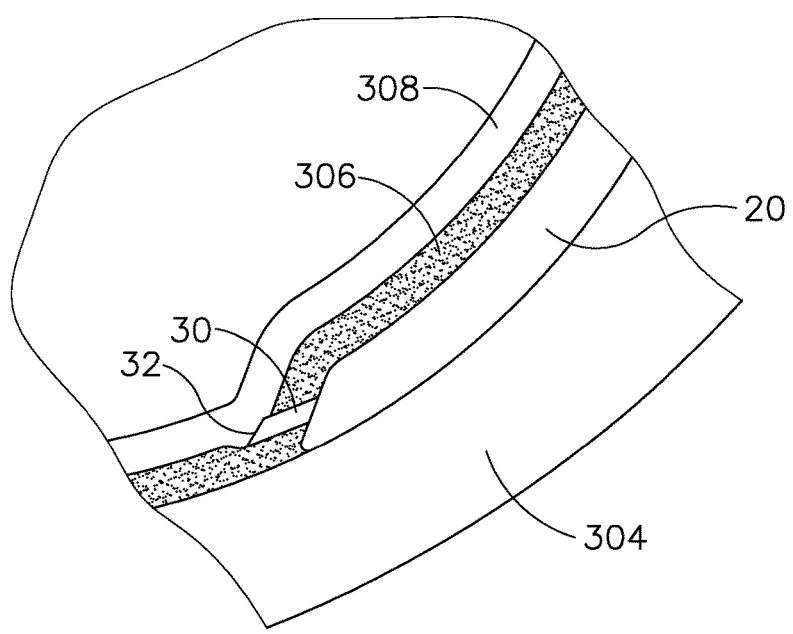
FIG. 11A depicts a detailed cross-sectional view of the eye of FIG. 9A depicted in the state shown in FIG. 10E.
Figure 11B:
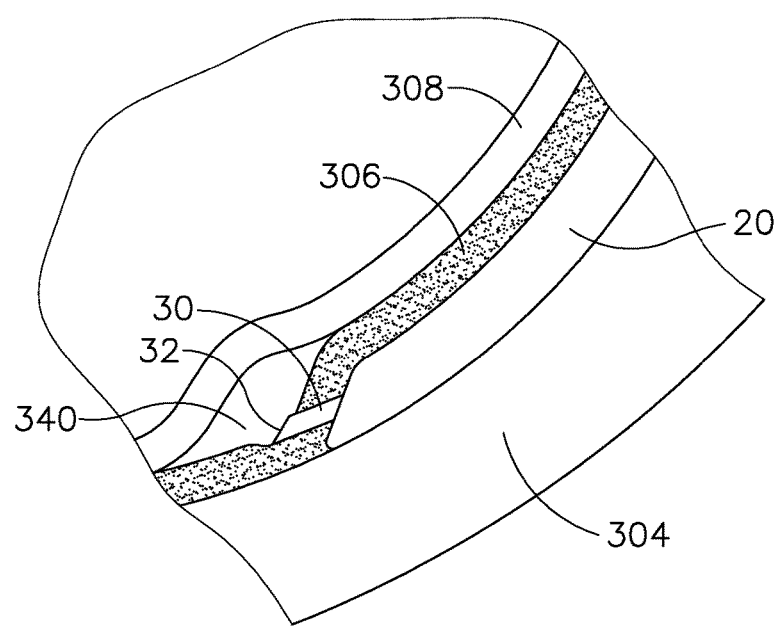
FIG. 11B depicts a detailed cross-sectional view of the eye of FIG. 9A depicted in the state shown in FIG. 10F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 9I, 10F, and 11B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 10F and 11B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 9I, 10F, and 11B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 9J:
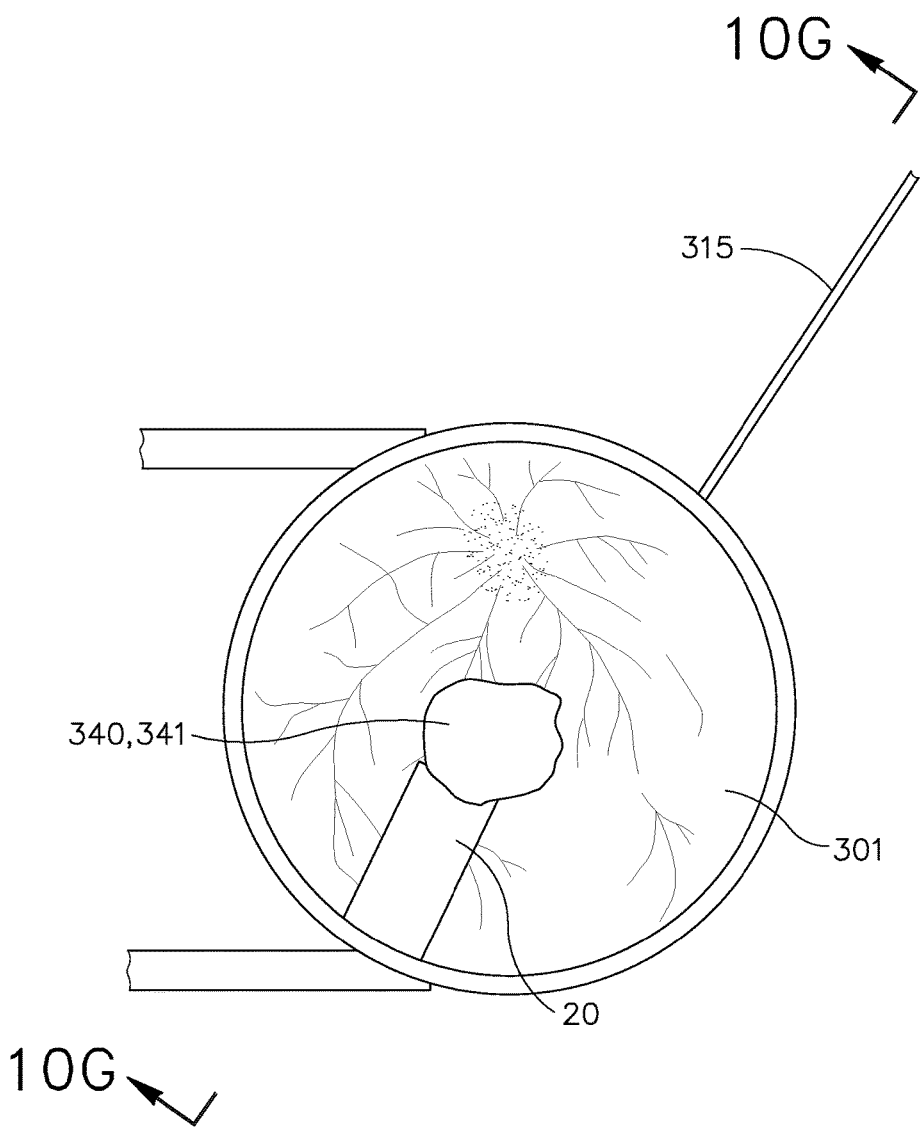
FIG. 9J depicts a top plan view of the eye of FIG. 9A, with the needle dispensing a therapeutic agent to the eye at the back of the eye, between the sclera and choroid.
Figure 10G:
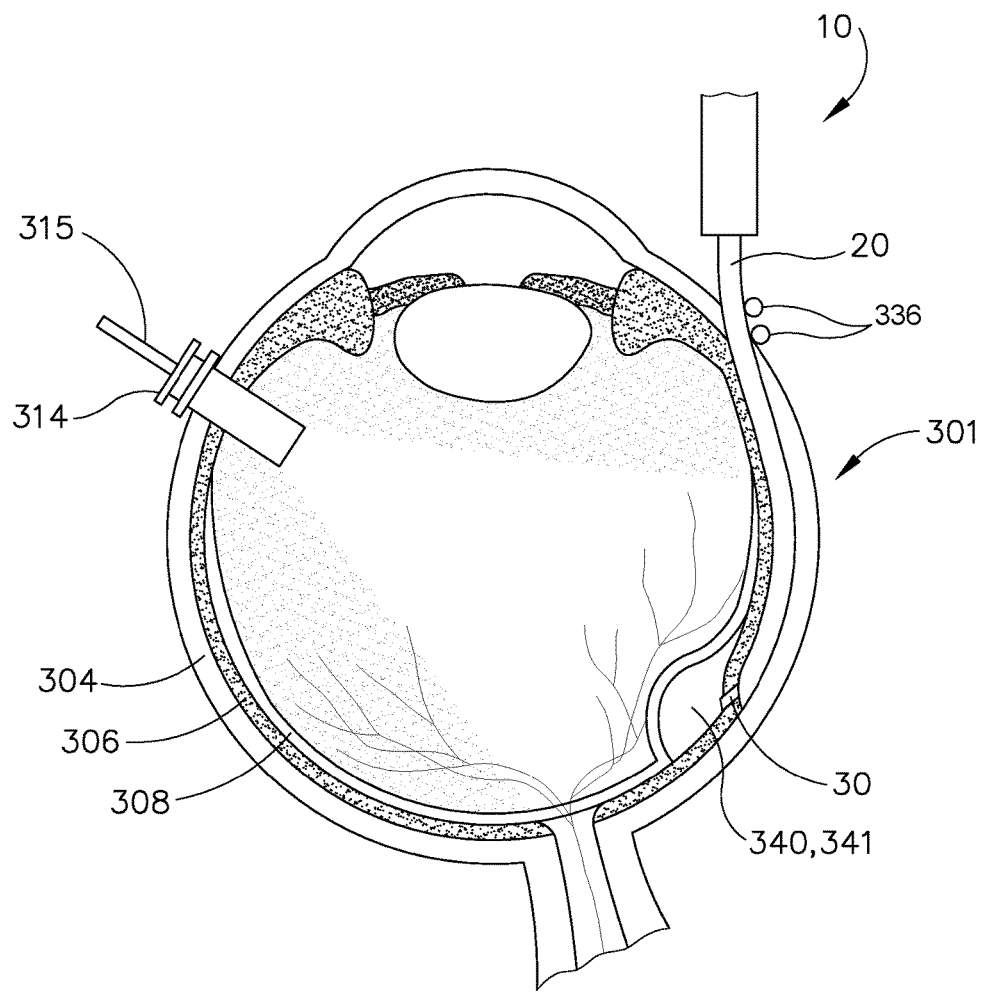
FIG. 10G depicts a cross-sectional view of the eye of FIG. 9A, with the cross-section taken about line 10G-10G of FIG. 9J.
Figure 11C:
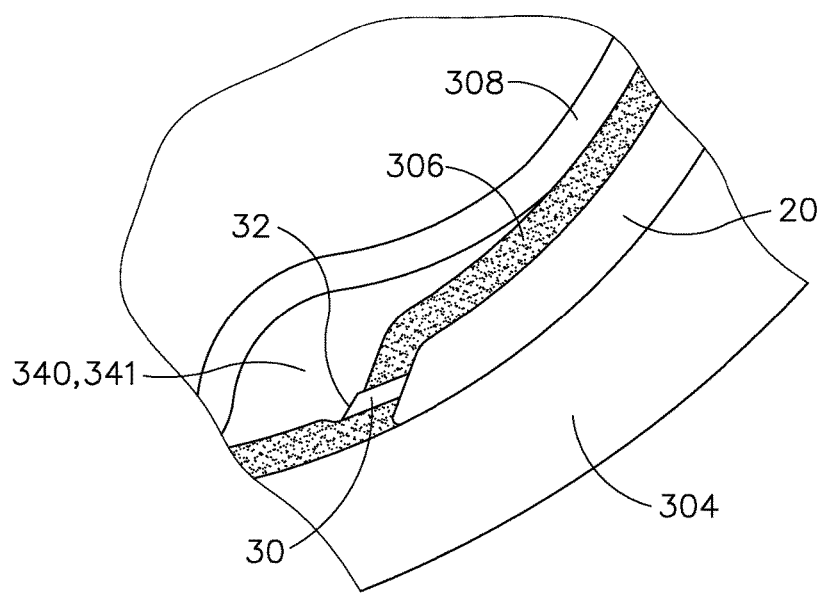
FIG. 11C depicts a detailed cross-sectional view of the eye of FIG. 9A depicted in the state shown in FIG. 10G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent may be visualized by an expansion of the pocket of fluid as can be seen in FIGS. 9J, 10G, and 11C. As shown, therapeutic agent (341) essentially mixes with the fluid of leading bleb (340) as therapeutic agent (341) is injected into the suprachoroidal space.

Once delivery is complete, needle (30) may be retracted by sliding actuation assembly (60) proximally relative to body (40); and cannula (20) may then be withdrawn from eye (301). It should be understood that because of the size of needle (30), the site where needle (30) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (30) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (30) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

V. Exemplary Manual Injection System with Spacer for Controlling Delivered Fluid Volume When providing the delivery of fluid to the subretinal space as described above, it may be desirable to use a fluid delivery instrument that delivers the fluid in a precise manner. This would include fully purging all air from the fluid delivery system and ensuring that a precise amount of fluid is delivered on a consistent basis. This may eliminate the need for the physician to rely on their own judgment or skills to ensure that an appropriate amount of fluid is precisely delivered on a consistent basis. Otherwise, it may be particularly difficult for the physician to rely on their own judgment or skills when a relatively small amount of fluid needs to be delivered to the subretinal space, where delivery of too much fluid may have an adverse effect on the patient.

FIGS. 12A-15B show some components of a system that may be used to store and deliver predetermined amount of fluids, such as bleb (340) fluid and therapeutic agent (341) fluid as described above, to a subretinal space in a precise and consistent manner via an instrument (e.g., instrument (10, 2010)). As discussed in more detail below, this system may be fluidly coupled with an instrument (1000), which may be configured and operable just like instrument (10, 2010) described above. Alternatively, instrument (1000) may take any other suitable form. As shown, the system of the present example includes a syringe (402) and a measurement tab (404) that is configured to engage syringe (402) and act as a stop or spacer to prevent a syringe plunger assembly (406) from advancing past a particular position relative to a syringe barrel (408).

As shown in FIGS. 12A-14B, syringe (402) of the present example comprises barrel (408) having a distal end (410) and a proximal end (412). Distal end (410) includes a first, dispensing opening (414) and a threaded portion (416) that enables coupling of the syringe (402) to a needle, tubing, etc. In some versions, threaded portion (416) comprises a conventional luer fitting. Proximal end (412) includes a second opening (418) that is configured to receive syringe plunger assembly (406). Lumen (420) extends between the first and second openings (414, 418) and includes a first portion that is configured to receive the syringe piston (434) and plunger rod (436), and a second, decreased cross-sectional dimension portion at the proximal end (412).

Proximal end (412) of syringe barrel (408) comprises a flange (422) that extends radially outwardly relative to a longitudinal axis (424) of syringe (402) and acts as a finger grip when a user holds syringe (402). As shown best in FIGS. 15A-15B, flange (422) includes two parallel opposing flat edges (426a, 426b) and two opposing curved edges (428a, 428b) that each extend between the flat edges (426a, 426b). Curved edges (428a, 428b) extend around axis (424). Flange (422) further includes a proximal side (430) facing away from barrel (408) and a distal side (432) facing toward barrel (408).

Figure 13A:
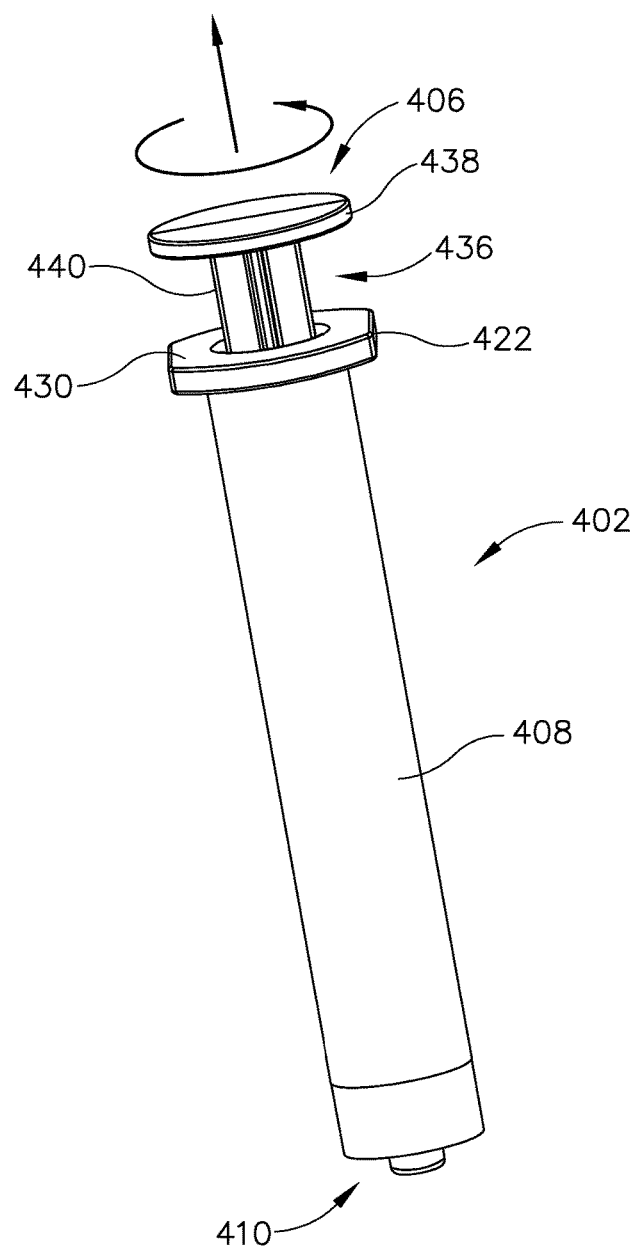
FIG. 13A depicts a perspective view of the syringe of the syringe assembly of FIG. 12A, showing the plunger rod of the plunger assembly being rotated relative to the barrel.
Figure 13B:
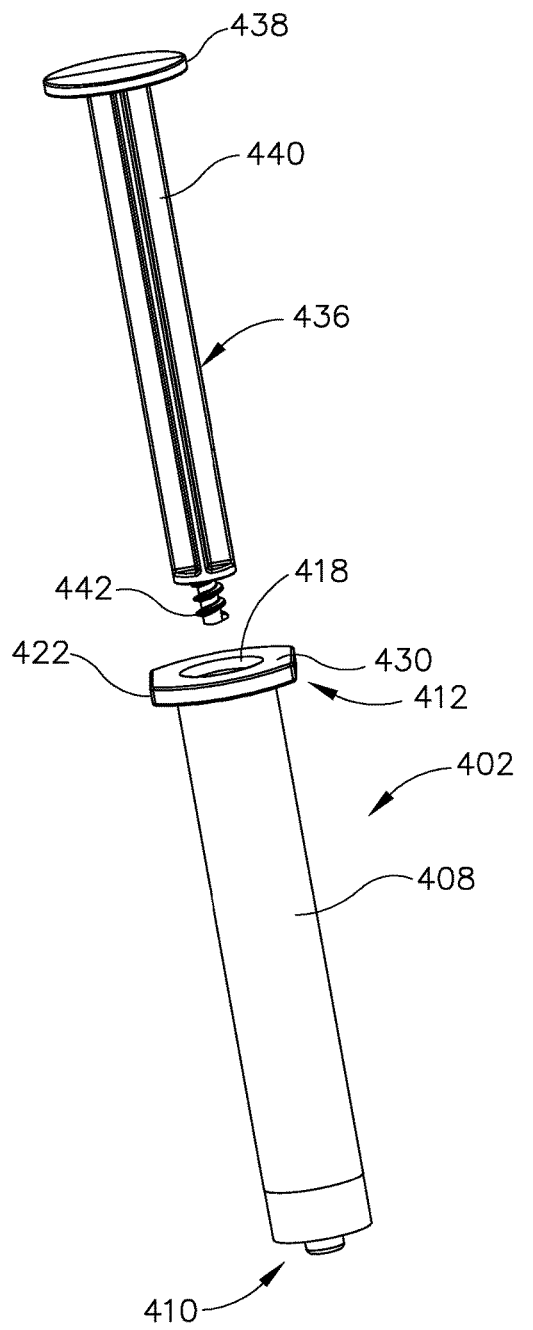
FIG. 13B depicts a perspective view of the syringe of FIG. 12A, with the plunger rod having been removed from the barrel.
Figure 14A:
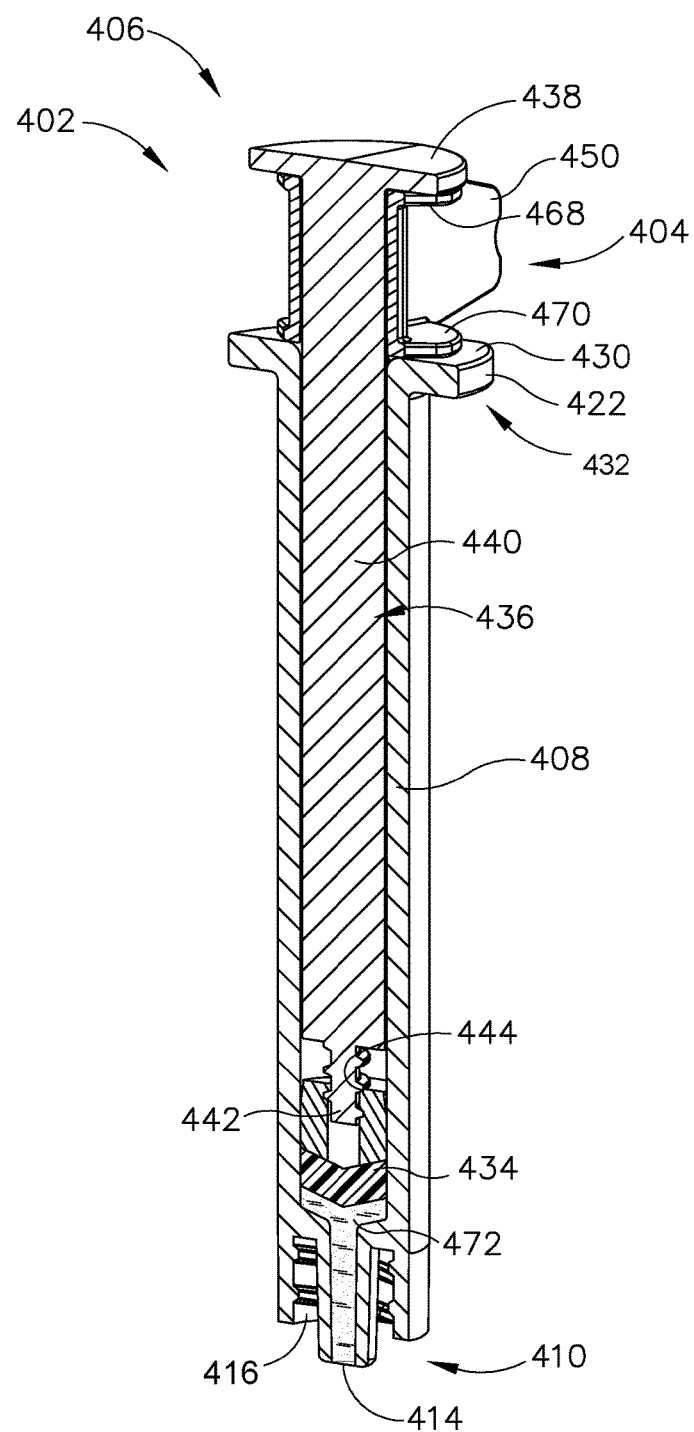
FIG. 14A depicts a side cross-sectional perspective view of the syringe assembly of FIG. 12A.

As best seen in FIGS. 13B and 14A, plunger assembly (406) of the present example comprises a piston (434) and a plunger rod (436) that includes a thumb flange (438) and a shaft (440). In the present example, piston (434) and plunger rod (436) are removably coupled to one another. More particularly, plunger rod (436) includes a threaded portion (442), and piston (434) includes a threaded portion (444) that is configured to receive and threadably engage threaded portion (442) of plunger rod (436). Thus, piston (434) may be advanced and retracted within lumen (420) by advancing and retracting plunger rod (436) when piston (434) is coupled thereto. Alternatively, as discussed in more detail below, when plunger rod (436) is no longer coupled to piston (434), piston (434) may be advanced and retracted by fluidly coupling lumen (420) with a source of pressurized air, as discussed in further detail below.

Figure 15A:
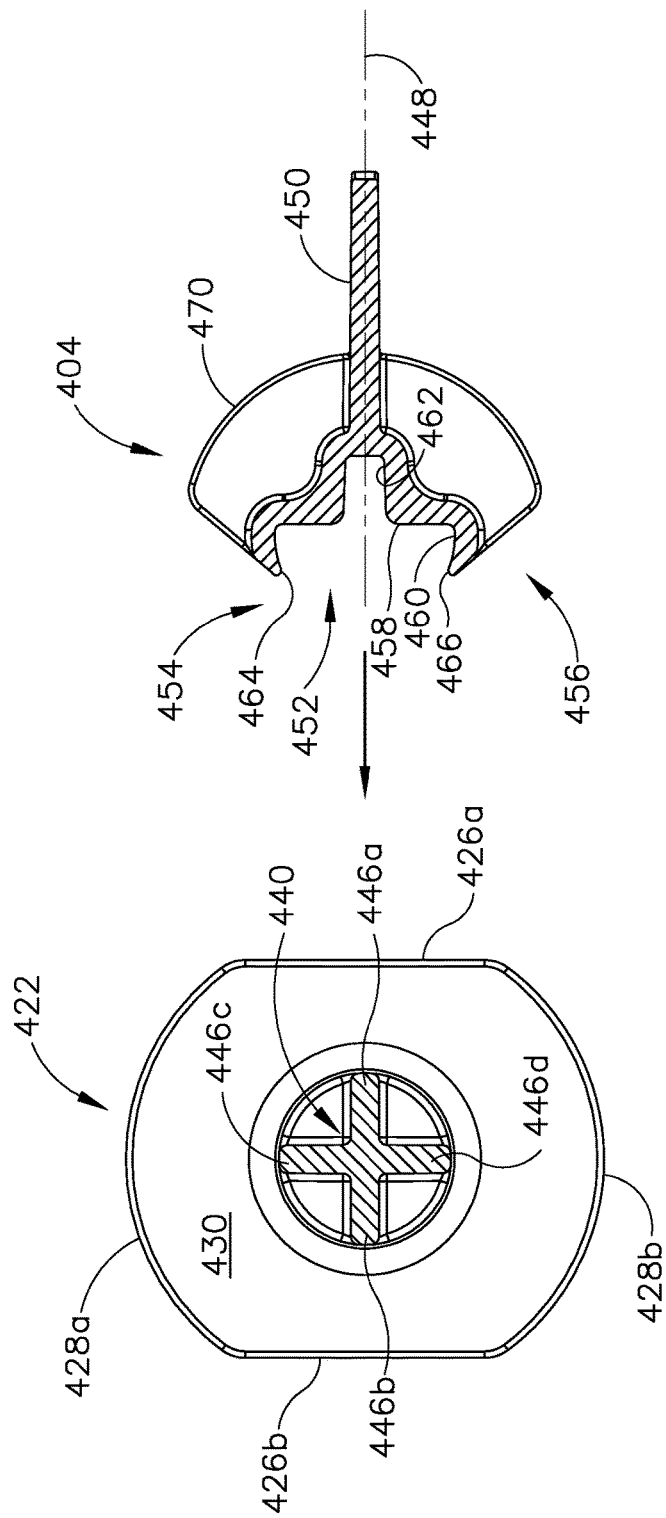
FIG. 15A depicts a top cross-sectional view of the syringe assembly of FIG. 12A, with the measurement tab laterally separated from the plunger rod.
Figure 15B:
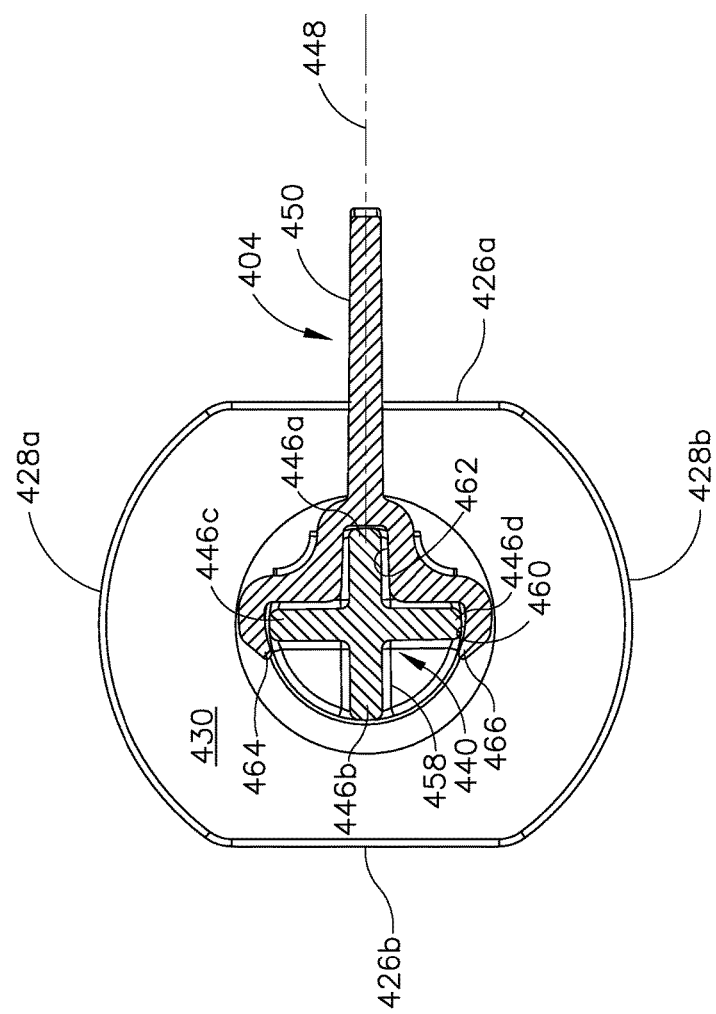
FIG. 15B depicts a top cross-sectional view of the syringe assembly of FIG. 12A, with the measurement tab laterally secured to the plunger rod.

As shown best in FIGS. 15A-15B, a portion of shaft (440) includes a cross-section defined by equal length perpendicular members that cross at their midpoints (i.e., like a "+" sign), such that shaft (440) defines a first arm (446a), a second arm (446b) opposing the first arm (446a), a third arm (446c) extending perpendicular to the first and second arms (446a-b), and a fourth arm (446d) opposing the third arm (446c) and extending perpendicular to the first and second arms (446a-b).

As shown best in FIGS. 12A-12C, 14A, and 15A-15B, tab (404) includes a grip portion (450) that extends along an imaginary plane (448) (FIG. 15A) and that is configured to be grasped by an operator. Tab (404) further includes an engagement portion (452) that is configured to releasably engage shaft (440) of syringe (402). In the present example, engagement portion (452) includes a first side (454), a second side (456), and a recess (458) defined between the first and second sides (454, 456). As shown, at least a portion of recess (458) defines a shape that complements at least a portion of the shape of the shaft (440), such that recess (458) is configured to receive at least a portion of shaft (440). Particularly, recess (458) defines part of a cross shape having a first recessed portion (460) that extends perpendicularly to plane (448); and a second recessed portion (462) that extends perpendicularly from the first recessed portion (460) toward handle (450) and along plane (448). Engagement portion (452) defines a first lip (464) on the first side (454) extending inwardly toward plane (448) and a second lip (466) on second side (456) extending inwardly towards plane (448). Tab (404) further includes an upper flange (468) and lower flange (470) on each end of the handle (450). Flanges (468, 470) each extend along planes that are parallel to each other and that are perpendicular to plane (448). Various other suitable ways in which tab (404) may be configured will be apparent to a person skilled in the art in view of the teachings herein.

In order to direct tab (404) into engagement with shaft (440), an operator may grasp handle (450) and direct engagement portion (452) toward shaft (440). Lips (464, 466) initially contact the third and fourth arms (446c, 446d) of shaft (440), respectively and cause the first and second sides (454, 456) of tab to flex away from one another such that each side (454, 456) flexes outwardly away from plane (448). Eventually, lips (464, 466) cam back along third and fourth arms (446c, 446d) such that the first and second sides (454, 456) move back inwardly toward plane (448). Lips (464, 466) and first recessed portion (460) receive third and fourth arms (446c, 446d) and second recessed portion (462) receives first arm (446a). Tab (404) thus provides a releasable snap fit with shaft (440) in the present example. Of course, tab (404) may be directed into engagement with shaft (440) such that engagement portion (452) engages shaft (440) in a different manner, e.g., such that engagement portion (452) engages a different set of arms (446a-d). Other suitable ways in which tab (404) may couple shaft (440) will be apparent to persons skilled in the art in view of the teachings herein.

In the present example, once tab (404) engages shaft (440), the operator may adjust tab (404) such that the bottom flange (470) abuts flange (422) of syringe (402). Alternatively, the operator may place tab (404) into engagement with shaft (440) such that upper flange (468) of tab generally abuts thumb flange (438). As another merely illustrative example, the operator may place tab (404) into engagement with shaft (440) at an intermediate position along shaft between flange (422) and thumb flange (438). In the present example, tab (404) is configured to engage shaft (440) in a manner that allows tab to slide relative to shaft (440) and that allows shaft (440) to slide relative to tab (404). Tab (404) is further configured such that when the plunger rod (436) is advanced relative to barrel (408), thumb flange (438) is prevented from advancing further when thumb flange (438) abuts upper flange (468) and lower flange (470) abuts flange (422) of syringe (402). Tab (404) thus restricts distal advancement of plunger assembly (406) relative to barrel (408).

In the example where the initial position of tab (404) is such that lower flange (470) of tab (404) abuts flange (422) of syringe (402), thumb flange (438) eventually bottoms out against upper flange (468) of tab (404) as plunger assembly (406) is advanced distally relative to barrel (408). In the example where the initial position of tab (404) is such that the upper flange (468) of tab (404) abuts thumb flange (438), lower flange of tab (404) eventually bottoms out against flange (422) of syringe (402) as plunger assembly (406) is advanced distally relative to barrel (408). In the example where the initial position of tab (404) is such that tab (404) is placed in an intermediate position between thumb flange (438) and flange (422) of syringe (402), tab (404) initially moves with shaft (440) as shaft (440) is advanced distally until lower flange (470) of tab (404) abuts flange (422) of syringe (402). As the operator continues to advance the syringe (402), thumb flange (438) bottoms out against upper flange (468) of tab (404). Regardless of the initial engagement position of tab (404) relative to shaft (440), in the present example, tab (404) may be sized and configured to ensure that a predetermined amount of fluid (472) remains in syringe (402) once plunger is advanced relative to tab (404) such that thumb flange (438) abuts upper flange of tab (404), and lower flange of tab (404) abuts flange of syringe (402).

Tab (404) may be removed from engagement with shaft (440) by, for example, the operator pulling tab (404) away from shaft along a path that is transverse to the longitudinal axis of shaft (440), with a sufficient force to overcome the engagement between engagement portion (452) and shaft (440). Absent the force, engagement portion (452) is configured to maintain the engagement between tab (404) and shaft (440). Upon being subjected to such a removal force, however, in the present example, lips (464, 466) cam against third and fourth arms (446c, 446d), respectively, and first and second sides (454, 456) are urged away from plane (448). As the operator continues to move tab (404) away from shaft (440), lips (464, 466) eventually disengage from third and fourth arms (446c, 446d), and first and second sides (454, 456) flex back inwardly toward plane (448) and toward one another. In some alternative examples, tab (404) includes features that may be manipulated to facilitate release of shaft (440) by engagement portion (452). For instance, tab (404) may include features that the operator pinches toward each other in order to make engagement portion (452) immediately release shaft (440). Various suitable features that may be incorporated into tab (404) in order to facilitate release of shaft (440) by engagement portion (452) will be apparent to those of ordinary skill in the art in view of the teachings herein.

Figure 12B:
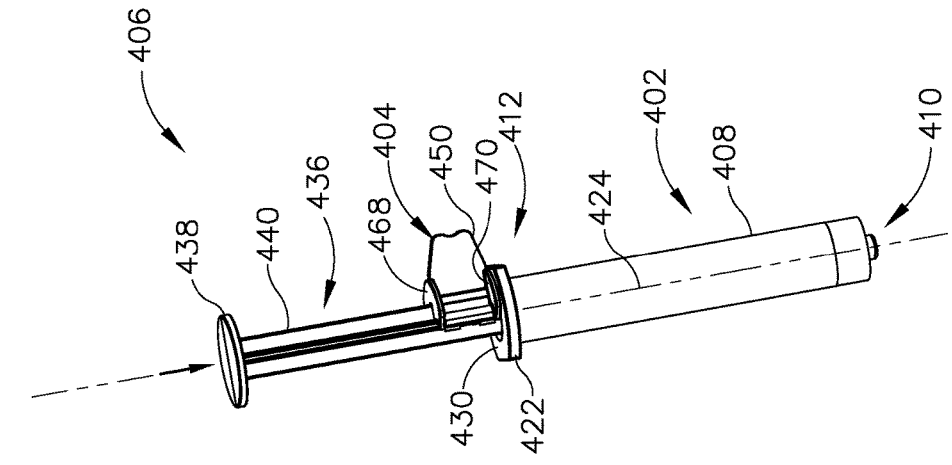
FIG. 12B depicts a perspective view of the syringe assembly of FIG. 12A, with the measurement tab of the syringe assembly engaged with a plunger of the syringe.
Figure 12A:
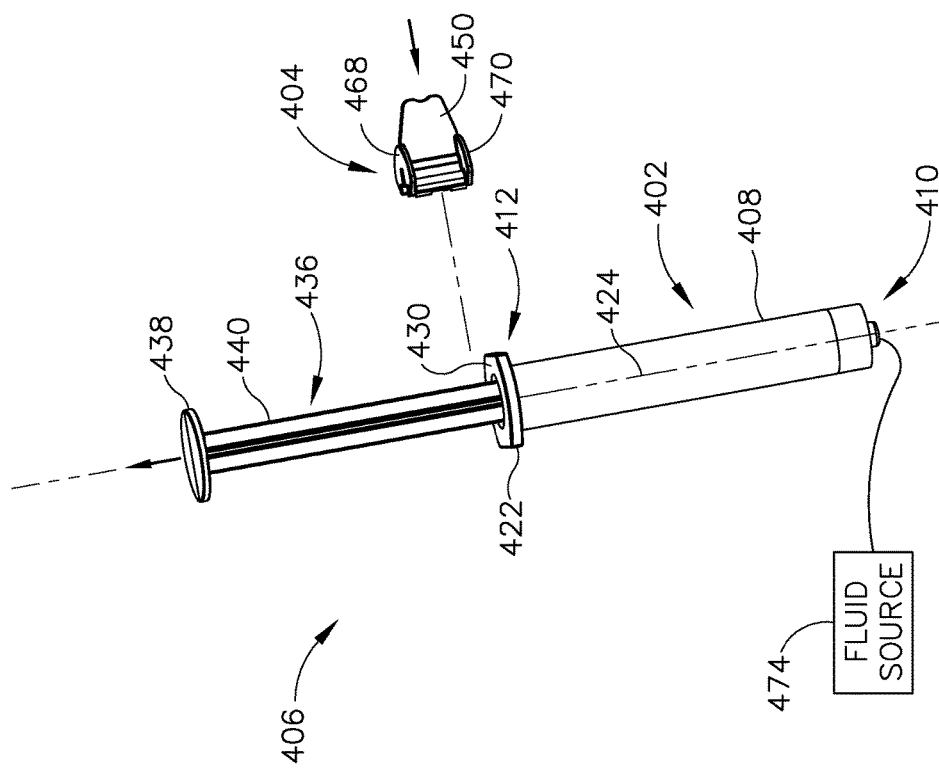
FIG. 12A depicts an exemplary syringe assembly that may be used with the instruments of FIGS. 1 and 7, with a syringe of the syringe assembly drawing fluid from a fluid source.

In an exemplary use as shown in FIG. 12A, an operator may couple barrel (408) with a fluid source (474) and then draw fluid into syringe (402) from fluid source (474) by retracting plunger rod assembly (406) relative to barrel (408) (e.g. manually or mechanically). The operator may then secure tab (404) to shaft (440) and decouple fluid source (474) from syringe (402) as shown in FIG. 12B. While tab (404) is secured to shaft (440) after fluid is drawn into syringe (402) in this example, it should be understood that tab (404) may alternatively be engaged with shaft (440) before fluid is drawn into syringe (402) or while fluid is being drawn into syringe (402).

Once fluid has been drawn into syringe (402), fluid source (474) has been decoupled from syringe, and tab (404) has been secured to shaft (440), the operator may push plunger assembly (406) distally relative to barrel (408). For at least a first part of this advancement, the operator may orient syringe (402) upwardly such that any air in lumen (420) will be positioned at distal end (410). Thus, piston (434) will first purge the air out of the space in lumen (420) defined between piston (434) and distal end (410) as plunger assembly (406) is distally advanced through a first range of motion. As the operator continues to advance plunger assembly (406), some fluid may be ejected out through opening (414). Plunger assembly (406) will eventually reach the state shown in FIG. 12C, where tab (404) is engaged with both flange (422) of syringe (402) and thumb flange (438) of plunger rod (436). Tab (404) thus arrests further advancement of plunger assembly (406) relative to barrel (408) at this stage. It should be understood that this will consistently result in a fixed, predetermined amount of fluid in barrel (408). The amount of fluid will be based on the separation distance between flanges (468, 470).

As also shown in FIG. 12C, once thumb flange (438) has bottomed out against tab (404), the operator may couple distal end (410) with a fluid delivery instrument (1000) via any suitable conduit (e.g., flexible tube, etc.). By way of example only, instrument (1000) may be constructed and operable just like either instrument (10, 2010) described above. It should therefore be understood that syringe (402) and plunger assembly (406) may be used to deliver bleb (340) and/or therapeutic agent (341) fluid as described above. Alternatively, instrument (1000) may have any other suitable configuration and may be configured for use in any suitable procedure calling for delivery of a predetermined amount of fluid. It should also be understood that syringe (402) and plunger assembly (406) may be used to deliver any suitable kind of fluid. Various suitable fluids, instruments, and medical procedures that may be associated with syringe (402), plunger assembly (406), and tab (404) will be apparent to those of ordinary skill in the art in view of the teaching herein.

Figure 12E:
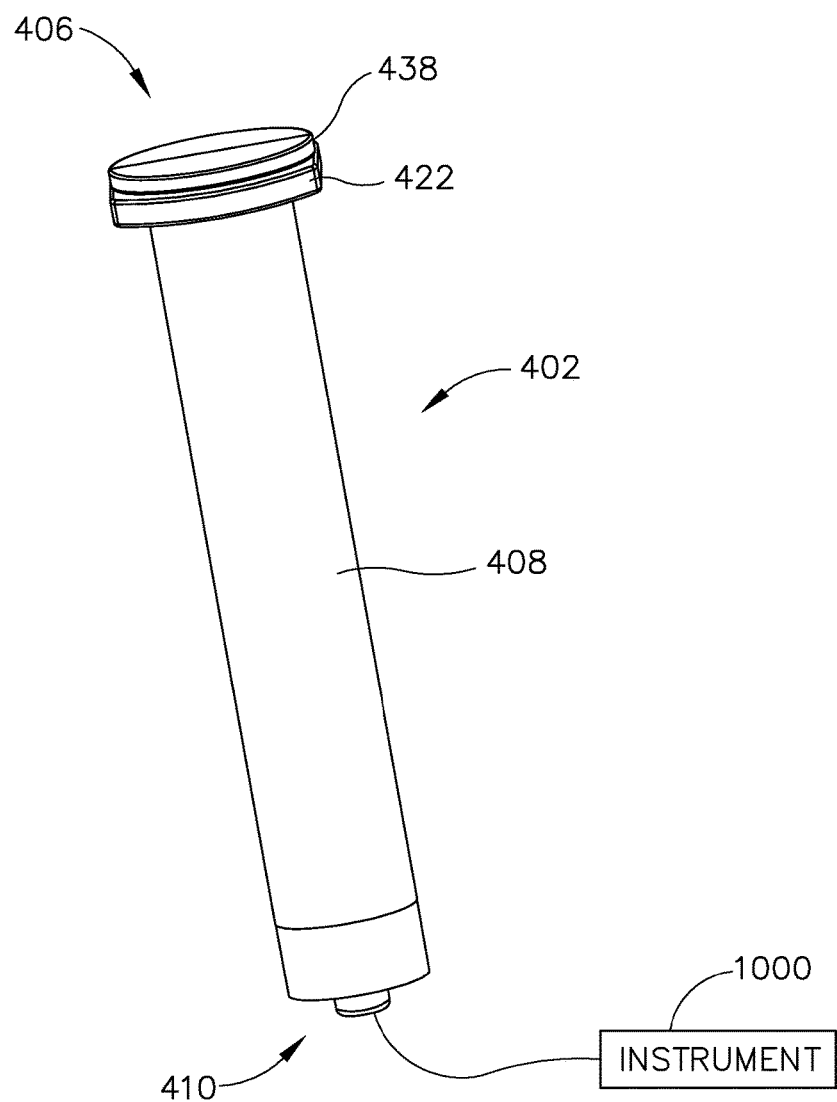
FIG. 12E depicts a perspective view of the syringe of FIG. 12A, with the plunger assembly having been advanced distally to dispense the contents of the syringe to the instrument.

After reaching the state shown in FIG. 12C, once instrument (1000) is positioned for delivery of fluid at an appropriate location, the operator may remove tab (404) from shaft (440) as shown in FIG. 12D. The operator may remove tab (404) from shaft (440) by grasping grip (450) and thereby pulling on tab (404) with a force sufficient to disengage engagement portion (452) from shaft (440), as discussed above. Tab (404) may remain on shaft (440) up until instrument (1000) has reached the appropriate location for fluid delivery. In some alternative versions, tab (404) is removed from shaft (440) before distal end (410) is coupled with instrument (1000). Once tab (404) is removed from shaft (440), the operator may advance plunger assembly (406) fully distally until thumb flange (438) bottoms out against flange (422) as shown in FIG. 12E. At this stage, piston (434) has been pressed to the distal end of lumen (420) such that the entire predetermined volume will have been expelled through distal end (410) to instrument (1000).

VI. Exemplary Adapters for Syringes to Couple with Powered Injection System

In some instances, it may be desirable to use one or more powered components (e.g., a pump, etc.) to deliver bleb fluid (340), therapeutic agent (341), etc., instead of relying on the operator to deliver such fluid manually by pressing on plunger assembly (406). It may therefore be desirable to modify syringe (402) to enable the modified version of syringe (402) to be used in a system that uses one or more powered components (e.g., a pump, etc.) to deliver bleb fluid (340), therapeutic agent (341), etc.

Figure 13C:
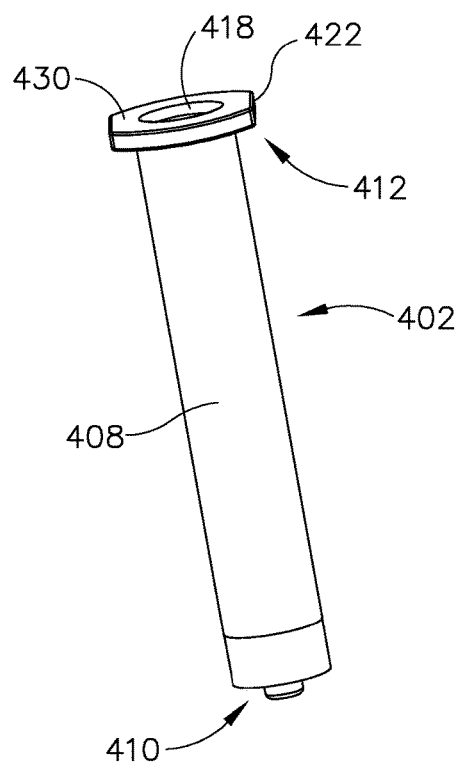
FIG. 13C depicts a perspective view of the barrel of the syringe of FIG. 12A.
Figure 14B:
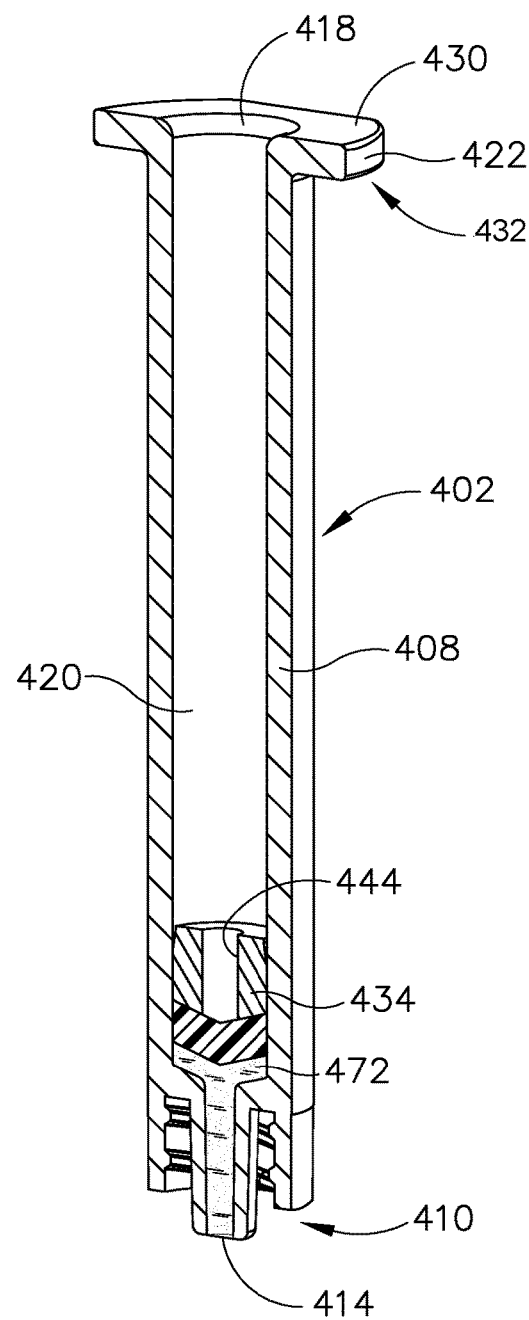
FIG. 14B depicts a side cross-sectional perspective view of the syringe of FIG. 12A, with the plunger rod having been removed from the barrel.

FIGS. 13A-14B show an exemplary alternative method of using syringe (402) and plunger assembly (406), to prepare syringe (402) for use in a system with one or more powered components as described in greater detail below. This method is substantially similar to the method described above with respect to FIGS. 12A-12E. The method shown in FIGS. 13A-14B begins at after reaching the stage shown in FIG. 12C and described above, where plunger assembly (406) has reached a predetermined depth of advancement into syringe (402), as governed by tab (404), resulting in a predetermined volume of fluid in syringe (402). While not shown in FIGS. 13A-14B, it should be understood that instrument (1000) may be coupled with distal end (410) of syringe (402) during the stages shown in FIGS. 13A-14B. In the present example, instead of the operator advancing plunger assembly (406) further distally in order to expel the fluid from syringe (402), the operator decouples rod (436) from piston (434) by rotating rod (436) to unscrew threaded portion (442) from threaded portion (444). Once rod (436) has been decoupled from piston (434), the operator may fully remove rod (436) from syringe (402) as shown in FIGS. 13B-13C and 14B, then set rod 036) aside. Piston (434) will remain in place in barrel (408), as shown in FIG. 14B. With piston (434) being positioned deeply within lumen (420), barrel (408) may protect piston (434) from inadvertent engagement with other objects, such that piston (434) may remain in the same position within barrel (408) until piston (434) is acted upon by a pressurized medium as will be described in greater detail below. With piston (434) remaining in the same position within barrel (408), the same predetermined amount of fluid may also remain within barrel (408).

Figure 16:
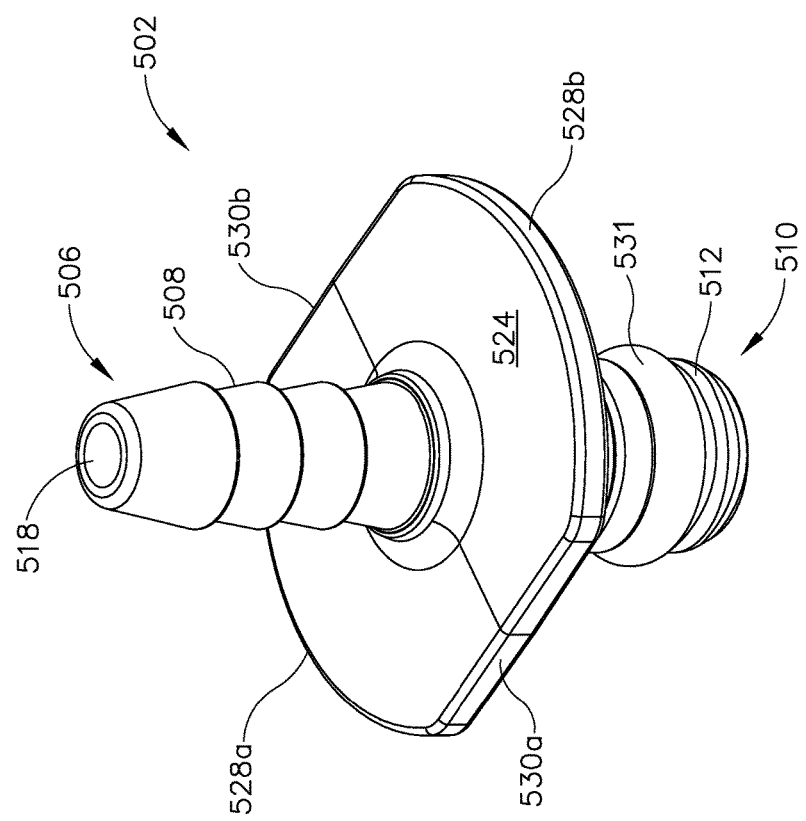
FIG. 16 depicts a perspective view of an exemplary syringe adapter that is configured for use with the syringe of FIG. 12A.
Figure 17:
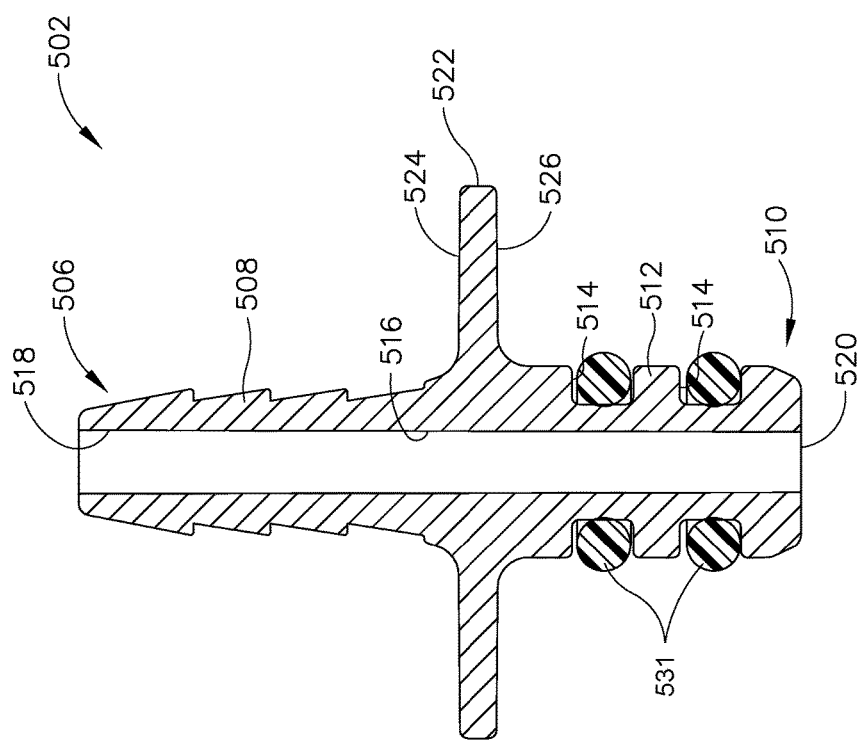
FIG. 17 depicts a side cross-sectional view of the syringe adapter of FIG. 16.

FIGS. 20A-21C show how an adapter (502) and a collar (504) may be secured to syringe (402) to form an assembly (500). Adapter (502) enables syringe (402) to be coupled with a system with one or more powered components as described in greater detail below. FIGS. 16-17 show adapter (502) in greater detail. Adapter (502) may be coupled with proximal end (412) of syringe (402) after syringe (402) reaches the state shown in FIGS. 13C and 14B. Adapter (502) of this example has a proximal end (506) and a distal end (510). Proximal end (506) has a barbed connection feature (508) that is adapted for connection to tubing, for example. Distal end (510) comprises a tubular member (512) having annular recesses (514). A lumen (516) extends between a first opening (518) at proximal end (506) and a second opening (520) at distal end (510). A flange (522) is disposed between proximal end (506) and distal end (510) of syringe adapter (502). Flange (522) includes a proximal side (524) facing proximal end (506) of syringe adapter (502) and a distal side (526) facing distal end (510). Flange (522) includes a pair of opposing curved edges (528a, 528b) and a pair of opposing straight edges (530a, 530b). Each straight edge (530, 530b) is disposed between opposing ends of the curved edges (528a, 528b). In the present example, syringe adapter (502) is a single unitary body, but in other examples may comprise multiple portions coupled together. Various other suitable ways in which syringe adapter (502) may be configured will be apparent to a person skilled in the art in view of the teachings herein.

As shown best in FIGS. 17 and 21A-C, annular recesses (514) each receive sealing elements, which in the present example include an O-ring (532) received in each of the annular recesses (514). Tubular member (512) is sized and configured to be received in second opening (418) of syringe barrel (408) once, for example, plunger rod (436) is decoupled from piston (434) as shown in FIGS. 13C and 14B. O-rings (532) are configured to provide a fluid tight seal between lumen (420) of syringe (402) and syringe adapter (502) to prevent the escape of fluid pressure from second end of syringe (402). As discussed in more detail below, proximal end (506) of syringe adapter (502) may be coupled to a source of pressurized air or other fluid and distal end (510) of syringe adapter (502) may be received in second end of syringe (402). Therefore, pressurized air or fluid may be communicated to lumen (420) of syringe (402) via adapter (502), proximal to piston (434), and cause the advancement of piston (434) within syringe (402) to thereby dispense fluid from syringe (402). In some instances, adapter (502) may be used to communicate suction to lumen (420) of syringe (402), proximal to piston (434), and cause the retraction of piston (434) within syringe (402) to thereby draw fluid into syringe (402).

Figure 18:
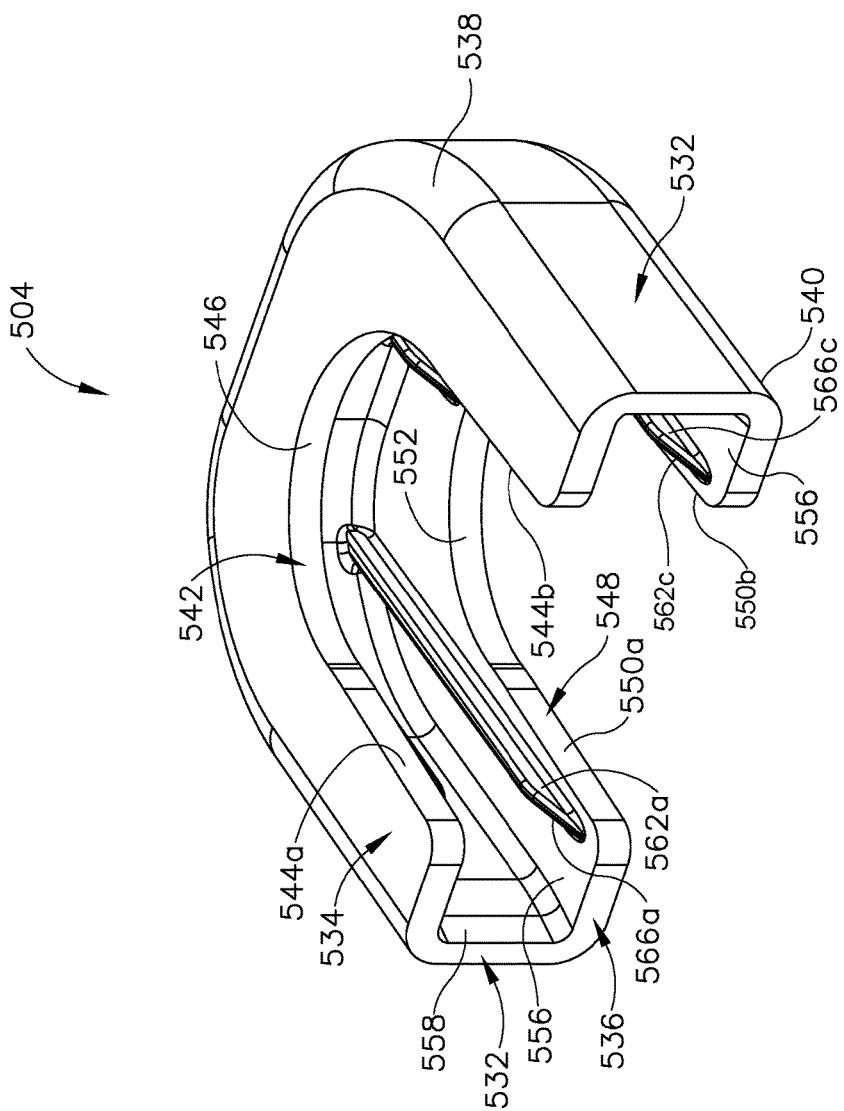
FIG. 18 depicts a perspective view of an exemplary engagement collar that is configured for use with the syringe of FIG. 12A and the syringe adapter of FIG. 16.
Figure 19:
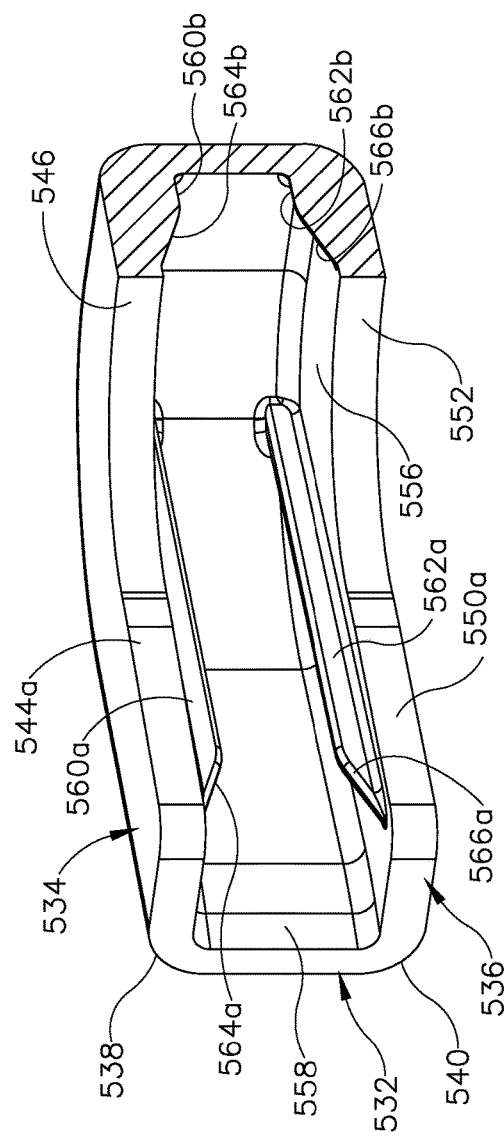
FIG. 19 depicts a perspective cross-sectional view of the engagement collar of FIG. 18.

FIGS. 18-19 show collar (504) in greater detail. Collar (504) may be used to secure adapter (502) to proximal end (412) of syringe (402) and thereby prevent movement of adapter (502) relative to syringe (402). Collar (504) is configured to keep adapter (502) secured to syringe (402) even when adapter (502) is communicating a pressurized medium to syringe (402) at a fluid pressure between approximately 20 psi and approximately 40 psi. Collar (504) of the present example includes a generally U-shaped body defined by a U-shaped wall (532), a first, upper flange (534) extending perpendicularly from the wall (532) and an opposing second, lower flange (536) extending perpendicularly from the wall (532). There is a curved, filleted edge (538, 540) between the wall (532) and each of the first and second flanges (534, 536), respectively. First flange (534) includes a U-shaped inner edge (542) with opposing straight portions (544a, 544b) and a curved portion (546) between the straight portions (544a, 544b). Second flange (536) also includes an inner edge (548) with opposing straight portions (550a, 550b) and a curved portion (552) between the straight portions (550a, 550b). First flange (534) and second flange (536) each include a respective inner portion (554, 556). Wall (532) includes an inner wall portion (558) that extends between and perpendicularly to inner flange portions (554, 556). Thus, inner flange portions (554, 556) and inner wall portion (558) define a U-shaped cavity.

Inner portion (554) of first flange (534) includes a plurality of ramps (560a-c) extending toward inner portion (556) of second flange (536), while inner portion (556) of second flange (536) includes a plurality of ramps (562a-c) extending toward inner portion (554) of first flange (534). Each of the ramps (560a-c, 562a-c) extends parallel to edges (544a-b, 550a-b). Ramps (560a, 560c) extend from near a front portion of collar (504) along opposing sides of inner portion (554) of flange (534) toward a rear portion of collar, while ramps (562a, 562c) extend from near a front portion of collar (504) along inner portion (556) of flange (536) toward a rear portion of collar (504). Ramp (560b) extends along inner portion (554) from near curved edge (546) toward rear portion of collar. Similarly, ramp (562b) extends along inner portion (556) from near curved edge (552) towards rear portion of collar (502). Ramps (560a-c) include tapered leading portions (564a-c), respectively. Similarly, ramps (562a-c) include tapered leading portions (566a-c), respectively.

FIGS. 20A-21C show how syringe (502), adapter (502), and collar (504) may be assembled together to form an assembly (500). It should be understood that the process described below would begin after syringe (402) has reached the state shown in FIGS. 13C and 14B. In order to assemble assembly (500), the operator directs tubular member (512) of syringe adapter (502) into opening (418) of syringe (402), in the absence of plunger rod (436), such that flange (522) of syringe adapter (502) is adjacent to or generally abuts flange (422) of syringe (402). This results in a transition from the configuration shown in FIGS. 20A and 21A to the configuration shown in FIGS. 20B and 21B. In the present example, O-rings 531 are sized and configured such that they are compressed to a smaller cross-sectional dimension between annular recesses (514) and lumen (420). O-rings 531 of the present example may include a lubricious coating such as silicone in order to reduce the friction between O-rings 531 and lumen (420) during insertion of syringe adapter (502) into syringe (402).

Figure 20A:
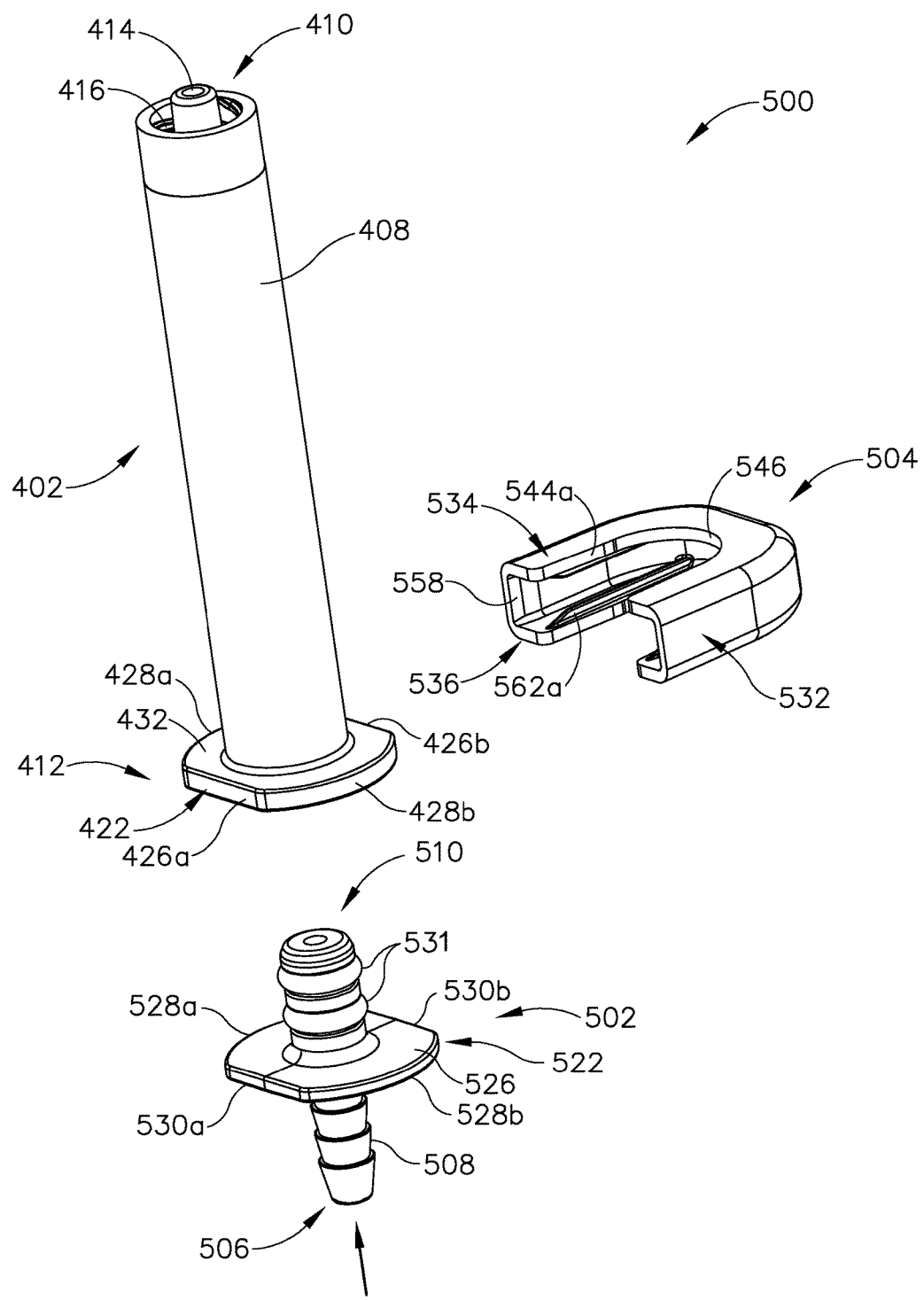
FIG. 20A depicts an exploded perspective view of the syringe of FIG. 12A, the syringe adapter of FIG. 16, and the engagement collar of FIG. 18.
Figure 20B:
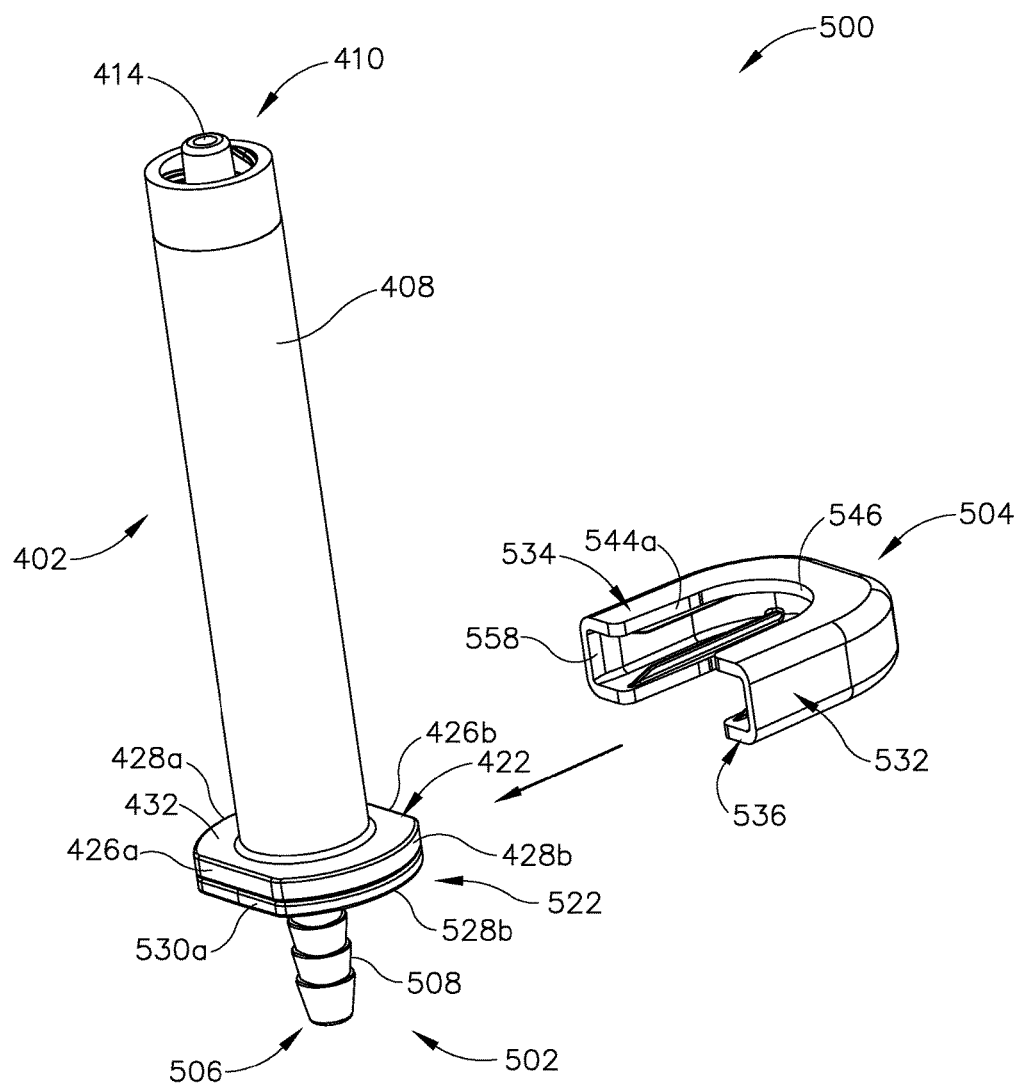
FIG. 20B depicts a partially exploded perspective view of the syringe of FIG. 12A, the syringe adapter of FIG. 16, and the engagement collar of FIG. 18, with the syringe adapter inserted into an end of the syringe and the engagement collar separated from the syringe and the syringe adapter.
Figure 20C:
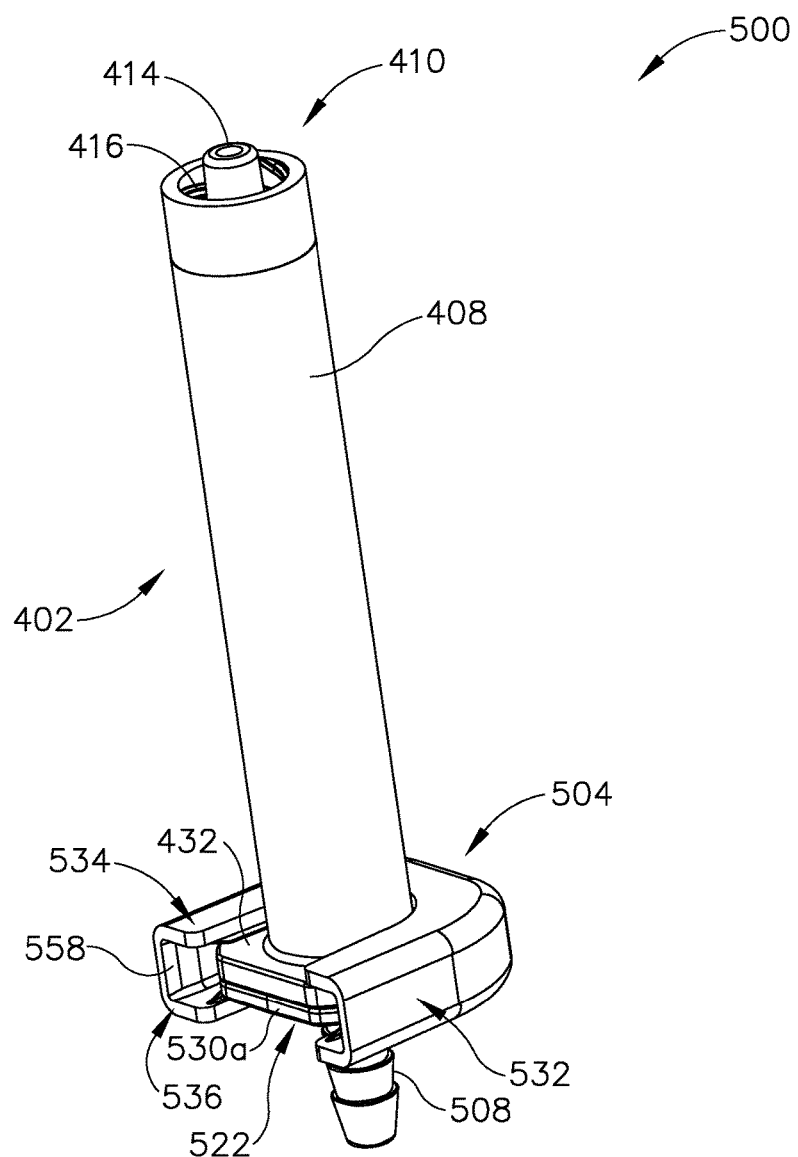
FIG. 20C depicts a perspective view of the syringe of FIG. 12A, the syringe adapter of FIG. 16, and the engagement collar of FIG. 18, with all of the components assembled together.
Figure 21A:
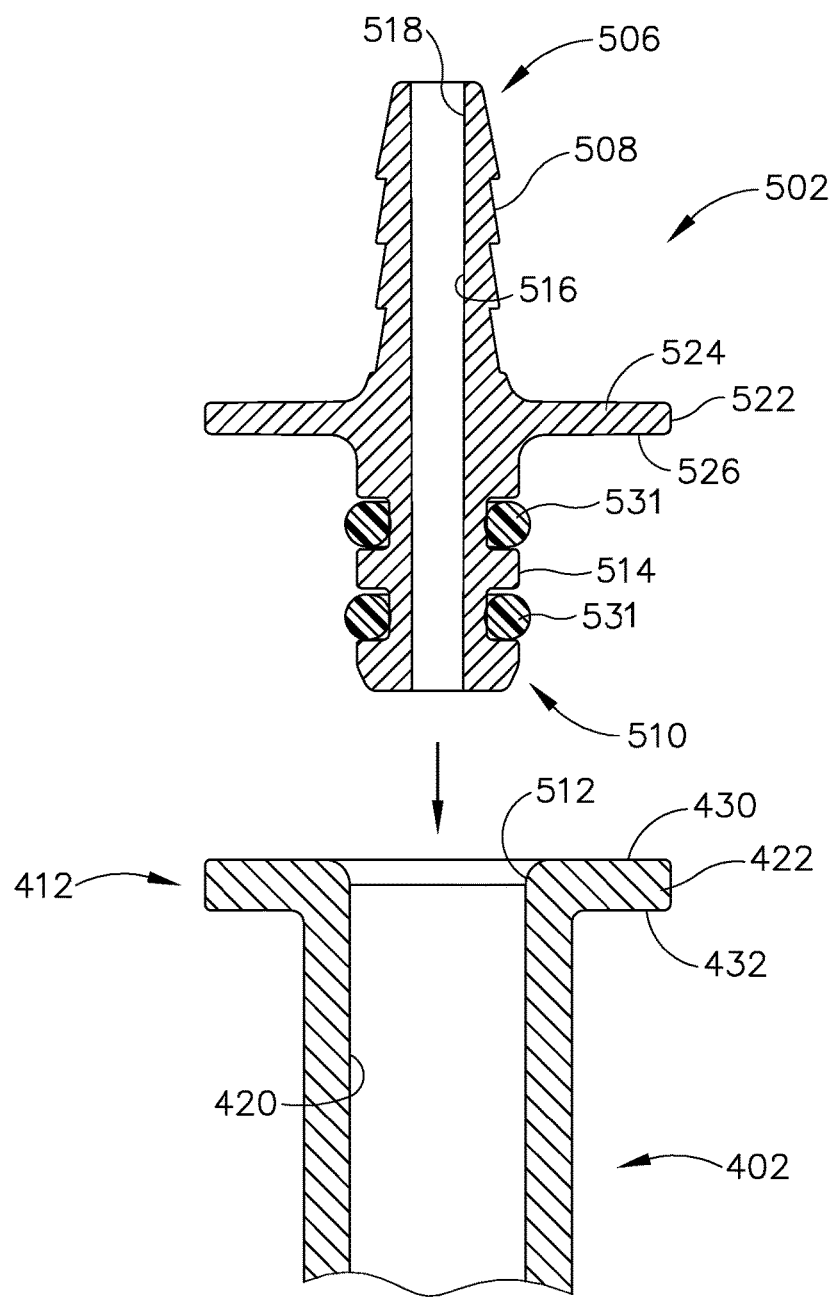
FIG. 21A depicts a side cross-sectional view of the syringe of FIG. 12A and the syringe adapter of FIG. 16, with the syringe adapter separated from an end of the syringe.
Figure 21B:
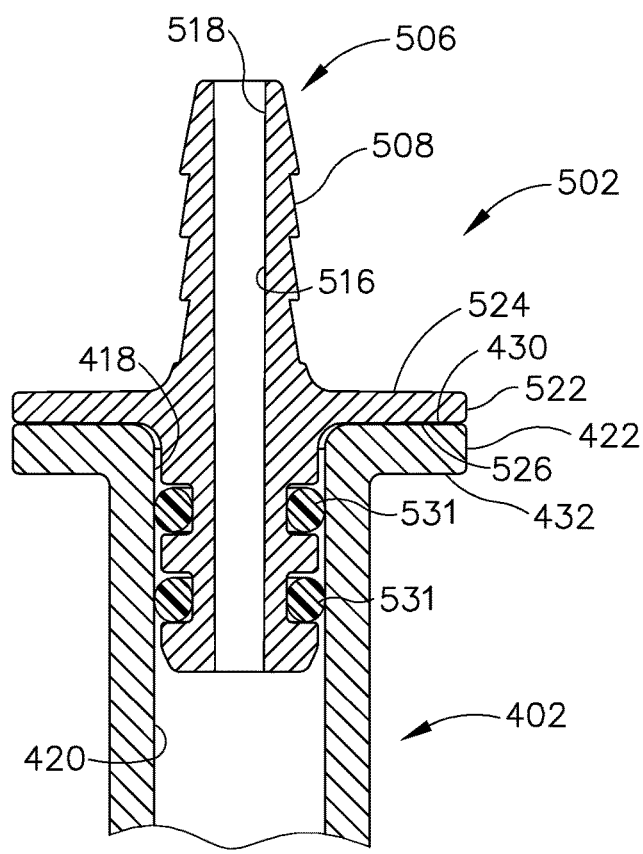
FIG. 21B depicts a side cross-sectional view of the syringe of FIG. 12A and the syringe adapter of FIG. 16, with the syringe adapter inserted into the end of the syringe.
Figure 21C:
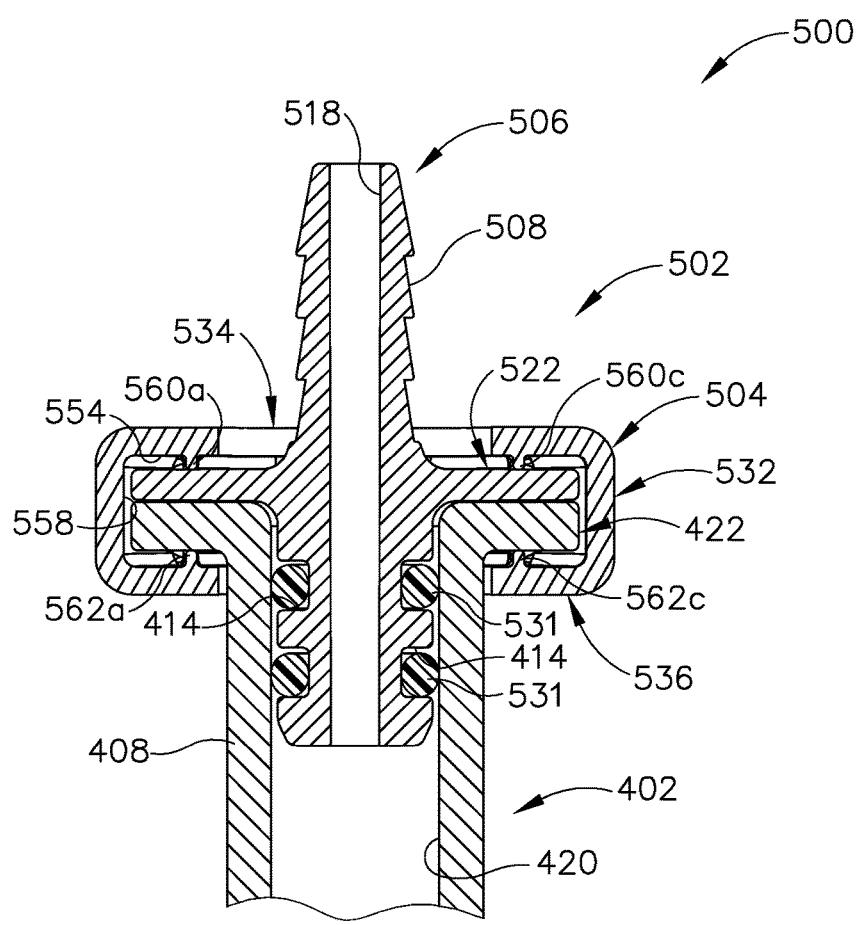
FIG. 21C depicts a side cross-sectional view of the syringe of FIG. 12A, the syringe adapter of FIG. 16, and the engagement collar of FIG. 18, with all of the components assembled together.

The operator may then direct engagement collar (504) into engagement with syringe (402) and syringe adapter (502), as shown in FIGS. 20C and 21C. In the present example, the operator directs engagement collar (504) relative to syringe (402) and syringe adapter (502) such that a portion of flanges (422, 522) enter into the U-shaped cavity. Particularly, engagement collar (504) is received within the U-shaped cavity such that curved edges of flanges (428a, 528a) and flanges (426a, 530a) are received adjacent to opposing inner wall portions (558) of engagement collar (504). As flanges (422, 522) are directed into the U-shaped cavity, proximal side (524) of flange (522) rides against tapered portions (564a, 564c) of ramps (560a, 560c), respectively, and distal side (432) of flange (422) rides against tapered portions (566a, 566c) of ramps (562a, 562c), respectively. As engagement collar (504) is directed further into engagement with syringe adapter (502) and syringe (402), flange (522) rides along non-tapered portions of ramps (560a, 560c) and flange (422) rides along non-tapered portions of ramps (562a, 562c). Thus, as the distance between ramps (560a, 562a) and ramps (560c, 562c) decreases to a generally constant distance past their respective tapered portions (564a, 566a) and (564c, 566c), compressive force from ramps (560a, 562a) becomes greater and flanges (422, 522) may be urged closer together such that distal side (526) of flange (522) more closely abuts and is urged in a compressive manner against proximal side (430) of flange (422).

Eventually, straight edge (426a) of flange (422) and straight edge (530a) of flange (522) are brought into contact with and ride against leading tapered portions of ramps (564b, 566b), respectively; and ride along to the non-tapered portions of ramps (560b, 562b). Ramps (560a-c) and ramps (562a-c) of the present example are rigid such that the interaction between ramps (560a-c), ramps (562a-c), and flanges (422, 522) results in an interference fit configuration of assembly (500). Ramps (560a-c), ramps (562a-c) and/or flanges (422, 522) may include other features that increase the frictional force therebetween and/or that increase the compressive force on flanges (422, 522) from ramps (560a-c, 562a-c). Suitable other ways in which assembly (500) may be configured and assembled will be apparent to persons skilled in the art in view of the teachings herein.

After reaching the state shown in FIGS. 20C and 21C, the operator may couple a flexible tube with barbed connection feature (508) to thereby couple assembly (500) with a source of a pressurized medium (e.g., air, saline) in a system with one or more powered components as described in greater detail below. The operator may further couple threaded portion (416) of syringe (402) with instrument (1000) to thereby dispense the fluid from syringe (402) to instrument (1000) as also described below.

FIGS. 23-27C show another exemplary assembly (600) including a syringe (602), a syringe adapter (702), and an engagement collar (804). Assembly (600) may also be coupled with a system with one or more powered components as described in greater detail below. In some examples, assembly (600) may also include a tab, such as tab (404). Assembly (600) is configured to operate substantially similar to assembly (500) such that syringe adapter (702) is configured to enable syringe (602) to be coupled to tubing, etc., that is further coupled to a source of a pressurized fluid medium. Similarly, engagement collar (804) is configured secure syringe (602) to syringe adapter (702) and to assist in preventing the escape of pressurized fluid from syringe (602) and/or syringe adapter (702). In that regard, syringe (602) is configured to operate substantially similar to syringe (402), except for the differences discussed below. Syringe adapter (702) is configured to operate substantially similar to syringe adapter (502), except for the differences discussed below. Similarly, engagement collar (804) is configured to operate substantially similar to engagement collar (504), except for the differences discussed below.

Syringe (602) of the present example comprises barrel (608) having a distal end (610) and a proximal end (612)). Distal end (610) includes a first, dispensing opening (614) and a threaded portion (616) that enables coupling of the syringe (602) to a needle, tubing, etc. In some versions, threaded portion (616) comprises a conventional luer fitting. Proximal end (612) includes a second opening (618) that is configured to receive tubular member (640). Lumen (620) extends between first and second openings (614, 618).

Proximal end (612) of syringe barrel (608) further comprises a flange (622), which extends radially outwardly relative to a longitudinal axis (624) of syringe (602) and acts as a finger grip when a user holds syringe (602). As shown best in FIGS. 22 and 26A, flange (622) is generally hexagonally shaped in the present example, though it should be understood that any other suitable shape may be used. Flange (622) further includes a proximal side (630) facing away from barrel (608) and a distal side (632) facing toward barrel (608).

Syringe (602) further includes a tubular member (640) received within lumen (620). Tubular member (640) includes a first end (642) having a first opening (644) abutted with the distal end of lumen (620) adjacent to dispensing opening (614) and a second end (646) having a second opening (648). Tubular member (640) includes a lumen (650) extending between first and second ends (646, 648). Tubular member (640) is frictionally received within lumen of syringe (602). A tube (652) extends distally from lumen (650) of tubular member (640), through second opening (648) of tubular member (640), and out dispensing opening (614) of syringe (602). Tubular member (640) is configured to receive a plunger assembly, such as plunger assembly (406), in order to draw fluid into lumen (650) of tubular member (640) and prime syringe (602). Similar to syringe (402), plunger assembly (406) may be used to dispense fluid from syringe (602). Alternatively, plunger assembly (406) may be decoupled, leaving a piston, such as piston (434), within lumen (420) so that piston (434) may be advanced and retracted via fluid pressure, in the manner discussed above with respect to syringe (402).

Figure 24:
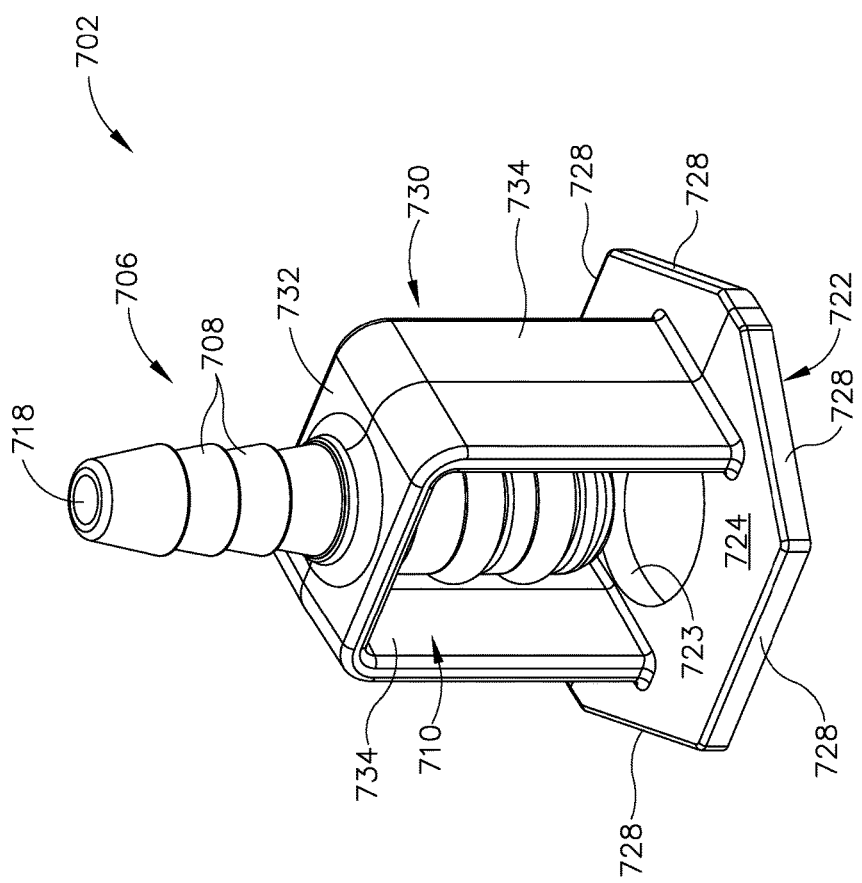
FIG. 24 depicts a perspective view of an exemplary alternative syringe adapter, configured for use with the syringe of FIG. 22.
Figure 25:
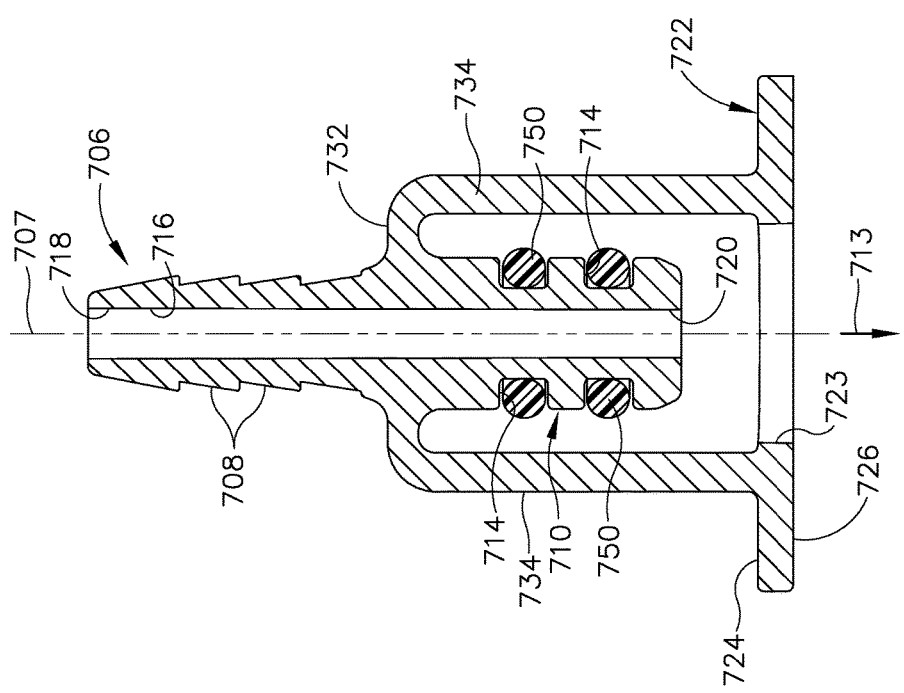
FIG. 25 depicts a side cross-sectional view of the syringe adapter of FIG. 24.

As shown best in FIGS. 24-25, syringe adapter (702) of the present example includes a proximal tubular portion (706) extending along axis (707) and comprising a barbed connection feature (708) that is adapted for connecting proximal tubular portion (706) to tubing, for example. Syringe adapter (702) further includes a distal tubular portion (710) opposing proximal tubular portion (706). Distal tubular portion (710) has a greater cross-sectional dimension than proximal tubular portion (706) and includes a plurality of annular recesses (714). A lumen (716) extends between a proximal opening (718) at proximal portion (706) and a distal opening (720) at distal portion (710).

Syringe adapter (702) further comprises a flange (722) positioned a distance away from distal tubular portion (710) (in the direction of arrow (713)). Flange (722) is positioned coaxially relative to tubular portions (706, 710) and includes a generally circular aperture (723), which is also positioned coaxially relative to first and second tubular portions (706, 710). Flange (722) includes a proximal side (724) facing in a direction opposite of arrow (713) syringe adapter (702) and a distal side (726) in the direction of arrow (713). Flange (722) is generally hexagonal and includes six edges (728), such that flange (722) is shaped to complement flange (622). Flange (722) includes an aperture (723) that is coaxial with tubular member (712) and is configured to receive tubular member (640) of syringe (602), as discussed in further detail below. A support member (730) connects flange (722) with tubular portions (706, 710). Support member (730) includes a first portion (732) that extends along a plane that is perpendicular to axis (707), and opposing legs (734) extending perpendicular to first portion (732) and parallel to axis (707) in the direction of arrow (713). In the present example, syringe adapter (502) is a single unitary body, but in other examples may comprise multiple portions coupled together.

As shown best in FIGS. 17 and 21A-C, annular recesses (714) each receive sealing elements, which in the present example include an O-ring (750) received in each of the annular recesses (714). Tubular portion (710) is sized and configured to be received in second opening (648) of tubular member (640) once, for example, the plunger rod (not shown) is decoupled from the piston (not shown). O-rings (750) are configured to provide a fluid tight seal between lumen (650) of tubular member (640) and syringe adapter (702) to prevent the escape of fluid pressure from second end (648) of tubular member (640). As discussed in more detail below, proximal tubular portion (706) of syringe adapter (702) may be coupled to a source of pressurized fluid medium and distal tubular portion (710) of syringe adapter (702) may be received in second end (648) of tubular member (640). Therefore, a pressurized fluid medium may be communicated to lumen (650) of tubular member (640) via adapter (702) and cause the advancement or retraction of the piston (not shown) within tubular member (640) to cause fluid to be dispensed from or drawn into tubular member (640), respectively.

As shown in FIGS. 26A-27C, in order to assemble assembly (600), an operator inserts distal tubular portion (710) of syringe adapter (702) into opening (648) of tubular member (640), in the absence of plunger rod (436), such that flange (722) of syringe adapter (702) is adjacent to or generally abuts flange (622) of syringe (602). In the present example, O-rings (750) are sized and configured such that they are compressed to a smaller cross-sectional dimension between annular recesses (714) and lumen (650). O-rings (750) of the present example may include a lubricious coating such as silicone in order to reduce the friction between O-rings (750) and lumen (650) during insertion of syringe adapter (702) into syringe (602). Insertion of distal tubular portion (710) into tubular member (640) results in a transition from the configuration shown in FIGS. 26A and 27A to the configuration shown in FIGS. 26B and 27B.

The operator may then direct engagement collar (804) into engagement with syringe (602) and syringe adapter (702) in a substantially similar manner as described above with respect to engagement collar (504), syringe (402), and syringe adapter (502). This will result in the configuration shown in FIGS. 26C and 27C. Engagement collar (804) is configured to operate substantially similar to engagement collar (504), except that the general shape of engagement collar (804) has been adapted for use with the hexagonal shape of flanges (622, 722). Thus, the operator directs engagement collar (802) relative to syringe (602) and syringe adapter (702) such that a portion of flanges (622, 722) enter into a U-shaped cavity. Ramps (860a, 862a) and ramps (860c, 862c) of engagement collar (only 860a, 862a, 860c, 862c are shown) provide a compressive force on flanges (622, 722) such that flanges may be urged closer together in a substantially similar manner to flanges (422, 522) as discussed above. Suitable other ways in which assembly (600) may be configured will be apparent to persons skilled in the art in view of the teachings herein.

Figure 26A:
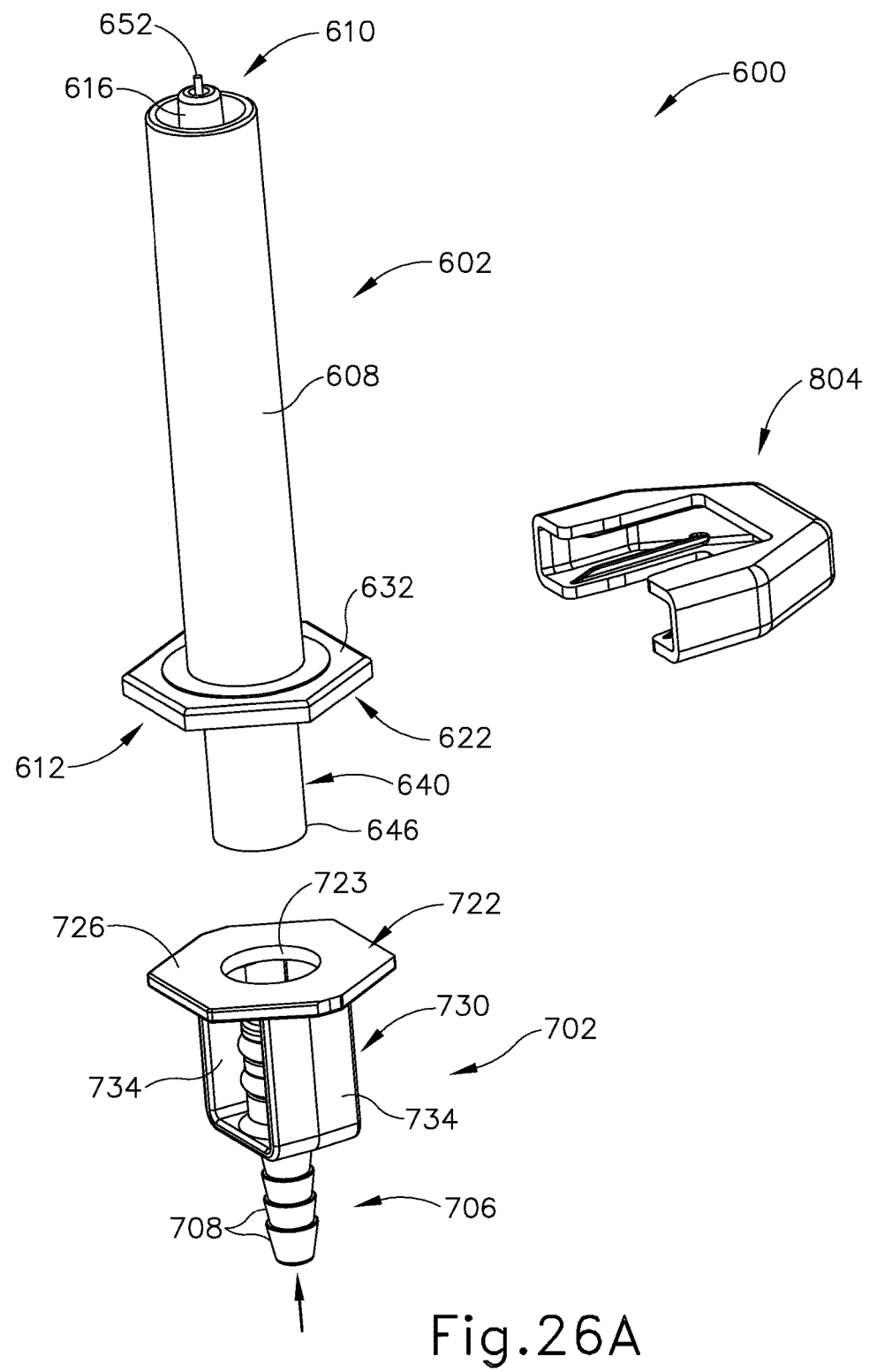
FIG. 26A depicts an exploded perspective view of the syringe of FIG. 22, the syringe adapter of FIG. 24, and an exemplary alternative engagement collar.
Figure 26B:
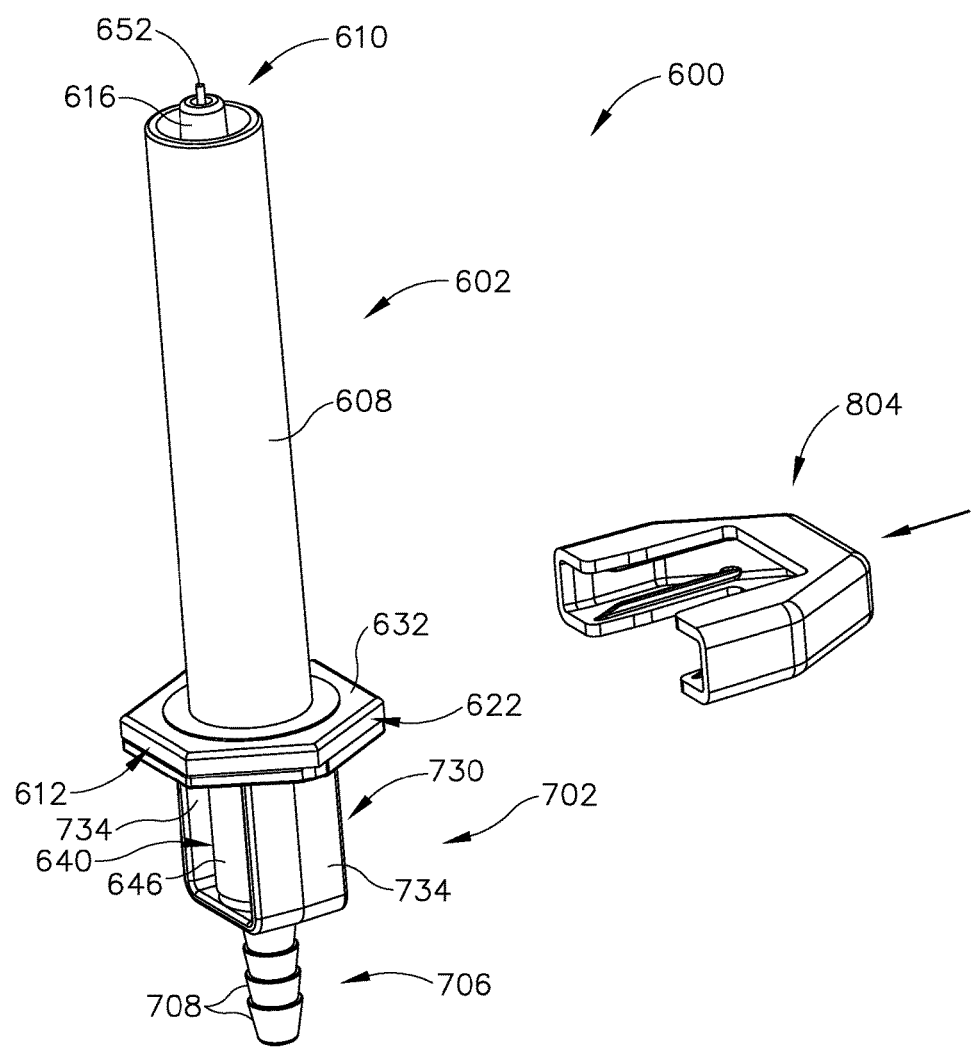
FIG. 26B depicts a partially exploded perspective view of the syringe FIG. 22, the syringe adapter of FIG. 24, and the engagement collar of FIG. 26A, with the syringe adapter positioned over an end of the syringe and the engagement collar separated from the syringe and the syringe adapter.
Figure 26C:
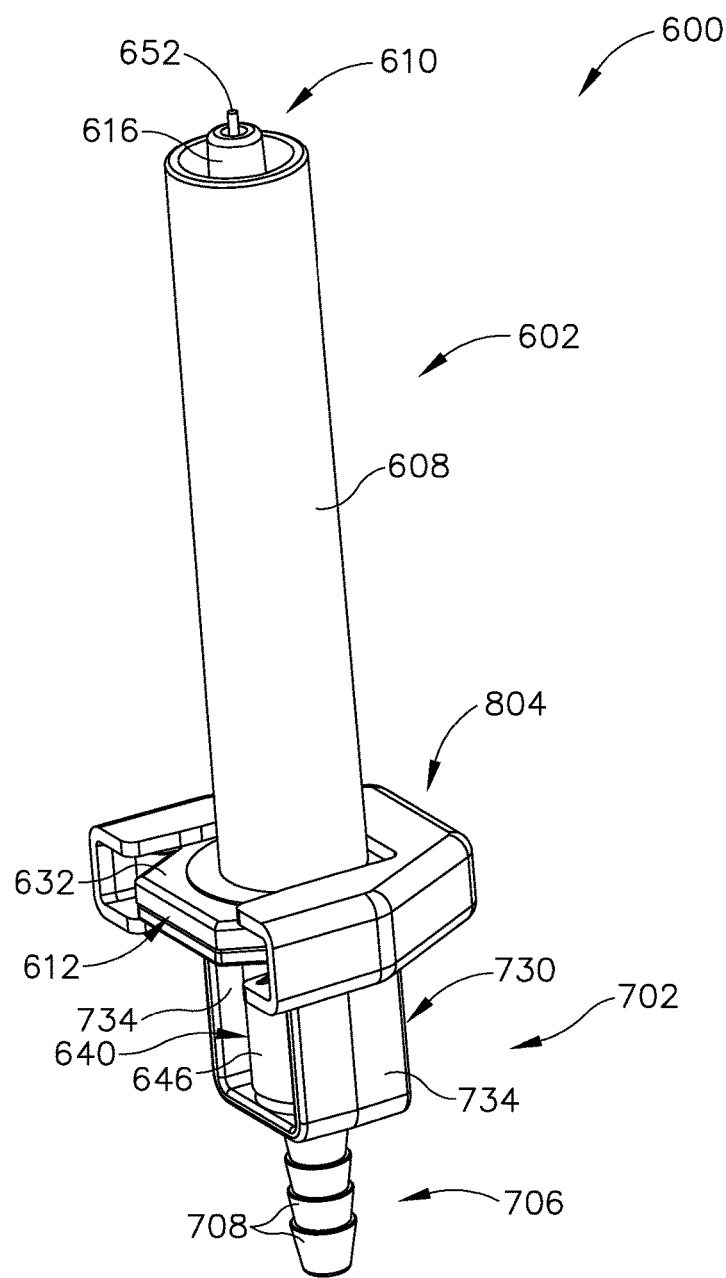
FIG. 26C depicts a perspective view of the syringe of FIG. 22, the syringe adapter of FIG. 24, and the engagement collar of FIG. 26A, with all of the components assembled together.
Figure 27A:
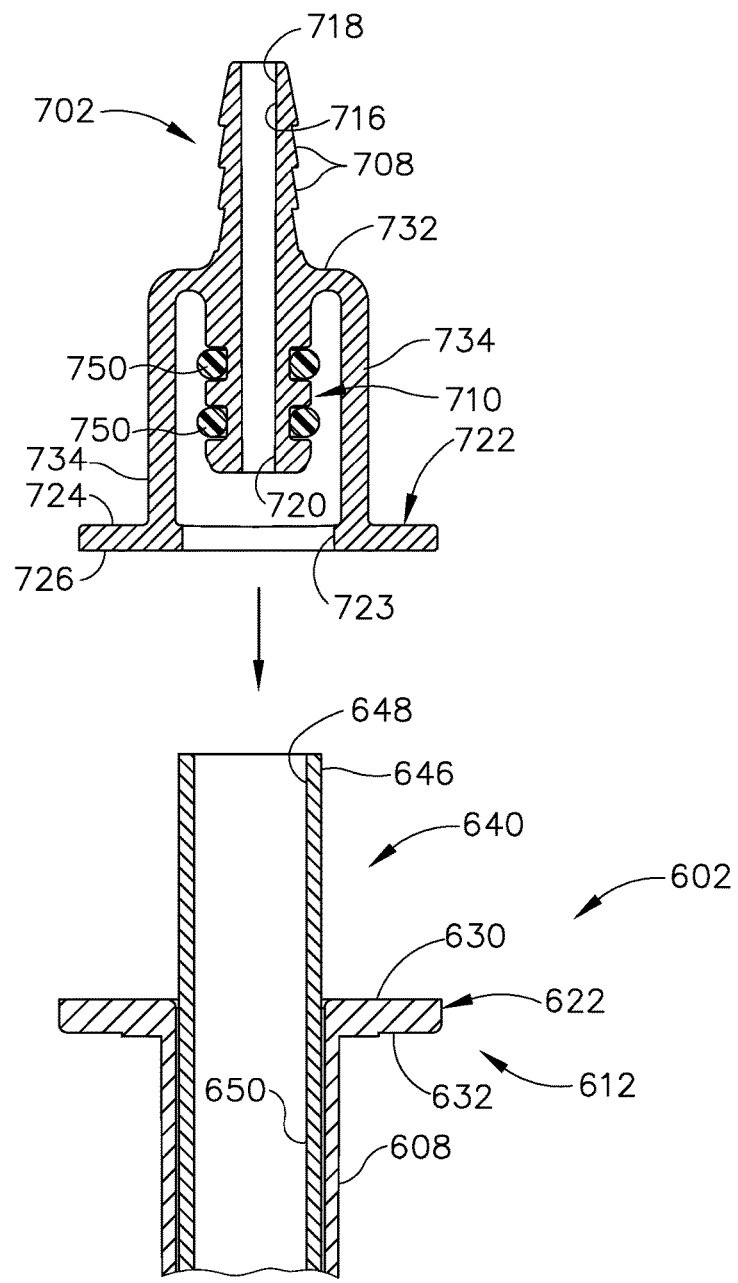
FIG. 27A depicts a side cross-sectional view of the syringe of FIG. 22, the syringe adapter of FIG. 24, with the syringe adapter separated from an end of the syringe.
Figure 27B:
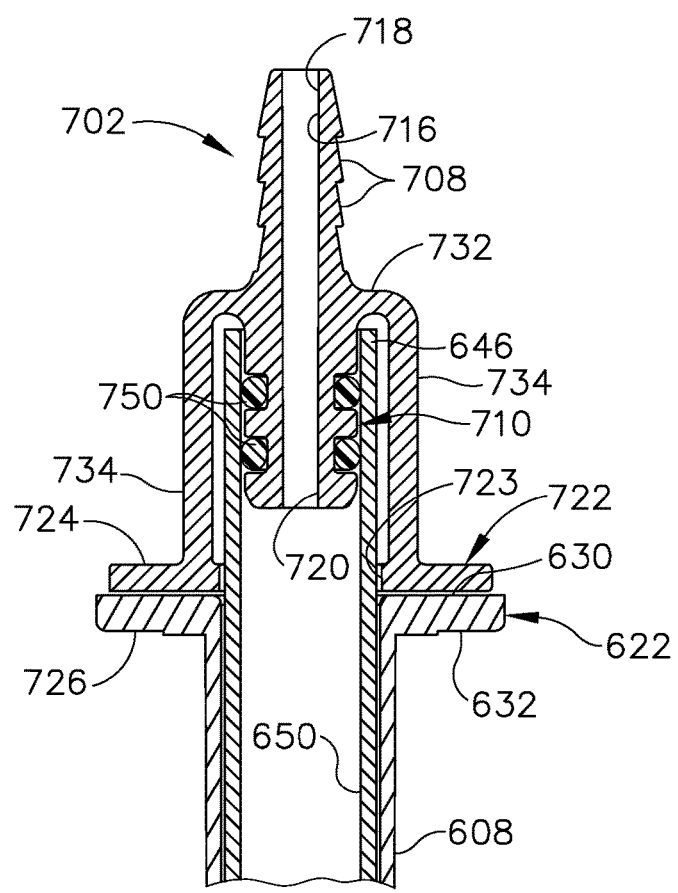
FIG. 27B depicts a side cross-sectional view of the syringe of FIG. 22 and the syringe adapter of FIG. 24, with the syringe adapter positioned over the end of the syringe.
Figure 27C:
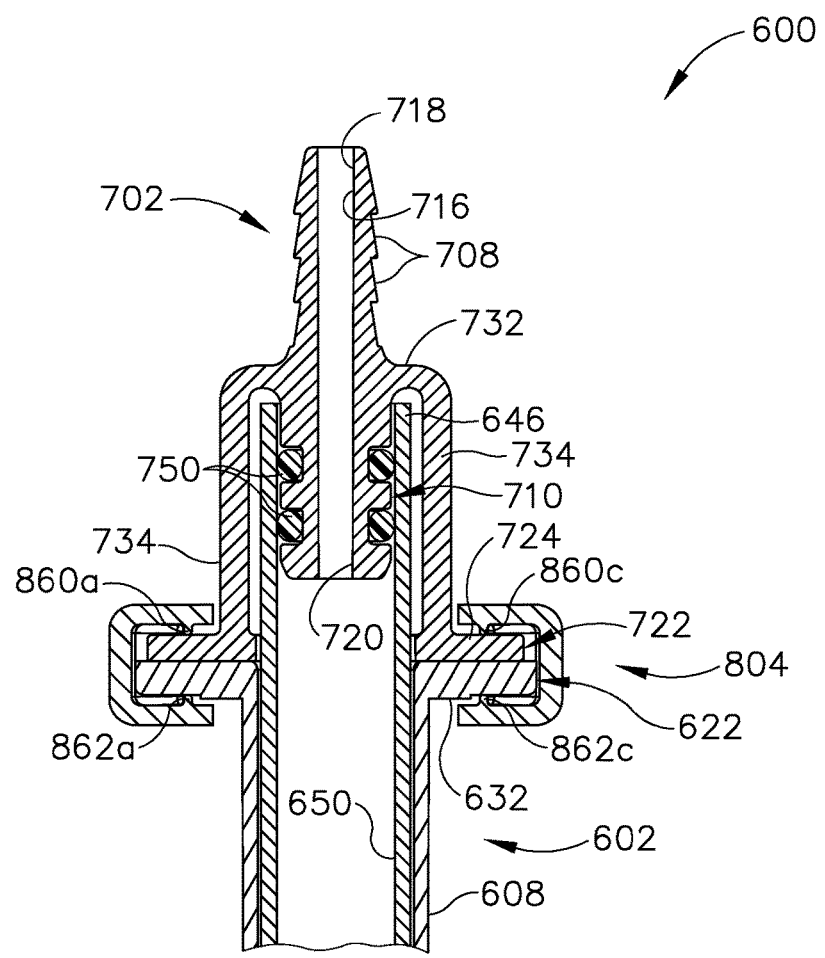
FIG. 27C depicts a side cross-sectional view of the syringe of FIG. 22, the syringe adapter of FIG. 24, and the engagement collar of FIG. 26A, with all of the components assembled together.

After reaching the state shown in FIGS. 26C and 27C, the operator may couple a flexible tube with barbed connection feature (708) to thereby couple assembly (600) with a source of a pressurized medium (e.g., air, saline) as described below. The operator may further couple threaded portion (616) of syringe (602) with instrument (1000) to thereby dispense the fluid from syringe (602) to instrument (1000) as also described below.

Figure 28:
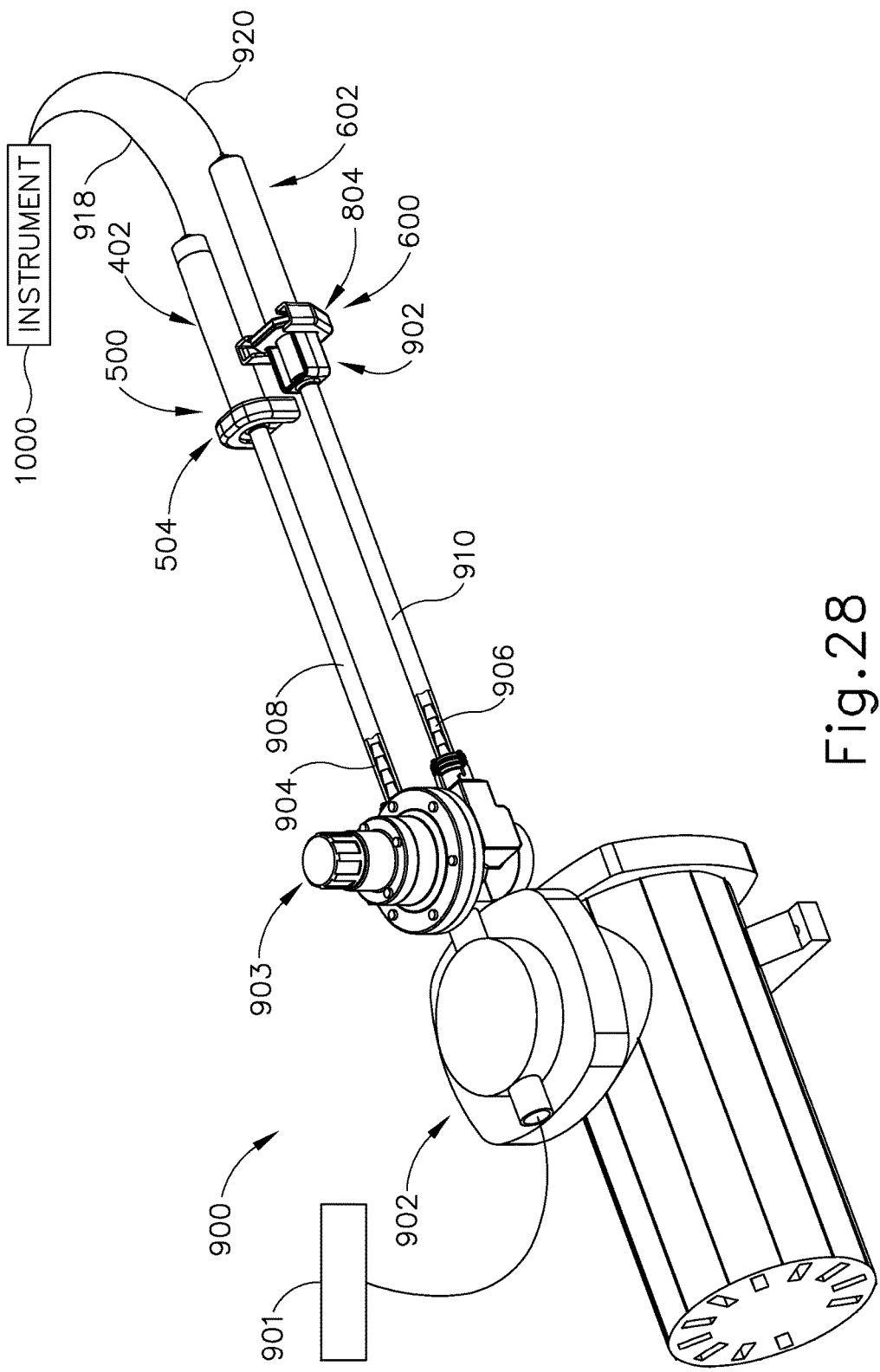
FIG. 28 depicts a perspective view of an exemplary pneumatic pressure control delivery system coupled with the syringe of FIG. 12A, the syringe of FIG. 22, and an instrument for subretinal administration of a therapeutic agent from a suprachoroidal approach.
Figure 29:
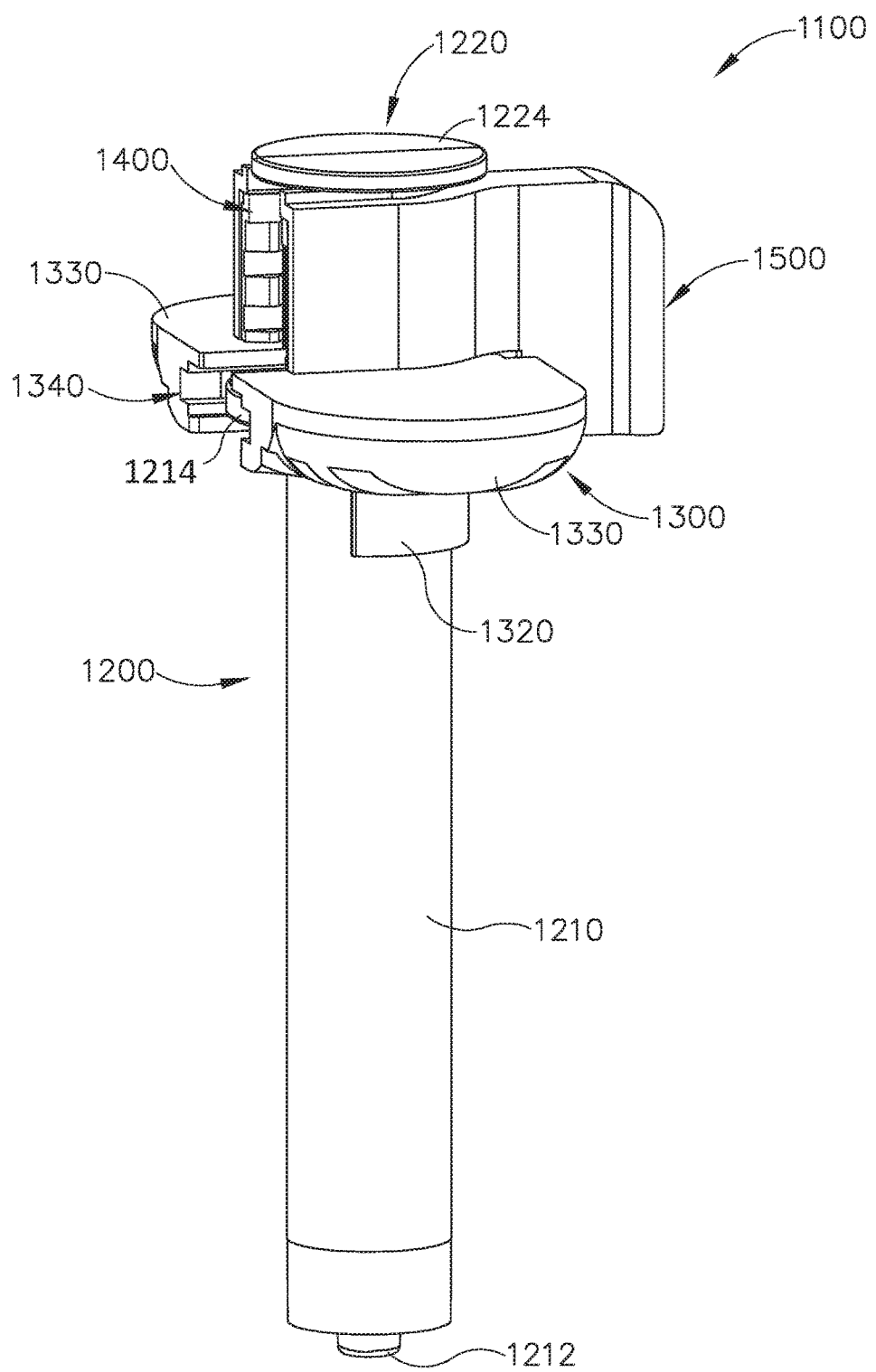
FIG. 29 depicts a perspective view of another exemplary fluid delivery assembly that may be used with the instruments of FIGS. 1 and 7.

VII. Exemplary Powered Injection System for Delivering Therapeutic Fluids for Treatment of an Ocular Condition FIG. 28 shows an exemplary pressure control delivery system (900) for delivering one or more fluids during a procedure to treat an ocular condition, such as the subretinal delivery of therapeutic agent (341) described above with respect to FIGS. 9A-11C. In the present example, system (900) comprises a fluid medium source (901) that is coupled with a fluid pump (902) and a pressure regulator (903). In some examples, fluid medium source (901) comprises saline. In some other examples, air is used as the pressurized fluid medium. Other suitable fluid media that may be used will be apparent to those of ordinary skill in the art in view of the teachings herein. It should be understood that pump (902) is operable to pressurize the fluid medium and regulator (903) is operable to regulate the fluid pressure of the pressurized fluid medium that is output from pump (902). Various suitable forms that pump (902) and regulator (903) may take will be apparent to those of ordinary skill in the art in view of the teachings herein.

Pressure regulator (903) comprises pneumatic connectors (e.g., CPC SMS Series connectors) with barbed fittings (904, 906). Barbed fitting (904) is coupled with assembly (500) via a tube (908). In particular, tube (908) is secured to barbed connection feature (508). Thus, pressurized fluid medium may be delivered from pump (902) to assembly (500) via regulator (903) and tube (908) to thereby dispense fluid from syringe (402). Barbed fitting (906) is coupled with assembly (600) via a tube (910). In particular, tube (910) is secured to assembly (600) via barbed connection feature (708). Thus, pressurized fluid medium may be delivered from pump (902) to assembly (600) via regulator (903) and tube (910) to thereby dispense fluid from tubular member (640) via syringe (602).

Instrument (1000) is coupled with both assemblies (500, 600) via tubes (918, 920). In particular, instrument (1000) is coupled with assembly (500) via tube (918); and with assembly (600) via tube (920). Tube (918) is coupled with assembly (500) via threaded portion (416). Tube (920) is coupled with assembly (600) via threaded portion (616). As noted above, instrument (1000) may be configured and operable like instruments (10, 2010) described above. Tubes (918, 920) of system (900) may thus serve as tubes (64) or tubes (2090, 2091) as described above.

In an exemplary method of operation, each assembly (500, 600) is filled with fluid (e.g., bleb fluid (340), therapeutic agent (341), etc.), the air is purged from each assembly (500, 600), and the remaining amount of fluid is reduced to the predetermined amount (e.g., using tab (404), etc.) as described above. Assemblies (500, 600) are then coupled with pressure regulator (903) via tubes (908, 910); and with instrument (1000) via tubes (918, 920). Once instrument (1000) has been appropriately positioned with respect to a patient, such that instrument (1000) is positioned to deliver fluid to a target site (e.g., the subretinal space) in the patient, system (900) may be activated. In particular, fluid pump (902) may be activated to pressurize the fluid medium from source (901); regulator (903) may regulate the pressure of the fluid output from fluid pump (902); and the pressurized fluid medium may reach each assembly (500, 600) via tubes (908, 910). At this stage, the pressure within each assembly (500, 600) will be effectively pressurized due to the pressurized fluid medium from source (901) acting against the proximal face of piston (434) in each assembly (500, 600).

In the present example, instrument (1000) includes a valve assembly that is in fluid communication with tubes (918, 920). This valve assembly enables instrument (1000) to deliver the pressurized fluid from each assembly (500, 600) at a selected time and in a selected sequence (e.g., to ensure that bleb fluid (340) is delivered first; then therapeutic agent (341)). For instance, instrument (1000) may include an integral valve assembly that is configured and operable in accordance with at least some of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. In addition or in the alternative to instrument (1000) having an integral valve assembly, system (900) may also include one or more valves. For instance, system (900) may include one or more valves interposed between assemblies (500, 600) and instrument (1000). In addition or in the alternative, system (900) may include one or more valves interposed between regulator (903) and assemblies (500, 600). Other suitable ways in which valves may be incorporated into instrument (1000) and/or system (900) will be apparent to those of ordinary skill in the art in view of the teachings herein.

In some examples, assembly (500) contains bleb fluid (340), such that system (900) is operable to deliver bleb fluid (340) from assembly (500) to instrument (1000) via tube (918); and assembly (600) contains therapeutic agent (341), such that system (900) is operable to deliver therapeutic agent (341) from assembly (600) to instrument (1000) via tube (920). In some other examples, assembly (500) contains therapeutic agent (341), such that system (900) is operable to deliver therapeutic agent (341) from assembly (500) to instrument (1000) via tube (918); and assembly (600) contains bleb fluid (340), such that system (900) is operable to deliver bleb fluid (340) from assembly (600) to instrument (1000) via tube (920). It should therefore be understood that system (900) may be used in combination with instrument (1000) to perform the subretinal delivery of bleb fluid (340) and therapeutic agent (341) described above with respect to FIGS. 9A-11C. Other suitable ways in which system (900) may be used, with or without instrument (1000), will be apparent to those of ordinary skill in the art in view of the teachings herein.

VIII. Exemplary Manual Injection System with Spacers for Controlling Priming and Delivered Fluid Volume FIGS. 29-36G depict another exemplary fluid delivery assembly (1100) that may be used to store and deliver predetermined amount of fluids, such as bleb (340) fluid and therapeutic agent (341) fluid as described above, to a subretinal space in a precise and consistent manner via an instrument (e.g., instrument (10, 2010)). As discussed in more detail below, this system may be fluidly coupled with an instrument (1000), which may be configured and operable just like instrument (10, 2010) described above. Alternatively, instrument (1000) may have any other suitable configuration and may be configured for use with fluid delivery assembly (1100) in any suitable procedure calling for delivery of a predetermined amount of fluid.

Figure 30:
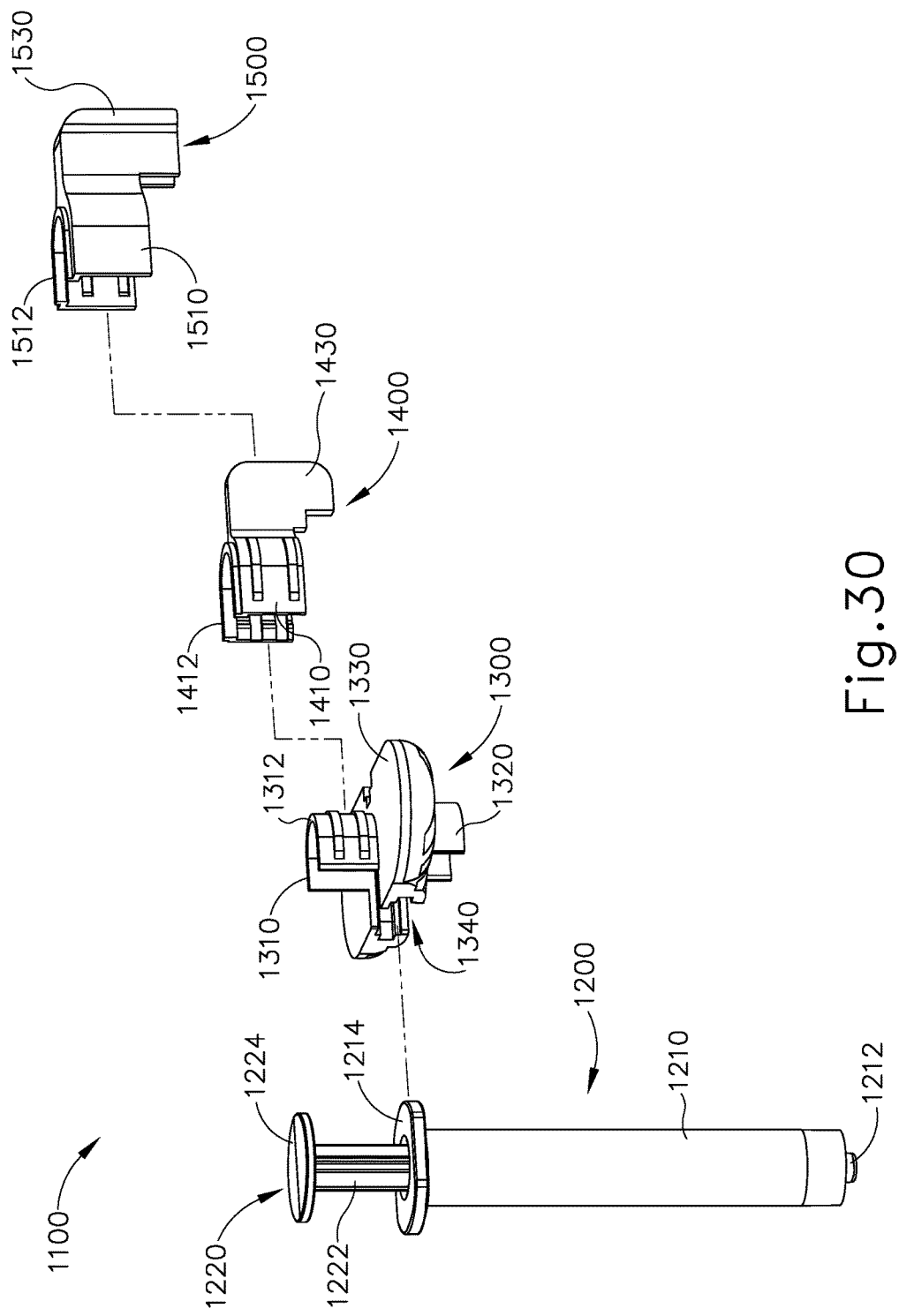
FIG. 30 depicts an exploded perspective view of the fluid delivery assembly of FIG. 29.
Figure 36A:
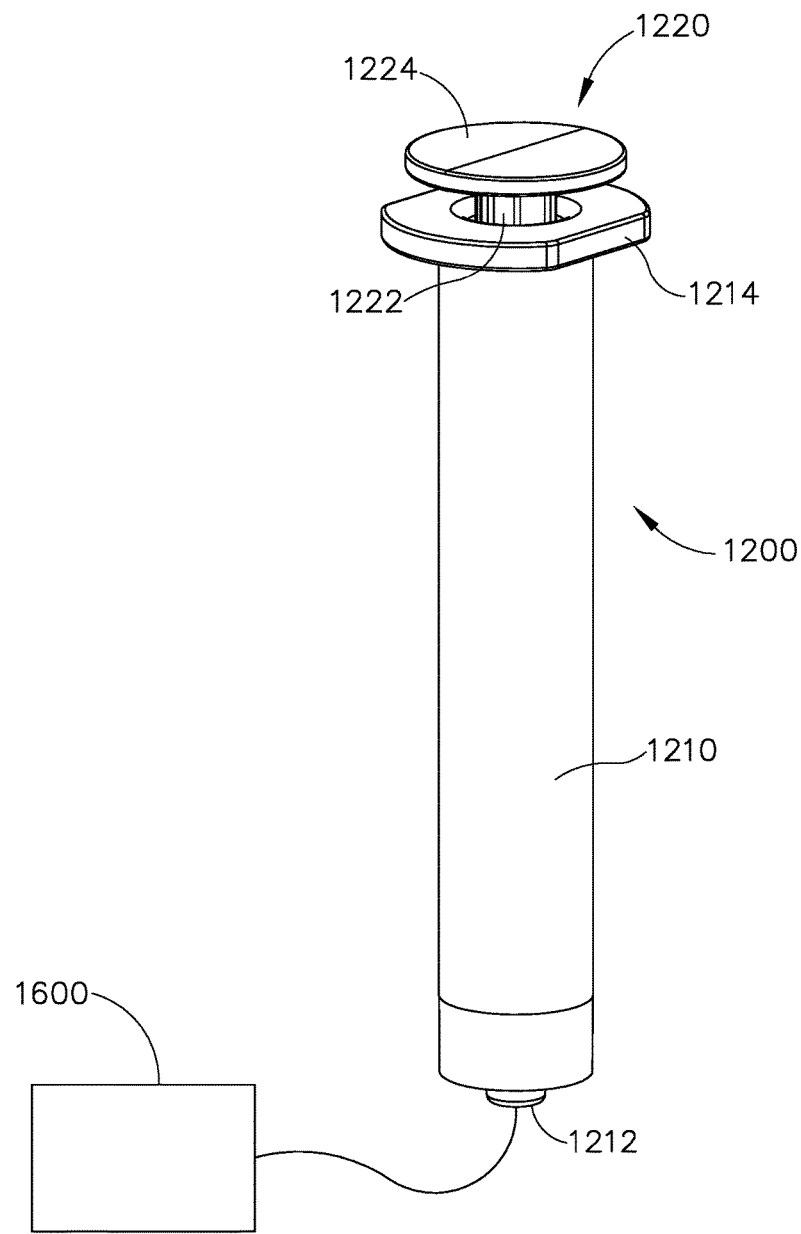
FIG. 36A depicts a perspective view of a syringe assembly of the fluid delivery assembly of FIG. 29, coupled with a fluid source, with a plunger of the syringe assembly in a fully advanced position.
Figure 36B:
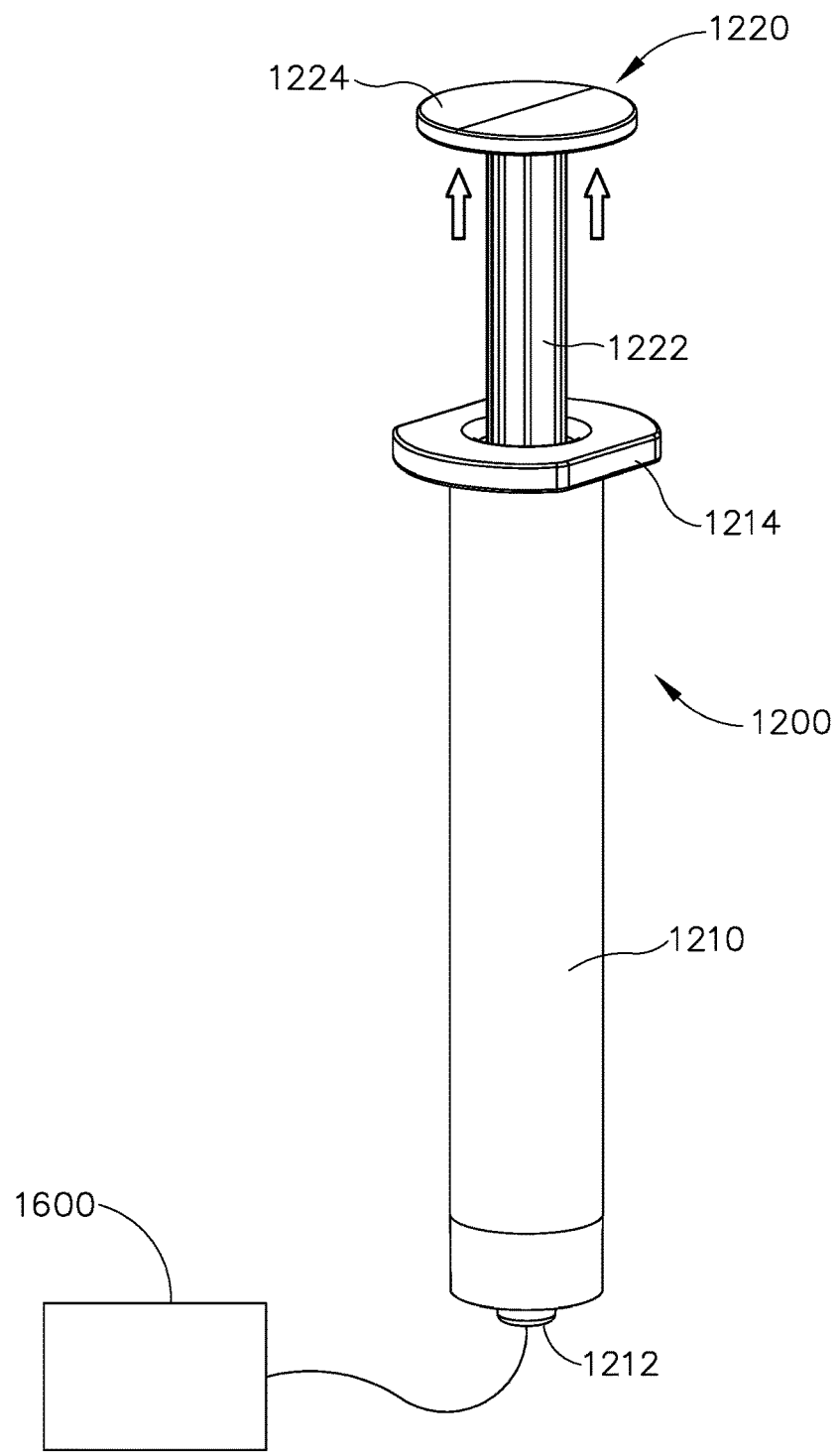
FIG. 36B depicts a perspective view of the syringe assembly and fluid source of FIG. 36A, with the plunger in a retracted position.

Fluid delivery assembly (1100) of the present example comprises a syringe assembly (1200), a first spacer (1300), a second spacer (1400), and a third spacer (1500). As best seen in FIGS. 30 and 36A-36B, syringe assembly (1200) comprises a barrel (1210) and a plunger (1220). Barrel (1210) of the present example comprises a port (1212) and a flange (1214). Plunger (1220) comprises a shaft (1222) and a thumb flange (1224). Plunger (1220) also includes a piston (not shown) that is slidably disposed in barrel (1210) to provide a variable volume within barrel (1210), in accordance with conventional syringe construction and operability. It should therefore be understood that plunger (1220) may be reciprocated relative to barrel (1210) in order to draw fluid into barrel (1210) or expel fluid from barrel (1210).

Figure 31:
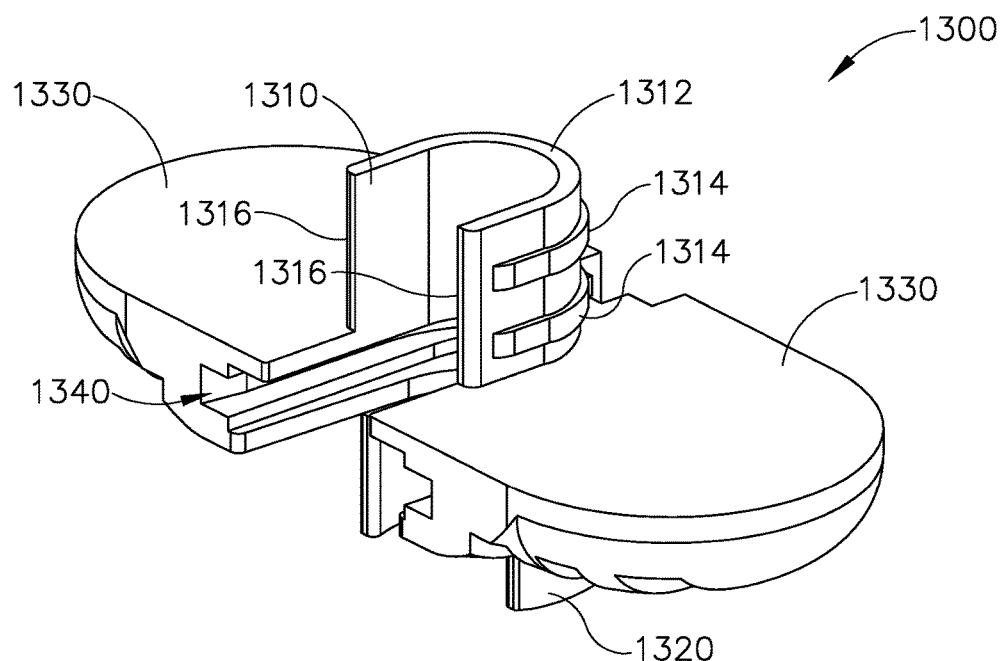
FIG. 31 depicts a perspective view of a first spacer of the fluid delivery assembly of FIG. 29.

As shown in FIGS. 29-30, 35, and 36C, spacers (1300, 1400, 1500) are configured to nest with each other and syringe assembly (1200). As best seen in FIG. 31, first spacer (1300) comprises an upper sleeve (1310), a lower sleeve (1320), and a pair of outwardly extending finger grips (1330). Sleeves (1310, 1320) each generally define a "U" shape. First spacer (1300) further defines a channel (1340), which is configured to receive flange (1214) of barrel (1210) as shown in FIGS. 29-30, 35, and 36C-36G. When first spacer (1300) is coupled with barrel (1210), the fit between channel (1340) and flange (1214) prevents relative longitudinal movement between first spacer (1300) and barrel (1210). In addition, when first spacer (1300) is coupled with barrel (1210), upper sleeve (1310) extends upwardly relative to flange (1214); while lower sleeve (1320) partially encompasses barrel (1210). In some versions, lower sleeve (1320) provides a snug fit about barrel (1210) such that first spacer (1300) releasably grips onto barrel (1210). In addition or in the alternative, channel (1340) may be configured to provide a snap fit, snug fit, and/or some other kind of releasable gripping engagement with flange (1214) to thereby enable first spacer (1300) to releasably grip onto barrel (1210). Referring back to FIG. 31, upper sleeve (1310) further includes an upper ledge (1312), a pair of engagement ridges (1314), and a pair of engagement edges (1316). Each of these features will be described in greater detail below.

Figure 32:
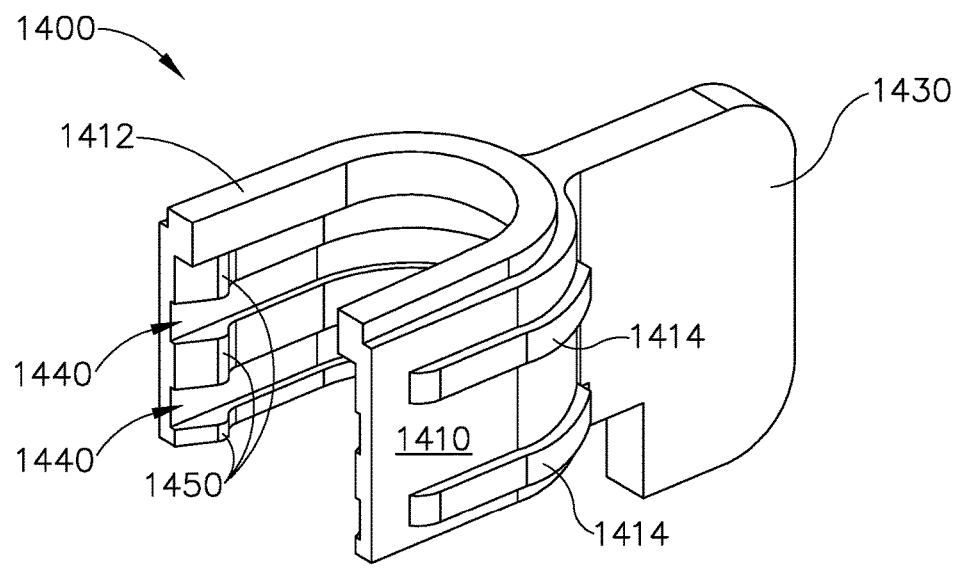
FIG. 32 depicts a perspective view of a second spacer of the fluid delivery assembly of FIG. 29.
Figure 33:
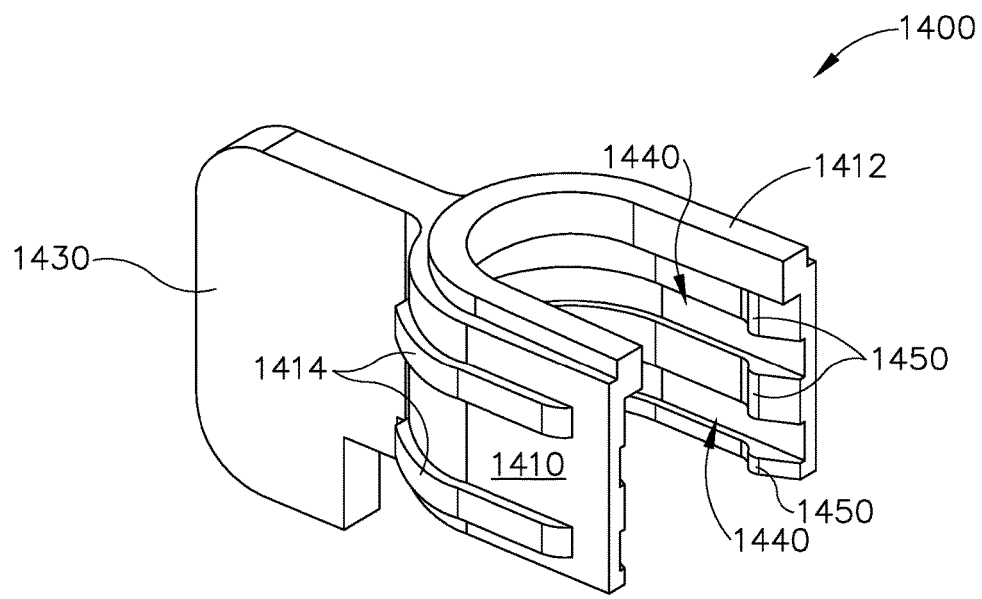
FIG. 33 depicts another perspective view of the second spacer of FIG. 32.
Figure 35:
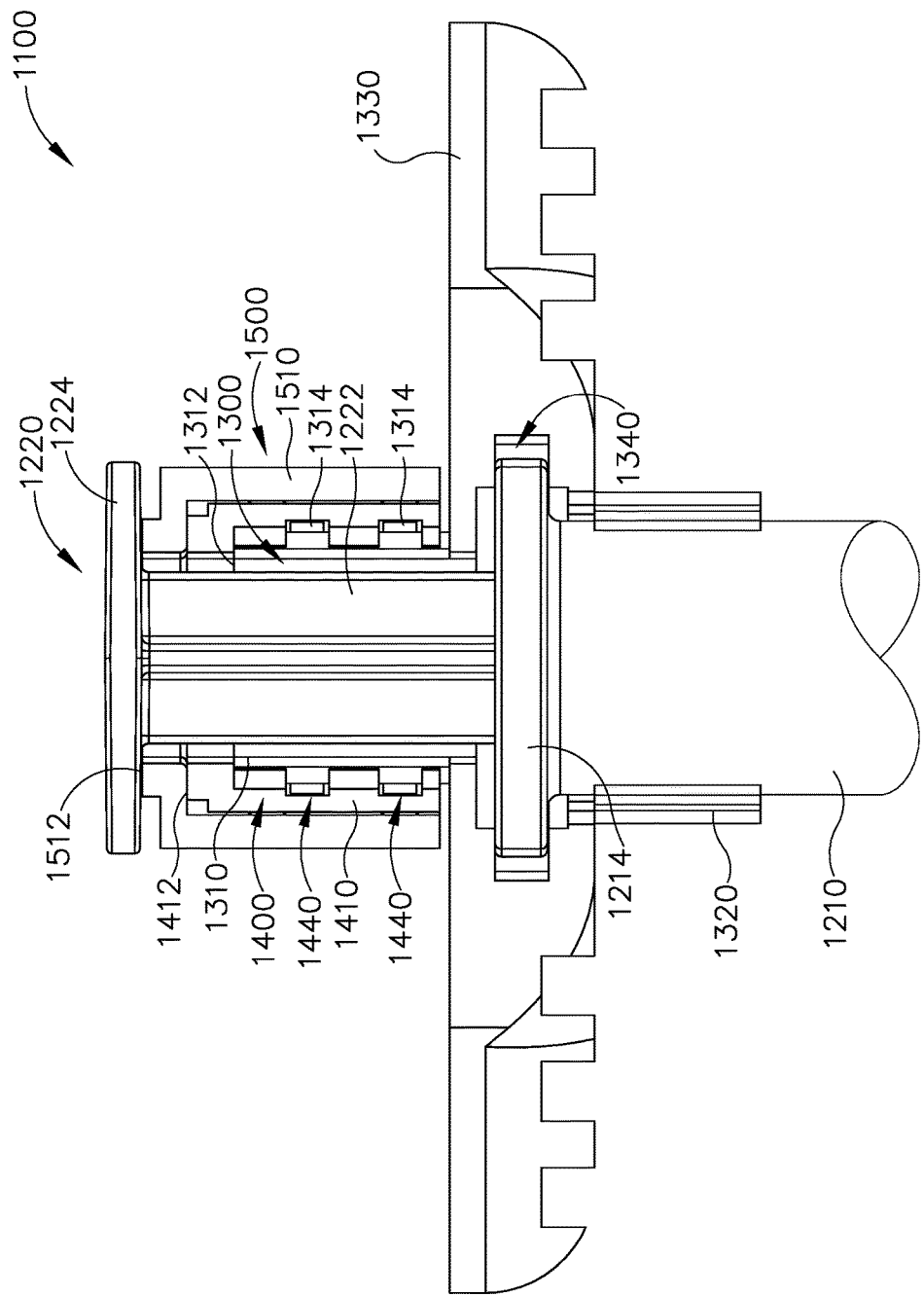
FIG. 35 depicts an partial side elevational view of the fluid delivery assembly of FIG. 29, showing the spacers secured to each other and to a syringe assembly.

As best seen in FIGS. 32-33, second spacer (1400) comprises a sleeve (1410) and a grip (1430) extending laterally from sleeve (1410). Sleeve (1410) defines a "U" shape and includes an upper ledge (1412), a pair of engagement ridges (1414), and a pair of engagement channels (1440). Sleeve (1410) further includes a set of latches (1450). Second spacer (1400) is configured to fit around first spacer (1300), as shown in FIGS. 29-30, 35, and 36C-36E. In particular, sleeve (1410) of second spacer (1400) is configured to encompass upper sleeve (1310) of first spacer (1300), with engagement ridges (1314) fitting in engagement channels (1440). When engagement ridges (1314) are fully seated in engagement channels (1440), latches (1450) engage engagement ridges (1314) to provide a snap fit between second spacer (1400) and first spacer (1300). Of course, any other suitable structures and techniques may be used to releasably secure second spacer (1400) to first spacer (1300). As best seen in FIG. 35, spacers (1300, 1400) are configured such that upper ledge (1412) is positioned higher than upper ledge (1312) when spacers (1300, 1400) are secured together.

Figure 34:
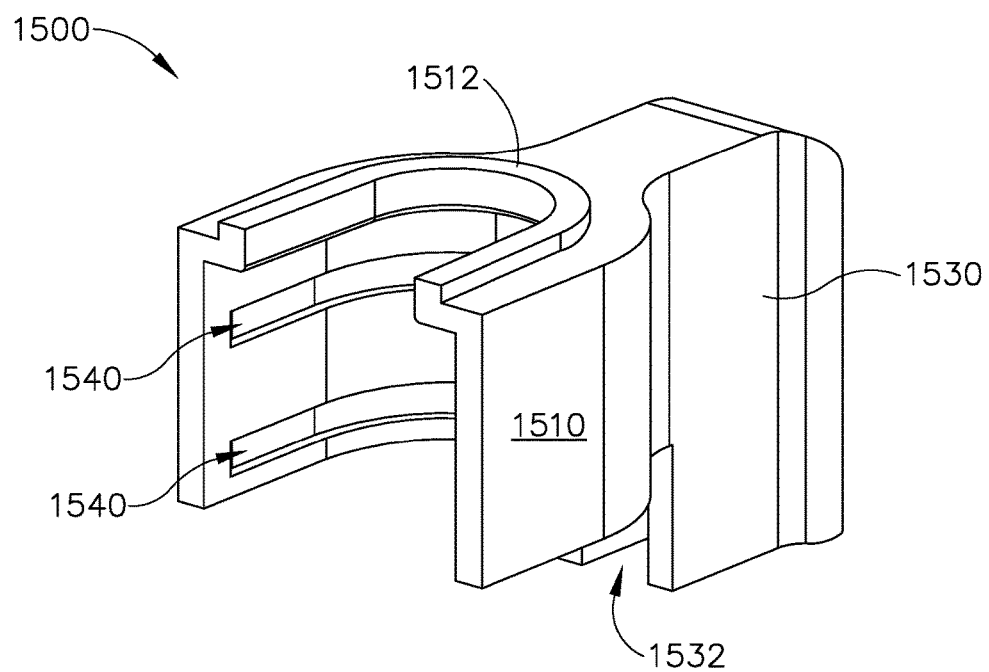
FIG. 34 depicts a perspective view of a third spacer of the fluid delivery assembly of FIG. 29.

As best seen in FIG. 34, third spacer (1500) comprise a sleeve (1510) and a grip (1530) extending laterally from sleeve (1510). Sleeve (1510) defines a "U" shape and includes an upper ledge (1512) and a pair of engagement channels (1540). Grip (1530) also defines a channel (1532). Third spacer (1500) is configured to fit around second spacer (1400), as shown in FIGS. 29-30, 35, and 36C. In particular, sleeve (1510) of third spacer (1500) is configured to encompass sleeve (1410) of second spacer (1400), with engagement ridges (1414) fitting in channels engagement (1540). Channel (1532) of grip (1530) is configured to accommodate grip (1430) of second spacer (1400) when spacers (1400, 1500) are coupled together. When engagement ridges (1414) are fully seated in engagement channels (1540), ridges (1414) and channels (1540) may cooperate to provide a snap fit between third spacer (1500) and second spacer (1400). Of course, any other suitable structures and techniques may be used to releasably secure third spacer (1500) to second spacer (1400). As best seen in FIG. 35, spacers (1400, 1500) are configured such that upper ledge (1512) is positioned higher than upper ledge (1412) when spacers (1400, 1500) are secured together. As also seen in FIG. 35, sleeves (1310, 1410, 1510) are all sized to enable shaft (1222) of plunger (1220) to translate freely relative to sleeves (1310, 1410, 1510). However, ledges (1312, 1412, 1512) are configured to engage thumb flange (1224) of plunger (1220) to thereby restrict movement of plunger (1220) as will be described in greater detail below.

FIGS. 36A-36G show an exemplary sequence of acts that may be performed using the components of fluid delivery assembly (1100). In particular, FIG. 36A shows syringe assembly (1200) coupled with a fluid source (1600), with plunger (1220) fully advanced relative to barrel (1210). Port (1212) may be coupled with fluid source (1600) via flexible tubing and/or via any other suitable structure or relationship as will be apparent to those of ordinary skill in the art in view of the teachings herein. It should be understood that fluid source (1600) may include fluid for forming leading bleb (340), therapeutic agent (341), and/or any other suitable fluid.

Figure 36C:
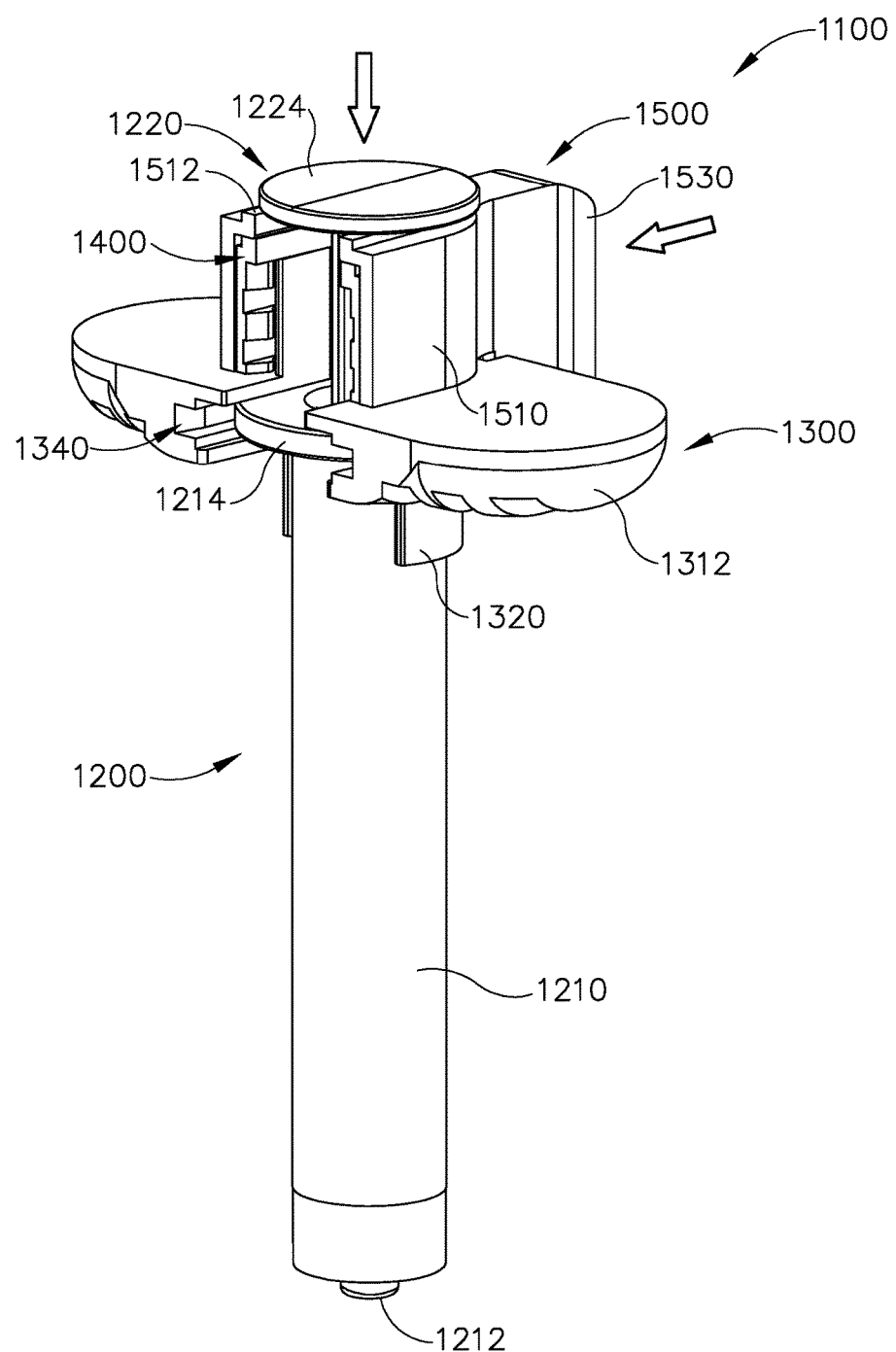
FIG. 36C depicts a perspective view of the spacers of the fluid delivery assembly of FIG. 29 secured to the syringe assembly of FIG. 36A, with the plunger in a first partially advanced position.

Once port (1212) is placed in fluid communication with fluid source (1600), plunger (1220) is refracted from barrel (1210) as shown in FIG. 36B, thereby drawing fluid from fluid source (1600) into barrel (1210). Once fluid has been drawn into barrel (1210), barrel (1210) is decoupled from fluid source (1600), and spacers (1300, 1400, 1500) are secured to syringe assembly (1200) as shown in FIG. 36C. With spacers (1300, 1400, 1500) secured to syringe assembly (1200), plunger (1220) is advanced until thumb flange (1224) engages upper ledge (1512) of third sleeve (1510), as also shown in FIG. 36C. Engagement between thumb flange (1224) and upper ledge (1512) arrests further movement of plunger (1220) into barrel (1210). It should be understood that during movement of plunger (1220) from the position shown in FIG. 36B to the position shown in FIG. 36C, air and some fluid may be expelled from barrel (1210). In the present example, barrel (1210) contains no air and only contains fluid from fluid source (1600) in the state shown in FIG. 36C. Thus, fluid delivery assembly (1100) may be considered as being in a primed state at the stage shown in FIG. 36C.

Figure 36D:
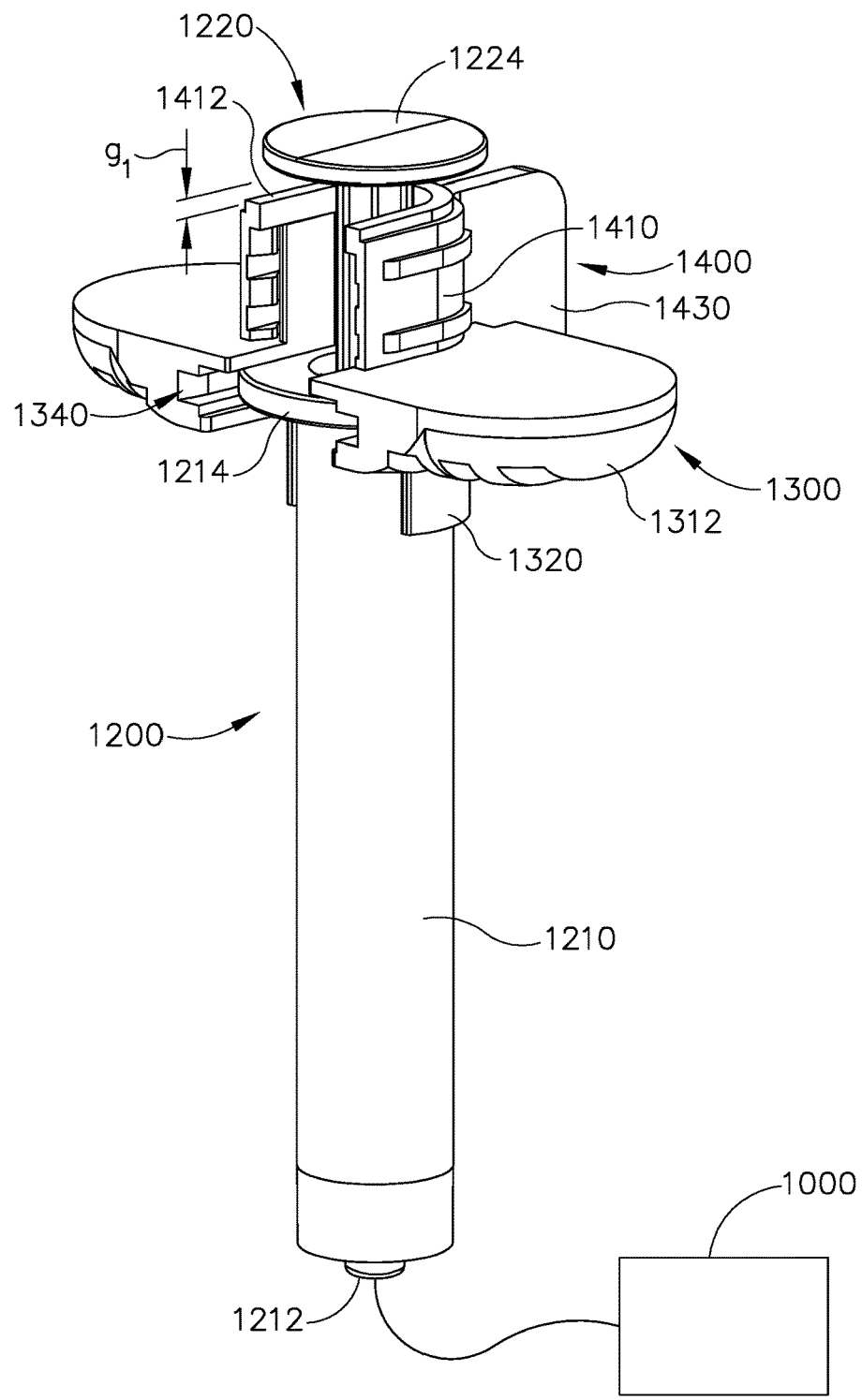
FIG. 36D depicts a perspective view of the fluid delivery assembly of FIG. 29, with the third spacer removed from the second spacer, and with the plunger in the first partially advanced position.

With fluid delivery assembly (1100) in the primed state, the operator may remove third spacer (1500) from second spacer (1400), resulting in the configuration shown in FIG. 36D. At this stage, a small gap ($g_1$) is defined between upper ledge (1412) of second spacer (1400) and the underside of thumb flange (1224). This gap ($g_1$) corresponds to the distance between upper ledges (1412, 1512) when spacers (1400, 1500) are coupled together. At this stage, port (1212) is also coupled with instrument (1000). As noted above, instrument (1000) may be configured and operable just like instrument (10, 2010) described above. Alternatively, instrument (1000) may take any other suitable form. It should also be understood that port (1212) may be coupled with instrument (1000) via flexible tubing and/or using any other suitable structures or techniques.

Figure 36E:
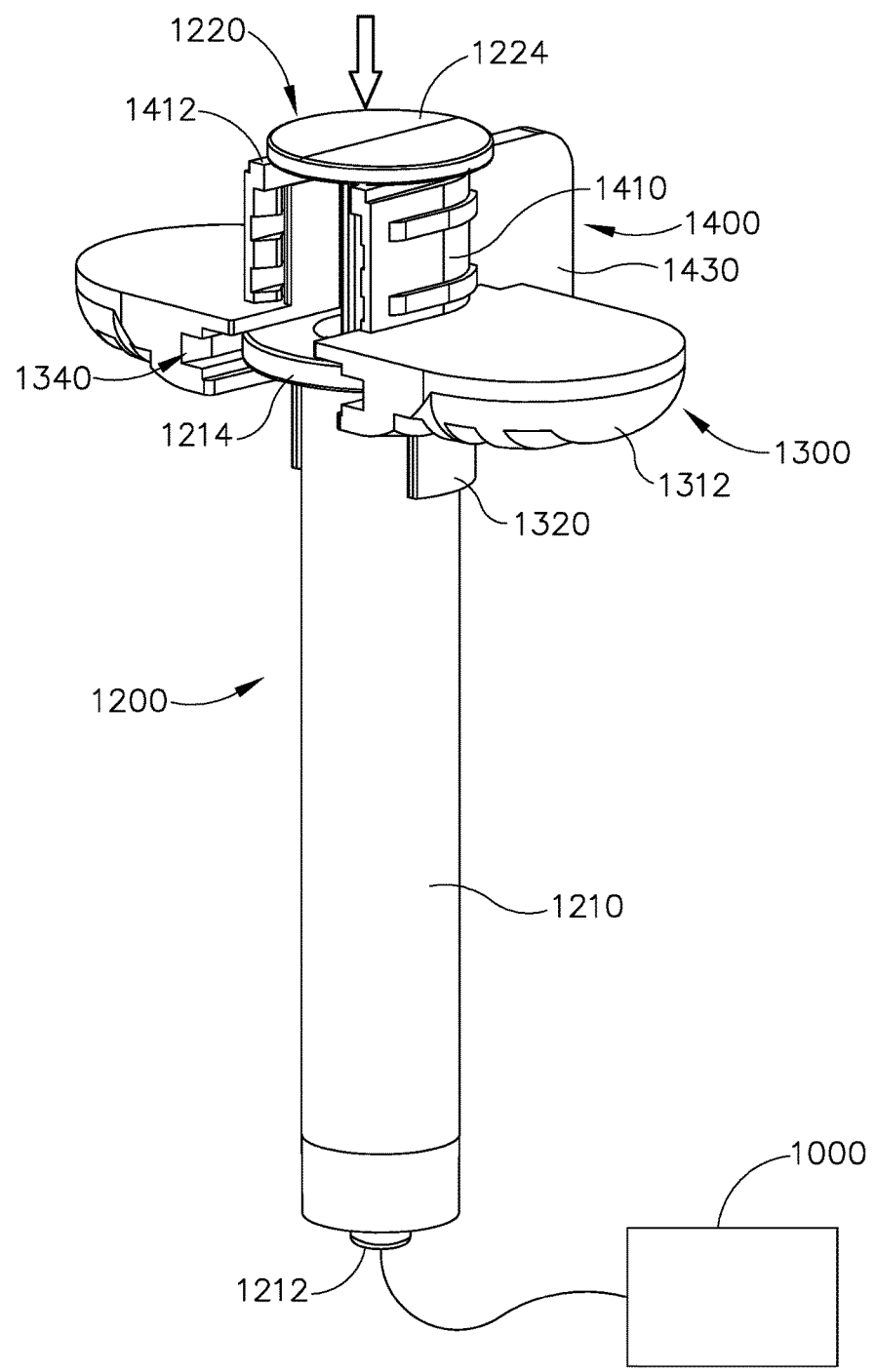
FIG. 36E depicts a perspective view of the fluid delivery assembly of FIG. 29, with the third spacer removed from the second spacer, and with the plunger in a second partially advanced position.

Once third spacer (1500) has been removed from second spacer (1400) and port (1212) has been coupled with instrument (1000), the operator may advance plunger (1220) further to the position shown in FIG. 36E. In particular, plunger (1220) is advanced until thumb flange (1224) engages upper ledge (1412) of second sleeve (1410). Engagement between thumb flange (1224) and upper ledge (1412) arrests further movement of plunger (1220) into barrel (1210). It should be understood that during movement of plunger (1220) from the position shown in FIG. 36D to the position shown in FIG. 36E, air and/or some fluid may be expelled from instrument (1000). In the present example, instrument (1000) contains no air and only contains fluid from fluid barrel (1210) (which is fluid from fluid source (1600)) in the state shown in FIG. 36E. Thus, instrument (1000) may be considered as being in a primed state at the stage shown in FIG. 36E. In some versions, the steps described above with respect to FIGS. 36A-36E are performed by a nurse; while the subsequent steps described below are performed by a surgeon. Of course, this is just one merely illustrative example. Any of the steps described herein may be performed by any suitable personnel.

Figure 36F:
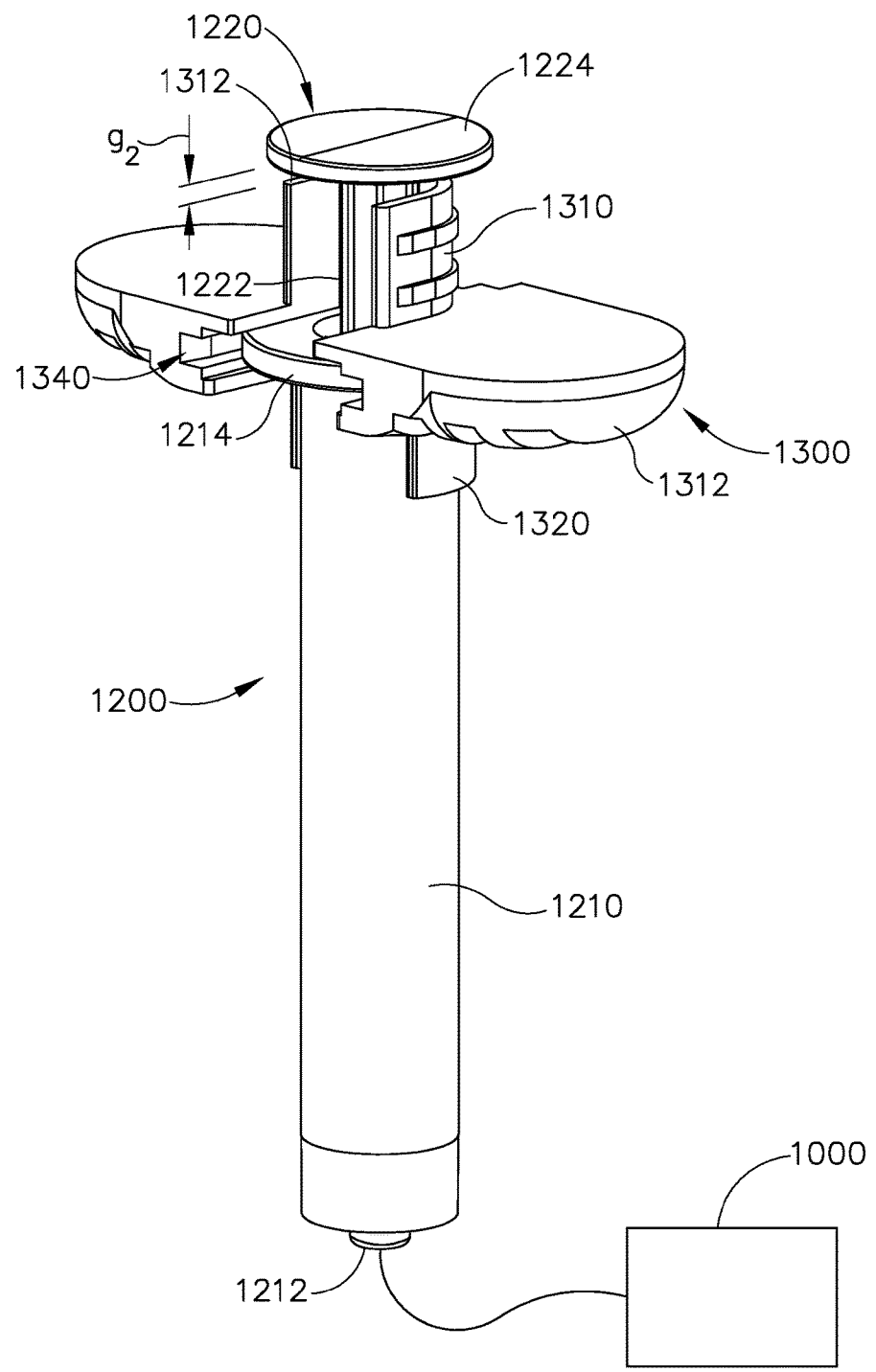
FIG. 36F depicts a perspective view of the fluid delivery assembly of FIG. 29, with the second spacer removed from the first spacer, and with the plunger in the second partially advanced position.

With instrument (1000) in the primed state, the operator may remove second spacer (1400) from first spacer (1300), resulting in the configuration shown in FIG. 36F. At this stage, a small gap ($g_2$) is defined between upper ledge (1312) of first spacer (1300) and the underside of thumb flange (1224). This gap ($g_2$) corresponds to the distance between upper ledges (1312, 1412) when spacers (1300, 1400) are coupled together. When instrument (1000) is positioned to deliver fluid to the patient (e.g., in the state shown in FIGS. 9H, 10E, and 11A; or in the state shown in FIGS. 9I, 10F, and 11B), the operator may then advance plunger (1220) further to the position shown in FIG. 36G. In particular, plunger (1220) is advanced until thumb flange (1224) engages upper ledge (1312) of upper sleeve (1310). Engagement between thumb flange (1224) and upper ledge (1312) arrests further movement of plunger (1220) into barrel (1210). It should be understood that during movement of plunger (1220) from the position shown in FIG. 36F to the position shown in FIG. 36G, fluid will be delivered to the patient via instrument (1000), in response to movement of plunger (1220) from the position shown in FIG. 36F to the position shown in FIG. 36G.

Figure 36G:
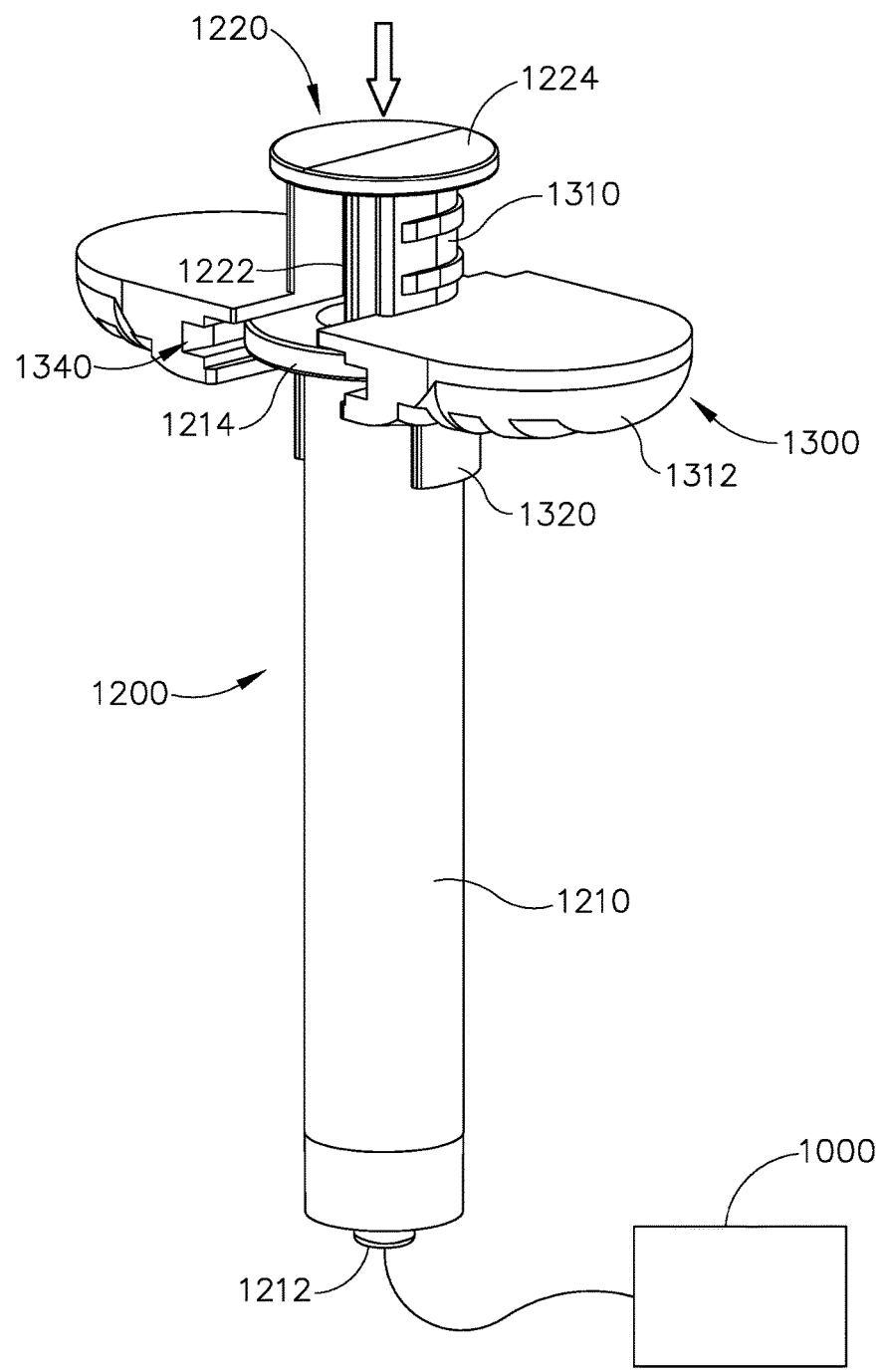
FIG. 36G depicts a perspective view of the fluid delivery assembly of FIG. 29, with the second spacer removed from the first spacer, and with the plunger in a third partially advanced position.

It should also be understood that the volume of fluid delivered to the patient via instrument (1000) during the transition from the state shown in FIG. 36F to the state shown in FIG. 36G will be fixed and predetermined. In particular, the volume of fluid delivered to the patient via instrument (1000) will be a function of the distance traversed by plunger (1220) during movement from the position shown in FIG. 36F to the position shown in FIG. 36G. This distance traveled is represented by the gap distance ($g_2$). This gap distance ($g_2$) is predefined as the distance between upper ledges (1312, 1412) when spacers (1300, 1400) are coupled together. Thus, the operator may consistently and confidently deliver the appropriate volume of fluid to the patient via instrument (1000). In the present example, the volume of fluid delivered during the transition from the state shown in FIG. 36F to the state shown in FIG. 36G is 50 µL. Alternatively, any other suitable volume may be provided.

It should be understood from the foregoing that the configuration of third spacer (1500) provides a predefined priming volume, such that third spacer (1500) may be regarded as a priming spacer; while the configuration of second spacer (1400) provides a predefined dosage volume, such that second spacer (1400) may be regarded as a dosage spacer. In some instances, the operator may be presented with a set of different spacers (1400), with the different spacers (1400) providing different heights between upper ledges (1312, 1412) to thereby provide delivery of different volumes of fluid. The operator may select the most appropriate second spacer (1400) from this set based on considerations such as the particular fluid being delivered, the medical condition being treated, patient physiology, etc. The operator may then use the selected second spacer (1400) to assembly fluid delivery system (1100) as shown in FIG. 36C and carry out the rest of the steps as described above with reference to FIGS. 36C-36G. In any case, there may be some amount of fluid that is left in barrel (1210) after reaching the stage shown in FIG. 36G. This excess fluid may simply be disposed of or otherwise dealt with.

IX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for storing and delivering a predetermined amount of fluid, the system comprising: (a) a syringe defining a longitudinal axis, comprising: (i) a barrel comprising: (A) a first end, (B) a second end, and (C) a lumen extending between the first and second ends, (ii) a first flange disposed at the second end and extending away from the longitudinal axis, and (iii) a plunger assembly configured to be received in the lumen of the barrel and move relative to the lumen to draw fluid into and dispense fluid from the syringe, wherein the plunger assembly comprises: (A) a piston, (B) a plunger rod comprising a first end and a second end, wherein the first end of the plunger rod is coupled with the piston, wherein the plunger rod comprises a second flange at the second end of the plunger rod; and (b) a first stop feature, wherein the first stop feature is removably couplable to at least one of the barrel, the first flange, or the plunger assembly, wherein the first stop feature is configured to restrict advancement of the plunger assembly relative to the barrel to prevent the plunger assembly from advancing beyond a predetermined distance from either a portion of the first flange or a portion of the barrel.

Example 2

The system of Example 1, further comprising a second stop feature, wherein the second stop feature is removably coupleable to the first stop feature, wherein the second stop feature is configured to restrict advancement of the plunger assembly relative to the barrel to prevent the plunger assembly from advancing beyond a second predetermined distance from either a portion of the first flange or a portion of the barrel.

Example 3

The system of any one or more of Examples 1 through 2, wherein the plunger rod is threadably coupled with the piston.

Example 4

The system of Example 3, wherein the first end of the plunger rod comprises a threaded portion, wherein the piston comprises a threaded aperture configured to receive the threaded portion of the plunger rod.

Example 5

The system of any one or more of Examples 1 through 4, wherein the first stop feature comprises an engagement portion, wherein a portion of the engagement portion has a shape that is complementary to a cross-sectional profile of the plunger rod.

Example 6

The system of any one or more of Examples 1 through 5, wherein the first stop feature is configured to prevent distal movement of the plunger assembly relative to the barrel when the second flange is a predetermined distance from the first flange.

Example 7

The system of Example 6, wherein the first stop feature is configured to abut the second flange and the first flange when the second flange is positioned at the predetermined distance from the first flange.

Example 8

The system of any one or more of Examples 1 through 7, further comprising an adapter, wherein the plunger rod is configured to decouple from the piston, wherein the adapter is configured to be received in the second end of the barrel in the absence of plunger rod, wherein the adapter is configured to fluidly couple the syringe with a source of pressurized fluid to move the piston within the lumen.

Example 9

The system of Example 8, wherein the adapter comprises a first tubular portion, a second tubular portion, and a third flange between the first and second tubular portions, wherein the first tubular portion is configured to be received in the second end of the barrel in the absence of plunger rod, wherein the third flange is configured to abut the first flange when the first tubular portion is received in the second end of barrel.

Example 10

The system of Example 9, further comprising a collar, wherein the collar is configured to secure the adapter to the syringe.

Example 11

The system of Example 10, wherein the collar is configured to envelop at least a portion of the first flange and at least a portion of the third flange.

Example 12

The system of any one or more of Examples 10 through 11, wherein the collar further comprises a cavity configured to receive at least a portion of the first flange and at least a portion of the third flange.

Example 13

The system of Example 12, wherein the collar further comprises a ramp feature, wherein the ramp feature is configured to urge the first and third flanges toward each other when the first and third flanges are directed into the cavity.

Example 14

The system of Example 13, wherein the ramp feature includes a tapered leading portion.

Example 15

The system of any one or more of Examples 10 through 14, further comprising: (a) a pump operable to provide a pressurized fluid medium; and (b) a pressure regulator, wherein the pressure regulator is in fluid communication with the pump and is thereby operable to regulate the pressure of the pressurized fluid medium provided by the pump, wherein the pressure regulator is further in communication with the syringe such that the syringe is operable to receive the pressurized fluid medium.

Example 16

A method of filling and priming a syringe, wherein the syringe defines a longitudinal axis, wherein the syringe comprises a barrel and a plunger assembly including a plunger rod removably coupled to a piston, the method comprising: (a) fluidly coupling the barrel with a source of fluid; (b) moving the plunger assembly relative to the barrel in a first direction along the longitudinal axis to draw fluid into the barrel; (c) removably coupling a stop member to a portion of the syringe or the plunger rod; (d) moving the plunger assembly relative to the barrel in a second direction that is opposite to the first direction until the stop member prevents further the movement of the plunger assembly in the second direction; and (e) decoupling the plunger rod from the piston and removing the plunger rod from the barrel.

Example 17

The method of Example 16, further comprising decoupling the stop member from the syringe or the plunger rod.

Example 18

The method of any one or more of Examples 16 through 17, wherein decoupling the plunger rod from the piston further comprises rotating the plunger rod relative to the plunger to release a threaded engagement between the plunger rod and the piston.

Example 19

The method of any one or more of Examples 16 through 18, further comprising: (a) fluidly coupling the syringe to a source of pressurized fluid; and (b) directing the pressurized fluid into the syringe to advance the piston further in the second direction.

Example 20

A method of operating a syringe, wherein the syringe defines a longitudinal axis, wherein the syringe comprises a barrel including a proximal end and a distal end, wherein the syringe further comprises a plunger assembly configured to be received in the proximal end of the barrel, wherein the plunger assembly comprises a plunger rod removably coupled to a piston, the method comprising: (a) fluidly coupling the distal end of the barrel with a source of fluid; (b) moving the plunger assembly proximally relative to the barrel along the longitudinal axis to draw fluid into the barrel, wherein the fluid is received distal to the piston; (c) priming the syringe to purge air from the syringe; (d) decoupling the plunger rod from the piston and removing the plunger rod from the barrel; (e) fluidly coupling the barrel to a source of pressurized fluid at the proximal end of the barrel; and (f) directing pressurized fluid into the barrel to advance the piston distally, wherein the act of directing pressurized fluid into the barrel comprises directing the pressurized fluid proximal to the piston.

X. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for storing and delivering a predetermined amount of fluid, the system comprising:
   (a) a syringe defining a longitudinal axis, comprising:
      (i) a barrel comprising:
         (A) a first end,
         (B) a second end, and
         (C) a lumen extending between the first and second ends,
      (ii) a first flange disposed at the second end and extending away from the longitudinal axis, and
      (iii) a plunger assembly configured to be received in the lumen of the barrel and move relative to the lumen to draw fluid into and dispense fluid from the syringe, wherein the plunger assembly comprises:
         (A) a piston, and
         (B) a plunger rod comprising a first end and a second end, wherein the first end of the plunger rod is coupled with the piston, wherein the plunger rod comprises a second flange at the second end of the plunger rod;
   (b) a first stop feature, wherein the first stop feature includes:
      (i) at least one snap fit feature, wherein the first stop feature is removably coupleable in a snap fit manner to at least one of the barrel, the first flange, or the plunger assembly using the at least one snap fit feature,
      (ii) a proximal flange disposed at a proximal most end of the first stop feature and extending perpendicular to the longitudinal axis, wherein the proximal flange is configured to contact the first flange of the syringe, and
      (iii) a distal flange disposed at a distal most end of the stop feature and extending perpendicular to the longitudinal axis, wherein the proximal and distal flanges are configured to restrict advancement of the plunger assembly relative to the barrel to prevent the plunger assembly from advancing beyond a first predetermined distance from either a portion of the first flange or a portion of the barrel;
   (c) an adaptor that includes a third flange; and
   (d) a collar that includes a ramp feature, wherein the ramp feature extends transversely to the longitudinal axis, wherein the ramp feature is configured to urge the first and third flanges toward each other.

2. The system of claim 1, wherein the plunger rod is threadably coupled with the piston.

3. The system of claim 2, wherein the first end of the plunger rod comprises a threaded portion, wherein the piston comprises a threaded aperture configured to receive the threaded portion of the plunger rod.

4. The system of claim 1, wherein the first stop feature comprises an engagement portion, wherein a portion of the engagement portion has a shape that is complementary to a cross-sectional profile of the plunger rod.

5. The system of claim 1, wherein the plunger rod is configured to decouple from the piston, wherein the adapter is configured to be received in the second end of the barrel in the absence of plunger rod, wherein the adapter is configured to fluidly couple the syringe with a source of pressurized fluid to move the piston within the lumen.

6. The system of claim 5, wherein the adapter comprises a first tubular portion and a second tubular portion, wherein the third flange is disposed between the first and second tubular portions, wherein the first tubular portion is configured to be received in the second end of the barrel in the absence of plunger rod, wherein the third flange is configured to abut the first flange when the first tubular portion is received in the second end of the barrel.

7. The system of claim 6, wherein the collar is configured to secure the adapter to the syringe.

8. The system of claim 7, wherein the collar is configured to envelop at least a portion of the first flange and at least a portion of the third flange.

9. The system of claim 7, wherein the collar further comprises a cavity configured to receive at least a portion of the first flange and at least a portion of the third flange.

10. The system of claim 9, wherein the ramp feature is configured to urge the first and third flanges toward each other when the first and third flanges are directed into the cavity.

11. The system of claim 10, wherein the ramp feature includes a tapered leading portion.

12. The system of claim 7, further comprising:
(a) a pump operable to provide a pressurized fluid medium; and
(b) a pressure regulator, wherein the pressure regulator is in fluid communication with the pump and is thereby operable to regulate the pressure of the pressurized fluid medium provided by the pump, wherein the pressure regulator is further in communication with the syringe such that the syringe is operable to receive the pressurized fluid medium.

13. A method of operating a syringe, wherein the syringe defines a longitudinal axis, wherein the syringe comprises a barrel and a plunger assembly including a plunger rod removably coupled to a piston, the method comprising:
(a) fluidly coupling the barrel with a source of fluid;
(b) moving the plunger assembly relative to the barrel in a first direction along the longitudinal axis to draw fluid into the barrel;
(c) removably coupling a stop member to a portion of the syringe or the plunger rod;
(d) moving the plunger assembly relative to the barrel in a second direction that is opposite to the first direction until the stop member prevents further movement of the plunger assembly in the second direction;
(e) decoupling the plunger rod from the piston and removing the plunger rod from the barrel;
(f) securing an adapter to the syringe using a collar, wherein the collar comprises at least one ramp feature extending transversely parallel to the longitudinal axis, wherein the at least one ramp feature includes a tapered leading portion that urges a flange of the adaptor towards a flange of the syringe; and
(g) subsequently advancing the piston further in the second direction.

14. The method of claim 13, further comprising decoupling the stop member from the syringe or the plunger rod.

15. The method of claim 13, wherein decoupling the plunger rod from the piston further comprises rotating the plunger rod relative to the piston to release a threaded engagement between the plunger rod and the piston.

16. The method of claim 13, further comprising:
(a) fluidly coupling the syringe to a source of pressurized fluid; and
(b) directing the pressurized fluid into the syringe to advance the piston further in the second direction.

17. The method of claim 13, wherein the first stop member includes a grip portion extending between the proximal and distal flanges.

18. The method of claim 13, wherein the adaptor includes proximal and distal portions, wherein the distal portion of the adaptor includes at least one O-ring, wherein the method further includes coupling the proximal end of the adaptor to proximal using a barbed connection feature.

19. A method of operating a syringe, wherein the syringe defines a longitudinal axis, wherein the syringe comprises a barrel including a proximal end and a distal end, wherein the syringe further comprises a plunger assembly configured to be received in the proximal end of the barrel, wherein the plunger assembly comprises a threaded plunger rod removably coupled to a threaded piston, the method comprising:
(a) fluidly coupling the distal end of the barrel with a source of fluid;
(b) moving the plunger assembly proximally relative to the barrel along the longitudinal axis to draw fluid into the barrel, wherein the fluid is received distal to the threaded piston;
(c) priming the syringe to purge air from the syringe;
(d) decoupling the threaded plunger rod from the threaded piston and removing the threaded plunger rod from the barrel while leaving the threaded piston in contact with the fluid;
(e) fluidly coupling the barrel to a source of pressurized fluid at the proximal end of the barrel using a collar, wherein the collar comprises at least one ramp feature extending transversely to the longitudinal axis that urges a flange of an adaptor towards a flange of the syringe; and
(f) subsequently directing pressurized fluid into the barrel to advance the threaded piston distally, wherein the act of directing pressurized fluid into the barrel comprises directing the pressurized fluid proximal to the threaded piston.

20. The method of claim 19, wherein the threaded plunger rod is externally threaded and the piston is internally threaded.

* * * * *